US008258095B2

(12) United States Patent
Boss et al.

(10) Patent No.: US 8,258,095 B2
(45) Date of Patent: Sep. 4, 2012

(54) METHOD OF CONTROLLING GLYCEMIA BY ULTRARAPID ACTING INSULIN WITHOUT ADJUSTING AN INSULIN DOSE FOR MEAL CONTENT

(75) Inventors: Anders Hasager Boss, Princeton, NJ (US); Richard Petrucci, New Canaan, CT (US); Campbell Howard, Yardley, PA (US); Alfred Mann, Valencia, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 12/539,499

(22) Filed: Aug. 11, 2009

(65) Prior Publication Data

US 2010/0035795 A1 Feb. 11, 2010

Related U.S. Application Data

(60) Provisional application No. 61/087,943, filed on Aug. 11, 2008, provisional application No. 61/097,495, filed on Sep. 16, 2008, provisional application No. 61/097,516, filed on Sep. 16, 2008, provisional application No. 61/138,863, filed on Dec. 18, 2008.

(51) Int. Cl.
*A61P 3/10* (2006.01)
*A61K 38/00* (2006.01)

(52) U.S. Cl. .............................. 514/6.8; 514/5.9; 514/6.9

(58) Field of Classification Search .................... None
See application file for complete search history.

(56) References Cited

U.S. PATENT DOCUMENTS

| 5,352,461 | A | 10/1994 | Feldstein et al. |
| 5,360,614 | A * | 11/1994 | Fox et al. ...................... 424/439 |
| 5,503,852 | A | 4/1996 | Steiner et al. |
| 5,506,203 | A | 4/1996 | Backstrom et al. |
| 5,547,929 | A | 8/1996 | Anderson, Jr. et al. |
| 5,888,477 | A | 3/1999 | Gonda et al. |
| 5,976,569 | A | 11/1999 | Milstein |
| 6,071,497 | A | 6/2000 | Steiner et al. |
| 6,187,291 | B1 | 2/2001 | Weinstein et al. |
| 6,331,318 | B1 | 12/2001 | Milstein |
| 6,395,774 | B1 | 5/2002 | Milstein |
| 6,428,771 | B1 | 8/2002 | Steiner et al. |
| 6,440,463 | B1 | 8/2002 | Feldstein et al. |
| 6,444,226 | B1 | 9/2002 | Steiner et al. |
| 6,447,751 | B1 | 9/2002 | Weinstein et al. |
| 6,652,838 | B2 | 11/2003 | Weinstein et al. |
| 6,652,885 | B2 | 11/2003 | Steiner et al. |
| 6,923,175 | B2 | 8/2005 | Poole et al. |
| 7,464,706 | B2 | 12/2008 | Steiner et al. |
| 7,625,865 | B2 | 12/2009 | Colombo et al. |
| 7,648,960 | B2 | 1/2010 | Steiner et al. |
| 7,943,178 | B2 | 5/2011 | Steiner et al. |
| 7,943,572 | B2 | 5/2011 | Cheatham et al. |
| 2004/0062722 | A1 | 4/2004 | Gonda et al. |
| 2004/0138099 | A1 * | 7/2004 | Draeger ............................ 514/3 |
| 2004/0182387 | A1 | 9/2004 | Steiner et al. |
| 2005/0153874 | A1 | 7/2005 | Cheatham et al. |
| 2006/0040953 | A1 | 2/2006 | Leone-Bay et al. |
| 2006/0153778 | A1 * | 7/2006 | Gelber et al. ..................... 424/46 |
| 2006/0160722 | A1 * | 7/2006 | Green et al. ....................... 514/3 |
| 2006/0165756 | A1 * | 7/2006 | Catani et al. ................... 424/439 |
| 2006/0239934 | A1 * | 10/2006 | Cheatham et al. ............... 424/46 |
| 2007/0020191 | A1 | 1/2007 | Boss et al. |
| 2007/0027063 | A1 | 2/2007 | Boss et al. |
| 2007/0059373 | A1 | 3/2007 | Oberg |
| 2007/0196503 | A1 | 8/2007 | Wilson et al. |

FOREIGN PATENT DOCUMENTS

| EP | 0220958 | 5/1987 |
| WO | 96/36314 | 11/1996 |
| WO | 99/52506 | 10/1999 |
| WO | 01/00654 | 1/2001 |

OTHER PUBLICATIONS

Pearson et al., Systematically Initiating Insulin, supplemental to vol. 32, No. 1, 19S-28S, 2006.*
Cobble ME. "Initiating and Intensifying Insulin Therapy for Type 2 Diabetes: Why, When, and How." Am J Ther. Jan. 8, 2009.
Alabraba V. et al. Diabetes Technology & Therapeutics. Jul. 2009, 11(7): 427-430.
Clee, SM et al. Nature Genetics 38:688-693, 2006.
Matthews DR et al. "Homeostasis model assessment: insulin resistance and beta-cell function from fasting plasma glucose and insulin concentrations in man." Diabetologia. Jul. 1985;28(7):412-9.
American Diabetes Association. "Standards of medical care in diabetes—2009." Diabetes Care. Jan. 2009;32 Suppl 1: S13-61.
The DECODE study group. "Glucose tolerance and mortality: comparison of WHO and American Diabetes Association diagnostic criteria." Lancet. Aug. 21, 1999;354(9179):617-21.
ACTOS Product Insert. Aug. 2008.
AVANDIA Product Insert, Oct. 2008.
Brownlee M and Hirsch IB "Glycemic variability: a hemoglobin A1c-independent risk factor for diabetic complications." JAMA 295:1707, 2006.
Halozyme Press Release. Jun. 6, 2009.
Heinemann L and Heise T. "Current status of the development of inhaled insulin." Br. J. Diabetes Vasc. Dis. 4:295-301, 2004.
GLUCOPHAGE Product Insert. Jan. 2009.
GLUCOTROL Product Insert. Sep. 2006.
Katz A. et al. "Quantitative insulin sensitivity check index: a simple, accurate method for assessing insulin sensitivity in humans." J. Clin. Endocrinol. Metab. 85:5402-2410, 2000.
MannKind Corporation "Postprandial hyperglycemia: clinical significance, pathogenesis and treatment." MannKind Corporation Monograph. 2009.

(Continued)

*Primary Examiner* — Gyan Chandra
(74) *Attorney, Agent, or Firm* — K&L Gates LLP; Louis C. Cullman; Brent A. Johnson

(57) ABSTRACT

Disclosed herein are improved methods of treating hyperglycemia with a combination of an ultrarapid acting insulin and insulin glargine comprising prandial administration of the ultrarapid insulin, and administration of a first dose of insulin glargine within 6 hours of waking for a day.

11 Claims, 18 Drawing Sheets

OTHER PUBLICATIONS

Monnier L. et al. "Activation of oxidative stress by acute glucose fluctuations compared with sustained chronic hyperglycemia in patients with type 2 diabetes." JAMA 295:1681, 2006.

Nathan DM et a. "Intensive diabetes treatment and cardiovascular disease in patients with Type 1 diabetes." New Eng. J. Med. 353:2643-2653, 2005.

Nathan DM et al. "Management of hyperglycemia in Type 2 diabetes: a consensus algorithm for the initiation and adjustment of therapy." Diabetes Care 29:1963, 2006.

Nathan DM et al. "Management of hyperglycemia in Type 2 diabetes: a consensus algorithm for the initiation and adjustment of therapy." Diabetes Care 31:173, 2008.

Nathan DM et al. "Management of hyperglycemia in Type 2 diabetes: a consensus algorithm for the initiation and adjustment of therapy." Diabetes Care 32:193, 2009.

Rosenstock J. "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.

Hausmann M et al. "Inhaled insulin as adjunctive therapy in subjects with type 2 diabetes failing oral agents: a controlled proof-of-concept study." Diabetes Obesity Metab 8:574-580, 2006.

Hite PF et al. "Exhuberance over Exubera." Clin Diabetes 24:110-114, 2006.

Pfutzner et al "Technosphere/Insulin—A New Approach for Effective Delivery of Human Insulin Via the Pulmonary Route." Dibetes Technology & Therapeutics, vol. 4, No. 5, 2002.

Rosenstock J et al. "Inhaled insulin improves glycemic control when substituted for or added to oral combination therapy in Type 2 diabetes." Ann Intern Med 143:549-558, 2005.

Mastrandrea "A breath of life for inhaled insulin: sever subcutaneous insulin resistance as an indication." Pediatric Diabetes 2010: 11: 377-379.

Van Alfen-Van Der Velden et al. "Successful treatment of severe subcutaneous insulin resistance with inhaled insulin therapy." Pediatric Diabetes 2010: 11: 380-382.

USPTO Transaction History of U.S. Appl. No. 11/461,746.

USPTO Transaction History of U.S. Appl. No. 13/077,361.

Ashwell et al. "Optimal timing of injection of once-daily insulin glargine in people with Type 1 diabetes using insulin lispro at mealtimes." 2005 Diabetes UK, Diabetic Medicine, 23, 46-52.

Ashwell et al. "Twice-daily compared with once-daily insulin glargine in people with Type 1 diabetes using meal-time insulin aspart." 2006 Diabetes UK, Diabetic Medicine, 23, 879-886.

Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.

Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.

Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121, e466-e472, 2008.

Standl et al. "Good Glycemic Control With Flexibility in Timing of Basal Insulin Supply." Diabetes Care, vol. 28, No. 2, Feb. 2005.

Cefalu et al. "Inhaled Human Insulin Treatment in Patients with Type 2 Diabetes Mellitus." Annals of Internal Medicine, Feb. 6, 2001, vol. 134, No. 3.

Warren et al. "Postprandial Versus Preprandial Dosing of Biphasic Insulin Aspart in Elderly Type 2 Diabetes Patients." Diabetes Research and Clinical Practive, vol. 66, pp. 23-29, 2004.

Cefalu "Concept, Strategies and Feasibility of Noninvasive Insulin Delivery." Diabetes Care 27:239-246, 2004.

Cernea et al. "Dose-Response Relationship of Oral Insulin Spray in Healthy Subjects." Diabetes Care, vol. 28, No. 6, pp. 1353-1357, 2005.

Cheatham et al. "Desirable Dynamics & Performance of Inhaled Insulin Compared to Subcutaneous Insulin Given at Mealtime in Type 2 Diabetes: A Report from the Technosphere/Insulin Study Group." pp. 235-235, 2004.

Edelman "Type II Diabetes Mellitus." Adv Int Med, 43:449-500, 1998.

Farr, SJ et al. "Pulmonary insulin administration using the AERx(R) system: physiological and physiochemical factors influencing insulin effectiveness in healthy fasting subjects." Diabetes Tech. Ther. 2:185-197, 2000.

Gupta et al. "Contemporary Approaches in Aerosolized Drug Delivery to the Lung." J. Controlled Research, 17:129-148, 1991.

Heineman et al. "Current Status of the Development of Inhaled Insulin." Br J Diabetes Vasc Dis, 4:295-301, 2004.

Hussain et al. "State of insulin self-association does not affects its absorption from the pulmonary route." Eur. J. Pharm. Sciences 25:289-298, 2005.

Kohler et al. "Non-Radioactive Approach for Measuring Lung Permeability: Inhalation of Insulin." Atemw Lungenkrkh, 13:230-232, 1987 (Original German and English translation attached).

Leahy et al. "Beta-ell Dysfunction in Type II Diabetes Mellitus." Curr Opin Endocrinol Diabetes, 2:300-306, 1995.

Lian et al. "A Self-Complimentary Self-Assembling Microsphere System: Application for Intravenous Delivery of the Antiepilpetic and Neuroprotectant Compound Felbanate." J Phatm Sci 89:867-875, 2000.

Pfeifer et al. "Insulin Secretion in Diabetes Mellitus." Am J. Med, 70:579-588, 1981.

Polonsky et al. "Abnormal Patterns of Insulin Secretion in Non-Insulin-Dependent Diabetes Mellitus." N Eng J Med, 318:1231-1239, 1988.

Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.

Raskin et al. "Continuous Subcutaneous Insulin Infusion and Multiple Daily Injection Therapy are Equally Effective in Type 2 Diabetes." Diabetes Care, vol. 26, No. 9, pp. 2598-2603, Sep. 2003.

Steiner et al. "Technosphere (TM)/Insulin—Proof of Concept Study with a New Insulin Formulation for Pulmonary Delivery." Exp Clin Endocrinol Diabetes, 110:17-21, 2002.

* cited by examiner

Seven-point Blood Glucose Profiles at Week 52 (ITT Population)

Fasting blood glucose over time.

Seven point blood glucose profile: baseline and 52 weeks.

FIG. 16

| Demographic and Baseline Characteristics by Randomized Treatment Group (ITT Population) | | | | |
|---|---|---|---|---|
| Characteristic | Statistic | TI Alone (n = 177) | Metformin + Secretagogue (n = 162) | TI + Metformin (n = 169) |
| Gender, Number of Subjects (%) | | | | |
| ➢ Male | | 84 (47.5) | 74 (45.7) | 68 (40.2) |
| ➢ Female | | 93 (52.5) | 88 (54.3) | 101 (59.8) |
| Race, Number of Subjects (%) | | | | |
| ➢ Caucasian | | 133 (75.1) | 114 (70.4) | 129 (76.3) |
| ➢ Black | | 9 (5.1) | 8 (4.9) | 12 (7.1) |
| ➢ Asian | | 4 (2.3) | 5 (3.1) | 2 (1.2) |
| ➢ Hispanic | | 26 (14.7) | 25 (15.4) | 23 (13.6) |
| ➢ Other | | 5 (2.8) | 10 (6.2) | 3 (1.8) |
| Age, Years | | | | |
| | Mean (SD) | 57.3 (8.47) | 57.6 (9.14) | 56.8 (8.31) |
| Weight, Kilograms | | | | |
| | Mean (SD) | 86.14 (15.59) | 84.18 (16.21) | 83.87 (13.93) |
| BMI, kg/m2 | | | | |
| | Mean (SD) | 31.23 (4.30) | 30.73 (4.61) | 30.81 (4.40) |
| Baseline HbA1c (%) | | | | |
| | Mean (SD) | 8.92 (0.95) | 8.90 (0.94) | 8.95 (0.97) |
| Fasting Plasma Glucose (mg/dL) | | | | |
| | Mean (SD) | 193.59 (53.58) | 197.31 (47.96) | 189.39 (47.34) |
| • Percentages are based on the number of subjects in each treatment group in the specified population (n). Statistics are summarized by the randomized treatment group. SD=Standard Deviation | | | | |

METHOD OF CONTROLLING GLYCEMIA BY ULTRARAPID ACTING INSULIN WITHOUT ADJUSTING AN INSULIN DOSE FOR MEAL CONTENT

CROSS-REFERENCE TO RELATED APPLICATIONS

This application claims benefit of priority under 35 U.S.C. §119(e) from U.S. Provisional Patent Applications Ser. Nos. 61/087,943 filed Aug. 11, 2008, 61/097,495 and 61/097,516 filed Sep. 16, 2008, and 61/138,863 filed Dec. 18, 2008, the contents of each of these applications are incorporated herein by reference in their entirety.

FIELD OF THE INVENTION

The present invention relates to methods for treating diabetes mellitus with an ultrarapid acting prandial insulin. Particular embodiments of the invention relate to various modes of administration which take advantage of the unique kinetic profile of such formulations, as well as substitution of such an insulin for one or more oral antidiabetic agents in the standard treatment regimen of diabetes mellitus, type 2.

BACKGROUND OF THE INVENTION

Diabetes mellitus (hereinafter, diabetes) currently afflicts at least 200 million people worldwide. The two main subtypes of diabetes include types 1 and 2. Type 1 diabetes accounts for about 10% of the 200 million afflicted with diabetes. Type 1 diabetes is caused by autoimmune destruction of insulin-secreting β-cells in the pancreatic islets of Langerhans. Type 2 diabetes accounts for the remaining 90% of individuals afflicted, and the prevalence is increasing. Type 2 diabetes is often, but not always, associated with obesity, and although previously termed late-onset or adult-onset diabetes, is now becoming increasingly more prevalent in younger individuals. Type 2 diabetes is caused by a combination of insulin resistance and inadequate insulin secretion.

The Physiological Role of Insulin

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

Five different phases of insulin secretion have been identified: (1) basal insulin secretion wherein insulin is released in the postabsorptive state; (2) the cephalic phase wherein insulin secretion is triggered by the sight, smell and taste of food, before any nutrient is absorbed by the gut, mediated by pancreatic innervation; (3) early-phase insulin secretion wherein an initial burst of insulin is released within the first 5-10 minutes after the β-cell is exposed to a rapid increase in glucose, or other secretagogues; (4) second-phase insulin secretion wherein the insulin levels rise more gradually and are related to the degree and duration of the stimulus; and (5) a third-phase of insulin secretion that has only been described in vitro. During these stages, insulin is secreted, like many other hormones, in a pulsatile fashion, resulting in oscillatory concentrations in the blood. Oscillations include rapid pulses (occurring every 8-15 minutes) superimposed on slower oscillations (occurring every 80-120 minutes) that are related to fluctuations in blood glucose concentration.

Insulin secretion can be induced by other energetic substrates besides glucose (particularly amino acids) as well as by hormones and drugs. Of note is that the insulin response observed after food ingestion cannot be accounted for solely by the increase in blood glucose levels, but also depends on other factors such as the presence of free fatty acids and other secretagogues in the meal, the neurally activated cephalic phase and gastrointestinal hormones.

When an individual is given an intravenous glucose challenge, a biphasic insulin response is seen which includes a rapid increase with a peak, an interpeak nadir and a subsequent slower increasing phase. This biphasic response is only seen when glucose concentration increases rapidly, such as after a glucose bolus or glucose infusion. A slower increase in glucose administration, what is seen under physiologic conditions, induces a more gradually increasing insulin secretion without the well-defined biphasic response seen in response to bolus infusion of glucose.

Modeling of early-phase insulin responses under normal physiologic conditions has demonstrated that, after a meal, glucose concentration increases more gradually ($C_{max}$ reached in approximately 20 minutes) than seen with intravenous bolus injections of glucose ($C_{max}$ reached in approximately 3-10 minutes).

Healthy pancreatic β-cells generate an early response to a meal-like glucose exposure that rapidly elevates serum insulin both in the portal circulation and in the periphery. Conversely, defective β-cells, which have an impaired early-phase insulin response, generate a sluggish response to the meal-like glucose exposure.

Increasingly, evidence indicates that an early relatively rapid insulin response following glucose ingestion plays a critical role in the maintenance of postprandial glucose homeostasis. An early surge in insulin concentration can limit initial glucose excursions, mainly through the inhibition of endogenous glucose production. Therefore the induction of a rapid insulin response in a diabetic individual is expected to produce improved blood glucose homeostasis.

In a normal individual, a meal induces the secretion of a burst of insulin, generating a relatively rapid spike in serum insulin concentration that then decays relatively quickly (see FIG. 1). This early-phase insulin response is responsible for the shut-off, or reduction, of glucose release from the liver. Homeostatic mechanisms then match insulin secretion (and serum insulin levels) to the glucose load. This is observed as a slow decay of modestly elevated serum insulin levels back to baseline and is second-phase kinetics.

Diabetes

A central characteristic of diabetes is impaired β-cell function. One abnormality that occurs early in the disease progression in both type 1 and 2 diabetes is the loss of eating-induced rapid insulin response. Consequently, the liver continues to produce glucose, which adds to the glucose that is ingested and absorbed from the basic components of a meal.

Type 2 diabetics typically exhibit a delayed response to increases in blood glucose levels. While normal individuals usually begin to release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels). Another characteristic of type 2 diabetes is impaired insulin action, termed insulin resistance. Insulin resistance manifests itself as both a reduced maximal glucose elimination rate (GERmax) and an increased insulin concentration required to attain GERmax. Thus, to handle a given glucose load more insulin is required and that increased insulin concentration must be maintained for a longer period of time. Consequently, the diabetic patient is also exposed to elevated glucose concentrations for prolonged periods of time, which further exacerbates insulin resistance. Additionally, prolonged elevated blood glucose levels are themselves toxic to β cells.

Type 1 diabetes occurs as a result of the destruction of the insulin-producing cells of the pancreas (β-cells) by the body's own immune system. This ultimately results in a complete insulin hormone deficiency. Type 2 diabetes arises from different and less well understood circumstances. The early loss of early phase insulin release, and consequent continual glucose release, contributes to elevated glucose concentrations. High glucose levels promote insulin resistance, and insulin resistance generates prolonged elevations of serum glucose concentration. This situation can lead to a self-amplifying cycle in which ever greater concentrations of insulin are less effective at controlling blood glucose levels. Moreover, as noted above, elevated glucose levels are toxic to the β-cells, reducing the number of functional β-cells. Genetic defects impairing the growth or maintenance of the microvasculature nourishing the islets can also play a role in their deterioration (Clee, S. M., et al. *Nature Genetics* 38:688-693, 2006). Eventually, the pancreas becomes overwhelmed, and individuals progress to develop insulin deficiency similar to people with type 1 diabetes.

Therapy

Insulin therapy is the standard treatment for type 1 diabetes. While incipient type 2 diabetes can be treated with diet and exercise, most early stage type 2 diabetics are currently treated with oral antidiabetic agents, but with limited success. Patients generally transition to insulin therapy as the disease progresses. These treatments, however, do not represent a cure.

In a typical progression the first oral antidiabetic agent used is metformin, a supressor of hepatic glucose output. Use of metformin is not associated with weight gain or hypoglycemia. If metformin treatment is insufficient to control hyperglycemia, an insulin secretagogue, most typically a sulfonylurea, can be added to the treatment regimen. Secretagogues raise the basal level of insulin in order to lower average blood glucose levels. Use of sulphonylureas is associated with weight gain and can lead to hypoglycemia, although severe hypoglycemia is infrequent. If this combination of two oral antidiabetic agents is inadequate to control hyperglycemia either a third oral agent, such as a glitazone, or a long-acting, basal insulin can be added to the regimen. As the disease progresses, insulin therapy can be intensified by the addition of intermediate and short (rapid) acting insulin preparations administered in association with at least some of the day's meals.

Current insulin therapy modalities can supplement or replace endogenously-produced insulin to provide basal and second-phase-like profiles but do not mimic early-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., *N Engl J Med* 353:2643-53, 2005), but many patients are reluctant to accept the additional injections. Use of these conventional insulin preparations is associated with weight gain and a significant risk of hypoglycemia including severe, life-threatening hypoglycemic events.

Until recently, subcutaneous (SC) injection has been the only route of delivering insulin for self-administration by patients commercially available. However, SC insulin administration does not lead to optimal pharmacodynamics for the administered insulin. Absorption into the blood (even with rapid acting insulin analogues) does not mimic the prandial physiologic insulin secretion pattern of a rapid spike in serum insulin concentration. Subcutaneous injections are also rarely ideal in providing insulin to type 2 diabetics and may actually worsen insulin action because of delayed, variable and slow rate of absorption into the bloodstream. It has been shown, however, that if insulin is administered intravenously with a meal, early stage type 2 diabetics experience the shutdown of hepatic glucose release and exhibit increased physiologic glucose control. In addition their free fatty acids levels fall at a faster rate than without insulin therapy. While possibly effective in treating type 2 diabetes, intravenous administration of insulin is not a reasonable solution, as it is not safe or feasible for patients to intravenously administer insulin at every meal.

For a short period of time there was an inhalable insulin, EXUBERA® (Pfizer), which was marketed for the treatment of diabetes. This insulin preparation had a pharmacokinetic profile similar to the injectable rapid acting analogues and was used as a substitute for short acting insulin in the standard treatment paradigm. While this insulin preparation did allow patients using short acting insulins to avoid injections, it offered no other notable advantage which contributed to its commercial failure. Moreover, because its kinetic profile was so similar to subcutaneously administered regular and rapid-acting insulins, that after accounting for differences in bioavailability, its dosing and modes of administration could generally follow that of those subcutaneous insulins.

Though not yet commercially available, an ultrarapid acting insulin, insulin-fumaryl diketopiperazine (FDKP) has been under development. Growing experience with the use of this insulin formulation in human studies is showing that its unique kinetic profile can accommodate different dosing schemes and modes of administration as its use is applied to various situations and patient populations in order to achieve improved glycemic control. Such methods are the object of the present disclosure.

SUMMARY OF THE INVENTION

Embodiments disclosed herein include methods useful for treating diabetes mellitus including both type 1 and type 2 using an ultrarapid acting insulin formulation. The disclosed methods relate to procedures for determining dosages, the use of standard dosages that are not adjusted from individual meal to meal, the use of split dosages wherein the insulin formulation is administered at the beginning of the meal and at a subsequent point in time. In certain embodiments, the insulin formulation is insulin-FDKP and is administered by pulmonary inhalation. Such formulations can be advantageously used in the treatment of patients with subcutaneous insulin resistance, and methods of selecting such patients are also disclosed herein.

Embodiments of the method include administration of insulin in a manner that mimics the meal-related early phase insulin response. In mimicking early phase kinetics peak serum insulin levels can be reached within about 12 to within about 30 minutes of administration. Serum insulin levels can also return to approach baseline within about two or three hours of administration. Insulin preparations mimicking early phase kinetics in this manner are referred to herein as ultrarapid acting insulins. In one embodiment a dose sufficient to reduce or control glucose excursions is used. In one embodiment, insulin is administered to a patient in need of insulin therapy at mealtime, that is, within about 10 minutes, preferably 5 minutes before, or 30, 25, 15, or 10 minutes after starting a meal. (The shorter times after starting being preferred for patients with normal gastric emptying, the longer times after starting being appropriate for patients with delayed gastric emptying). In further embodiments, insulin is administered at least twice, initially at the beginning of the meal (that is within 10 minutes plus or minus of starting a meal) and a second time such as 30-120 minutes after beginning the meal.

In preferred embodiments, a pulmonary delivery is achieved by inhalation of a dry powder formulation comprising fumaryl diketopiperazine (FDKP) associated with insulin. In such usage the term "fumaryl diketopiperazine" as used herein also includes the salts thereof. One such embodiment comprises insulin and an FDKP salt. In another such embodiment insulin is complexed with FDKP. For example insulin may be complexed (bound) to the surface of self-assembled crystalline FDKP microparticles, referred to herein generically as "insulin-FDKP", but also as TECHNOSPHERE® insulin (TI, MannKind Corp.). In other embodiments, FDKP is replaced by other C-substituted diketopiperazines, for example 3,6-di(succinyl-4-aminobutyl)-2,5-diketopiperazine ("succinyl diketopiperazine", SDKP). In an aspect of these embodiments delivery is facilitated by use of a unit dose inhaler such as the MEDTONE® inhaler system (MannKind Corp.) utilized in the examples below and described in U.S. Pat. Nos. 7,305,986 and 7,464,706 which are incorporated herein by reference in their entirety. Preferred dosages, based on fill for this system, are in the range of about 7.5 IU to 120 IU, particularly 15 to 90 IU, or greater than 24 IU of insulin complexed with fumaryl diketopiperazine, or the equivalent. Dosages can also be expressed as the dose emitted from the inhaler. These doses are preferably in the range of 6 U to 48 U per inhaler cartridge for patient dosages of 6 U to 72 or 96 U. As explained below dosages can be more universally expressed in subcutaneous equivalent (subQ eq) units. In these units preferred dosages are in the range of 1-32 or more units, for example 3, 6, 9 . . . or 4, 8, 12 . . . subQ eq units. For example with an alternative inhaler system as described in U.S. patent application Ser. Nos. 12/484,125, 12/484,129, and 12/484,137, dosages of 3-4 subQ eq units are obtained with cartridges filled with 20-22 IU.

In an embodiment, the insulin dose comprises a dose sufficient to control glucose excursions. In another embodiment, the insulin reaches peak serum levels within about 15 minutes of administration. In another embodiment, the peak serum insulin level is at least 60 mU/L. In still another embodiment, the peak serum insulin concentration is at least 60, 100, or 120 mU/L above the pre-dosing insulin concentration baseline. In one aspect of this embodiment, the recipient has type 2 diabetes. In another embodiment, the insulin dose is sufficient to control blood glucose levels. In yet another embodiment, the insulin dose is sufficient to reduce or suppress glucose release from the liver. In one aspect of this embodiment, the suppression lasts several hours (see FIG. 5). In one aspect of this embodiment a nadir in endogenous glucose production is reached more quickly than following subcutaneous administration of regular insulin or a rapid-acting insulin analogue, preferably in ≦60 minutes, more preferably in ≦50 minutes, still more preferably in about 40 minutes. In still another embodiment the dose is sufficient to maximally suppress endogenous glucose production.

Additional embodiments provide methods for improved treatment of patients with diabetes comprising selecting a patient in need of improved glycemic control, discontinuing current treatment, and routinely administering an ultrarapid acting insulin with at least two meals each day.

In other embodiments, the need for improved glycemic control is determined from HbA1c levels. In one embodiment, the level of serum HbA1c is ≧8%. In yet other embodiments, the level of serum HbA1c is ≧7.5%, ≧7.0%, ≧6.5%, or ≧6.0%. In other embodiments, the need for improved glycemic control is determined from elevated mean amplitude of glucose excursions or elevated post prandial blood glucose levels. In yet another embodiment, the patient has evidence of elevated oxidative stress and the oxidative stress is measured by 8-iso PGF(2a) levels. Elevated oxidative stress is correlated with elevated mean amplitude of glucose excursions.

In one aspect of these embodiments, the patient is further in need of avoiding weight gain, and treatment with the ultrarapid acting insulin does not result in weight gain or as much weight gain as expected from another mode of treatment. In a related embodiment, the patient is obese and/or in need of losing weight and treatment with the ultrarapid acting insulin results in weight loss, stable weight, or less weight gain as expected from another mode of treatment. Such embodiments can further comprise a step for assessing weight loss or less than otherwise expected weight gain. In one aspect of the invention the assessment is conducted at ≧12 weeks of treatment with meal-time ultrarapid acting insulin. In another aspect the assessment is conducted at ≧24 weeks. In yet other aspects the assessment is conducted at ≧36 week or ≧48 weeks.

In various embodiments, the method further comprises assessment of an improvement in glycemic control. In one embodiment, glycemic control is assessed as HbA1c level. In another embodiment, glycemic control is assessed as postprandial glucose excursion. In one aspect postprandial glucose excursion is assessed as postprandial blood glucose level. In another aspect it is assessed as oxidative stress, e.g. as 8-iso PGF(2a) levels or other indicators known in the art. In another embodiment, glycemic control is assessed as fasting blood glucose. In further embodiments, these factors are assessed in various combinations. In one aspect of embodiments, the assessment is conducted at ≧12 weeks of treatment with meal-time ultrarapid acting insulin. In another aspect, the assessment is conducted at ≧24 weeks. In yet other aspects the assessment is conducted at ≧36 week or ≧48 weeks.

In one embodiment, ultrarapid acting insulin is routinely administered with at least two meals each day. In another embodiment, ultrarapid acting insulin is administered with at least three meals each day. In another embodiment, ultrarapid acting insulin is administered with each main or substantive meal each day. In another embodiment, the ultrarapid acting insulin is administered with any meal containing more than 15 g of carbohydrate.

Some embodiments comprise modifying a current standard of care treatment regimen for diabetes by substituting prandial administration of an ultrarapid acting insulin preparation for one or another of the advocated treatments.

One embodiment provides methods for more effectively combining an ultrarapid acting insulin with a long acting insulin analog, for example insulin glargine. In this embodiment prandial administration of the ultrarapid acting insulin is combined with a morning dose of a long acting insulin analog administered within 6 hours of waking for a day. In aspects if this embodiment the long acting insulin analog dose is administered within 1, 2, 3, or 4 hours of waking. In one aspect of this embodiment the long acting insulin analog is insulin glargine. In another aspect of this embodiment the long acting insulin analog is insulin detemir. In related aspects the long acting insulin analog is insulin glargine and a second dose is administered from 8 to 14 hours after the morning dose. Alternatively the first dose is the only dose administered in the course of the day. In still another embodiment instead of using injections of a long acting insulin, an insulin pump is used to provide a continuous infusion of an insulin, for example regular human insulin. In one embodiment the ultrarapid acting insulin formulation comprises insulin and a diketopiperazine. In a particular embodiment the ultrarapid acting insulin formulation comprises insulin-FDKP.

Some embodiments comprise modifying a current standard of care treatment regimen for type 2 diabetes by substituting prandial administration of an ultrarapid acting insulin for treatment with an insulin secretagogue. Other embodiments comprise modifying a current standard of care treatment regimen for type 2 diabetes by substituting prandial administration of an ultrarapid acting insulin for treatment with an insulin sensitizer. Still other embodiments comprise modifying a current standard of care treatment regimen for type 2 diabetes by substituting prandial administration of an ultrarapid acting insulin for treatment with both an insulin secretagogue and an insulin sensitizer.

In one embodiment disclosed herein, a method is provided for treating diabetes type 2, comprising: selecting a patient with diabetes type 2 currently being treated with a suppressor of hepatic glucose output and an insulin secretagogue; discontinuing treatment with the insulin secretagogue; and routinely administering an ultrarapid acting insulin preparation with at least one established meal. In another embodiment, treatment with the suppressor of hepatic glucose output is also discontinued.

In another embodiment, the patient is further selected for having an insulin resistance at the lower portion of the insulin resistance spectrum. In yet another embodiment, the patient is further selected for needing to reduce or avoid weight gain. In yet another embodiment, the patient is further selected for having well or moderately controlled fasting blood glucose. In yet another embodiment, the patient is further selected for having an HbA1c level ≧8. In yet another embodiment, the patient is further selected for having an elevated mean amplitude of glucose excursions In yet another embodiment, the administering step does not comprise an injection and wherein patient is further a candidate for treatment with insulin and is further selected on the basis of being needle-phobic or desiring to avoid frequent injections.

In another embodiment, the suppressor of hepatic glucose output is metformin and the insulin secretagogue is a sulfonylurea. In one embodiment, the ultrarapid acting insulin preparation is administered by inhalation, such as a dry powder. In another embodiment, the ultrarapid acting insulin preparation comprises a fumaryl diketopiperazine (FDKP) associated with insulin such as insulin-FDKP.

In another embodiment, the ultrarapid acting insulin preparation is administered with each meal containing more than 15 g of carbohydrate. In another embodiment, ultrarapid acting insulin preparation is administered at a dosage sufficient to maximally reduce hepatic glucose output within 60 minutes of administration. In another embodiment, the ultrarapid acting insulin preparation is administered at a dosage within the range of 1 to 32 subcutaneous equivalent units.

In one embodiment, provided herein is a method of treating diabetes type 2, comprising: selecting a patient with diabetes type 2 currently being treated with a suppressor of hepatic glucose output who is in need of improved glycemic control and who would be a candidate for combination treatment with said suppressor of hepatic glucose output and an insulin secretagogue; and instead combining treatment with said suppressor of hepatic glucose output with routinely administering an ultrarapid acting insulin preparation with at least one established meal.

In one embodiment provided herein is a method of treating diabetes type 2, comprising: selecting a patient with diabetes type 2 currently being treated with an insulin sensitizer and an insulin secretagogue; discontinuing treatment with the insulin secretagogue; and routinely administering an ultrarapid insulin preparation with each meal. In another embodiment, treatment with the insulin sensitizer is also discontinued. In yet another embodiment, the patient is further selected for having an insulin resistance at the higher portion of the insulin resistance spectrum. In another embodiment, the insulin sensitizer is a thiazolidinedione (TZD) such as pioglitazone.

In one embodiment, provided herein is an improved method of treating hyperglycemia with a combination of an ultrarapid acting insulin and a long acting insulin analog comprising: prandial administration of the ultrarapid insulin, and administration of a dose of the long-acting insulin analog within 6 hours of waking for a day. In another embodiment, the hyperglycemia is resultant of diabetes type 2. In another embodiment, the administration of the long acting insulin analog is within 3 hours of waking. In another embodiment, the long acting insulin analog is insulin detemir or insulin glargine. In yet another embodiment, the long acting insulin is insulin glargine and the method further comprises administering a second dose of insulin glargine and the second dose is administered from 8 to 14 hours after said morning dose.

In another embodiment, the ultrarapid acting insulin comprises a formulation comprising insulin and a diketopiperazine, such as insulin-FDKP. In another embodiment, the ultrarapid acting insulin is administered by inhalation into the lungs.

In one embodiment, provided herein is an improved method of treating hyperglycemia with a combination of an ultrarapid acting insulin and an exogenous basal insulin comprising: prandial administration of the ultrarapid insulin, and continuous infusion of a short acting insulin with an insulin pump. In another embodiment, the short-acting insulin is regular human insulin or a rapid acting insulin analog. In another embodiment, the ultrarapid-acting insulin formulation is insulin-FDKP.

In one embodiment, provided herein is a method of controlling glycemia related to a daily meal without adjusting an insulin dose for meal content comprising the step of administering a predetermined dosage of an ultrarapid acting insulin formulation at mealtime for each daily meal. In another embodiment, the meal content is ≧25%, ≧50%, ≦150%, or ≦200% of a usual meal content as used in determination of the predetermined dose.

In one embodiment, provided herein is a method of controlling glycemia related to a daily meal for a patient with delayed or prolonged nutrient absorption comprising the steps of: selecting a patient with delayed nutrient absorption;

administering 50% to 75% of a predetermined dosage of an ultrarapid-acting insulin formulation at mealtime for the daily meal; and administering the remainder of the predetermined dosage 30 to 120 minutes after beginning the daily meal. In another embodiment, the ultrarapid acting insulin formulation is insulin-FDKP.

In another embodiment, the delayed nutrient absorption is related to a disease state. In yet another embodiment, the delayed nutrient absorption is related to a meal content high in fat or fiber. In yet another embodiment, the prolonged nutrient absorption is related to a prolonged meal.

In one embodiment, provided herein is a method of controlling glycemia related to a daily meal wherein insulin dosage is adjusted to the glycemic load of the meal consumed comprising the steps of: administering an initial predetermined dose of an ultrarapid acting insulin formulation at mealtime for the daily meal; determining postprandial blood glucose 1 to 2 hours after beginning the daily meal; and if the postprandial blood glucose is >140 mg/dl administering a second dose of the ultra rapid acting insulin formulation wherein the second dose is 25% to 100% of the initial dose. In another embodiment, the ultrarapid acting insulin formulation is insulin-FDKP.

In one embodiment, provided herein is a method of treating diabetics with subcutaneous insulin resistance comprising the steps of: selecting a patient with subcutaneous insulin resistance on the basis of atypically high insulin dosage; discontinuing treatment with subcutaneously administered rapid-, short-, or intermediate-acting insulin formulations; and initiating treatment by administration of prandial doses of insulin-FDKP by inhalation effective for the control of postprandial hypoglycemia.

In another embodiment, the atypically high insulin dosage is ≧2 units/Kg/day. In another embodiment, the selecting step further comprises selection of the basis that the patient has normal or near-normal levels of endogenous basal insulin. In yet another embodiment, the level of endogenous basal insulin is ≦50 μU/ml.

In another embodiment, the selecting step further comprises one of the following: selection on the basis of injection site lipoatrophy or lipodystrophy; selection of the basis of the patient having 2 HbA1c level determinations ≧9% in a 6 to 9 month period while on an intensified insulin regimen; or selection of the basis of the patient having life threatening glycemic instability characterized by periods of hyperglycemia and/or hypoglycemia despite adherence to their insulin regimen and any diet or exercise regimen.

In another embodiment, the method further comprises the step of confirming the patient has subcutaneous insulin resistance by determining that a similar or improved degree of glycemic control is achieved with a substantially lower dosage of insulin after adjustment based on relative bioavailability.

In one embodiment, provided herein is a method for determining an individual's dosage of an ultrarapid acting insulin for a daily meal comprising the steps of: administering a low dose of the ultrarapid acting insulin at mealtime for the daily meal for which the dosage is being titrated each day for at least 3 days within a titration period of not more than a week; iteratively increasing the dosage by the amount of the low dose in each subsequent titration period and administering at mealtime for the daily meal for which the dosage is being titrated each of at least three days in the titration period until a titration endpoint is reached.

In another embodiment, the low dose is provided in a unit dose cartridge. In another embodiment, titration period is 3 days or one week. In another embodiment, the low dose is 1-5 subQ eq units. In another embodiment, the ultrarapid acting insulin formulation is insulin-FDKP.

In another embodiment, the titration endpoint is selected from: 1) achieving a 2-hour post-prandial median glucose is between 70 and 110 mg/dl, 2) the dosage based on subcutaneous equivalent (subQ eq) units is a maximal dosage, 3) an episode of severe hypoglycemia with a confirmed SMBG <36 mg/dl occurs and the dosage is decreased by the equivalent of one low-dose cartridge, and 4) an episode of mild to moderate hypoglycemia with a confirmed SMBG of <70 mg/dl occurs, the dosage is decreased by the equivalent of one low dose cartridge for one week and then the titration is resumed until it reaches any of said endpoints 1-3 or the dosage is set at the level below that which again produces the mild to moderate hypoglycemia.

In another embodiment, the dosages for two or more daily meals are titrated concurrently. In another embodiment the dosages for two or more daily meals are titrated successively from the daily meal resulting in the highest 2-hour postprandial blood glucose to the daily meal resulting in the lowest 2-hour postprandial blood glucose.

In another embodiment, the maximal dosage is 24 subQ eq units or 2 subQ eq units.

BRIEF DESCRIPTION OF THE DRAWINGS

FIG. 16 depicts the baseline demographics of patients enrolled in the study of FIG. 15.

DEFINITION OF TERMS

Figure 1:
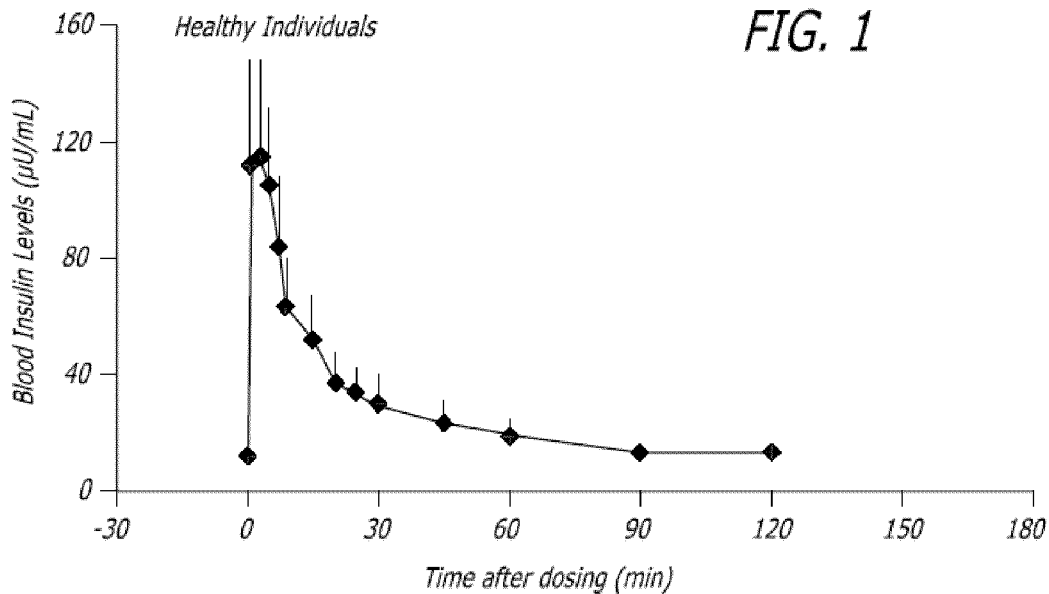
FIG. 1 depicts the measurement of first-phase insulin release kinetics following artificial stimulation by bolus glucose infusion.
Figure 2:
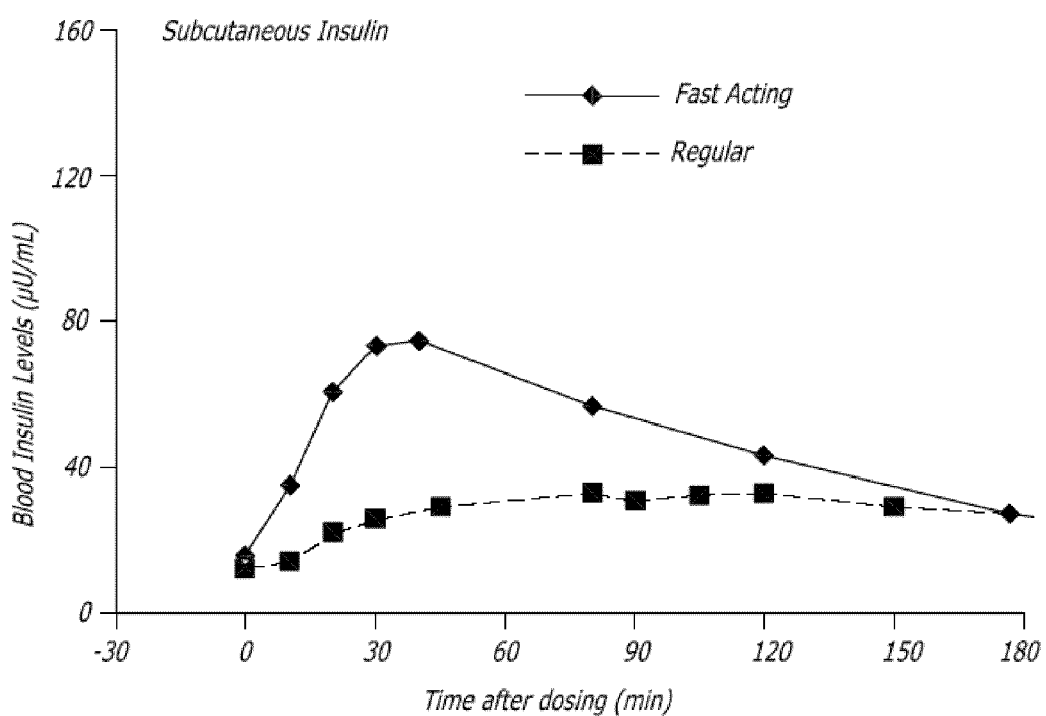
FIG. 2 depicts serum insulin concentration after administration of subcutaneous (SC) regular human insulin or SC fast acting insulin (NOVOLOG™). NOVOLOG™ is a registered trademark of Novo Nordisk Pharmaceuticals, Bagsvaerd, Denmark.

Prior to setting forth the detailed disclosure, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

First-Phase: As used herein, "first-phase" refers to the spike in insulin levels as induced by a bolus intravenous injection of glucose. A first-phase insulin release generates a spike in blood insulin concentration that is a rapid peak which then decays relatively quickly.

Early phase: As used herein "early phase" refers to the rise in blood insulin concentration induced in response to a meal which peaks within 20-30 minutes. The distinction between early phase and first phase is not always carefully adhered to in the general literature.

Excursion: As used herein, "excursion" refers to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

Glucose elimination rate: As used herein, "glucose elimination rate" (GER) is the rate at which glucose disappears from the blood. Using a glucose clamp it can be determined as the glucose infusion rate required to maintain stable blood glucose, often around 120 mg/dL during a glucose clamp experimental procedure. This glucose elimination rate is equal to the glucose infusion rate, abbreviated as GIR.

Honeymoon phase: As used herein, the "honeymoon phase" of type 1 diabetes refers to the early stages of the disease characterized by loss of early phase insulin release and the remaining β-cell function produces some insulin, which is released with second-phase kinetics.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL (3.5 mM). Clinically relevant hypoglycemia is defined as blood glucose concentration below 63 mg/dL or causing patient symptoms such as cognitive impairment, behavioral changes, pallor, diaphoresis hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal.

Insulin composition: As used herein, "insulin composition" refers to any form of insulin suitable for administration to a mammal and includes insulin isolated from mammals, recombinant insulin, insulin associated or derivatized with other molecules, and insulin molecules with altered sequences, so long as they retain clinically relevant blood glucose lowering activity. Also included are compositions of insulin suitable for administration by any route including pulmonary, subcutaneous, nasal, oral, buccal and sublingual. Insulin compositions can be formulated as dry powders, aqueous solutions or suspensions, or non-aqueous solutions or suspensions (as is typical for metered dose inhalers) for inhalation; aqueous solutions or suspensions for subcutaneous, sublingual, buccal, nasal or oral administration; and solid dosage forms for oral and sublingual administration.

Insulin-related disorder: As used herein, "insulin-related disorders" refers to disorders involving production, regulation, metabolism, and action of insulin in a mammal. Insulin-related disorders include, but are not limited to, pre-diabetes, type 1 diabetes mellitus, type 2 diabetes mellitus, hypoglycemia, hyperglycemia, insulin resistance, secretory dysfunction, loss of pancreatic β-cell function, and loss of pancreatic β-cells.

Non-insulin dependent patients having insulin-related disorders: As used herein "non-insulin dependent patients having insulin-related disorders" refers to patients with disorders for which therapy with exogenously-provided insulin is not the current standard treatment upon diagnosis. Non-insulin dependent patients having insulin-related disorders which are not treated with exogenously-administered insulin include early type 2 diabetes, type 1 diabetes in the honeymoon phase, pre-diabetes and insulin-producing cell transplant recipients.

Insulin resistance: As used herein, the term "insulin resistance" refers to the inability of a patient's cells to respond to insulin appropriately or efficiently. The pancreas responds to this problem at the cellular level by producing more insulin. Eventually, the pancreas cannot keep up with the body's need for insulin and excess glucose builds up in the bloodstream. Patients with insulin resistance often have high levels of blood glucose and high levels of insulin circulating in their blood at the same time.

Insulin resistance spectrum: As used herein "insulin resistance spectrum" refers to the range over which the degree to which a patient is resistant to insulin can vary. It is well understood that from person to person, and from one point in the progression of type 2 diabetes to another the degree of insulin resistance can differ. Although there are no generally accepted units of insulin resistance it is well within the ability of one of ordinary skill in the art to recognize a lower degree of insulin resistance as opposed to a higher degree of insulin resistance. Ideally insulin resistance can be measured with euglycemic clamp procedures, but these are not practical for routine use. Simpler assessments include HOMA (see Matthew D R, Hosker J P, Rudenski A S, et al., Homeostasis model assessment: insulin resistance and β-cell function from fasting plasma glucose and insulin concentrations in man, *Diabetologia* 1985;28:412-419) and the related QUICKI (Katz A, Nambi S S, Mather K, Baron A D, Follmann D A, Sullivan G, Quon M J. Quantitative insulin sensitivity check index: a simple, accurate method for assessing insulin sensitivity in humans. *J Clin Endocrinol Metab.* 2000 Jul; 85(7): 2402-10). Fasting serum insulin levels themselves can also be used as an indicator of the degree of insulin resistance with concentrations of 50-100 pmol/L indicating resistance at the lower end of the spectrum and concentrations of 300 pmol/L indicating resistance at the higher end of the spectrum. Finally, for patients already on an insulin treatment, the total daily dose is commonly taken as an indicator of whether the subject has a high or low degree of insulin resistance.

Intermediate acting insulin: As used herein, "intermediate acting insulin" or lente insulin, refers to an insulin with an onset of action usually about two to four hours after injection and peaks four to 12 hours after injection, and it keeps working for 10 to 18 hours. Typical intermediate acting insulins are obtained by mixing regular insulin with a substance that makes the body absorb the insulin more slowly. A non-limiting example is NPH insulin. Intermediate acting insulin can provide many of the benefits of long acting insulin.

Long acting insulin: As used herein, the term "long acting insulin" refers to an insulin formulation that starts working within about 1-6 hours and provides a continuous level of insulin activity for up to 24 hours or more. Long-acting insulin operates at maximum strength after about 8-12 hours, sometimes longer. Long-acting insulin is usually administered in the morning or before bed. Non-limiting examples of long acting insulin include, but are not limited to, insulin glargine or insulin detemir, which are insulin analogs, and ultralente insulin which is regular human insulin formulated to slow absorption. Long acting insulin is best suited to provide for basal, as opposed to prandial, insulin requirements.

Meal: As used herein, "meal", "meals", and/or "mealtime", etc. include traditional meals and meal times; however, these also include the ingestion of any sustenance regardless of size and/or timing. As used herein "established meal" refers specifically to the daily periods of primary food consumption such as the usual or traditional three daily meals. Some diabetics are encouraged to eat four somewhat smaller daily meals to reduce peak blood glucose levels; such meals are also included within the meaning of the term established meal.

Microparticles: As used herein, the term "microparticles" includes microcapsules having an outer shell composed of either a diketopiperazine alone or a combination of a diketopiperazine and one or more drugs. It also includes microspheres containing drug dispersed throughout the sphere; particles of irregular shape; and particles in which the drug is coated on the surface(s) of the particle or fills voids therein.

Prandial: As used herein, "prandial" relates something to a meal or a snack. Depending on context in can refer to a period of time less than an hour after beginning a meal, or for as long as consumption of food continues.

Periprandial: As used herein, "periprandial" refers to a period of time starting shortly before and ending shortly after the ingestion of a meal or snack.

Postprandial: As used herein, "postprandial" refers to a period of time, generally an hour or more, after beginning a meal and after ingestion of a meal is completed. As used herein, late postprandial refers to a period of time beyond 2 hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Pre-Diabetic: As used herein, the term "pre-diabetic" refers to a patient with impaired fasting glucose impaired glucose tolerance, that is with a fasting blood glucose level between 100 mg/dL (5.5 mmol/L) and 126 mg/dL (7.0 mmol/L), or a 2 hour post-prandial blood glucose level between 140 mg/dL (7.8 mmol/L) and 200 mg/dL (11.1 mmol/L).

Rapid acting insulin: As used herein, the term "rapid acting insulin" refers to an insulin formulation that reaches peak blood concentration in approximately 45-90 minutes and peak activity approximately one to 3 hours after administration. Rapid acting insulin can remain active for about four to six hours. A non-limiting example of a rapid acting insulin is the insulin analog insulin lispro (HUMALOG®). The withdrawn product EXUBERA® and the experimental formulation VIAJECT® (Biodel Inc.), both based on regular human insulin, have kinetic profiles falling within this definition.

Second-Phase: As used herein, "second-phase" refers to the non-spiking release of insulin in response to elevated blood glucose levels. This is distinct from "second-phase kinetics" which refers to the slow decay of modestly elevated blood insulin levels back to baseline.

Short acting insulin: As used herein the term "short acting insulin" includes regular insulin and the rapid acting preparations, typically used around mealtimes.

Snack: As used herein "snack" refers specifically to food consumed between established meals.

Suppressor of hepatic glucose output: As used herein, the phrase "suppressor of hepatic glucose output" refers to drugs which suppress hepatic glucose production (hepatic gluconeogenesis, mobilization from glycogen stores). A non-limiting example of a suppressor of hepatic glucose output is metformin.

TECHNOSPHERE® Insulin: As used herein, "TECHNOSPHERE® Insulin" or "TI" refers to an insulin composition comprising regular human insulin and TECHNOSPHERE® microparticles, a drug delivery system. TECHNOSPHERE® microparticles comprise a diketopiperazine, specifically 3,6-di(fumaryl-4-aminobutyl)-2,5-diketopiperazine (fumaryl diketopiperazine, FDKP). Specifically, TECHNOSPHERE® Insulin comprises a FDKP/human insulin composition. TECHNOSPHERE® Insulin is an ultrarapid acting insulin as delivered by pulmonary administration and mimics physiologic mealtime early phase insulin release. This formulation is also referred to generically herein as "insulin-FDKP". In some contexts the product is referred to as insulin monomer human [rDNA origin] inhalation powder.

As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

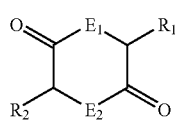

Formula 1

Diketopiperazine microparticles, in addition to making aerodynamically suitable microparticles enabling delivery to the deep lung, also rapidly dissolve and release any drug cargo further speeding absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In another embodiment of the present invention, the DKP is a derivative of 3,6-di(4-aminobutyl)-2,5-diketopiperazine, which can be formed by (thermal) condensation of the amino acid lysine. Exemplary derivatives include 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5, 352,461, 5,503, 852, 6,071,497, and 6,331,318, each of which is incorporated herein by reference for all that it teaches regarding diketopiperazines and diketopiperazine-mediated drug delivery). The use of DKP salts is described in co-pending U.S. patent application Ser. No. 11/210,710 filed Aug. 23, 2005, which is hereby incorporated by reference for all it teaches regarding diketopiperazine salts. Pulmonary drug delivery using DKP microparticles is disclosed in U.S. Pat. No.6,428,771, which is hereby incorporated by reference in its entirety.

TECHNOSPHERE®/Placebo: As used herein, "TECHNOSPHERE®/Placebo" refers to TECHNOSPHERE® particles which are not associated with insulin or other active agent.

Tmax: As used herein, the term "Tmax" refers to the time from administration for a parameter (such as concentration or activity) to reach its maximum value.

Units of measure: Subcutaneous and intravenous insulin dosages are expressed in IU which is defined by a standardized biologic measurement. Amounts of insulin formulated with fumaryl diketopiperazine are also reported in IU as are measurements of insulin in the blood. TECHNOSPHERE®/Insulin dosages are expressed in arbitrary units (U) which are numerically equivalent to the amount of insulin formulated in the dosage.

DETAILED DESCRIPTION OF THE INVENTION

Insulin-FDKP was discovered to be an ultrarapid acting insulin capable of mimicking physiologic mealtime early phase insulin release. In exploring how an insulin preparation with this unique pharmacokinetic profile might be used advantageously in the treatment of type 2 diabetes, it has up to now been evaluated in comparison to other insulin preparations (see for example U.S. patent application Ser. Nos. 11/032,278, 11/329,686, 11/278,381, and 11/461,746, each of which are hereby incorporated by reference in their entirety). Embodiments disclosed herein are concerned with how specific dosages and modes of administration for such insulin preparations can be chosen for individual patients and applied to various patient populations for advantageous effect. Certain embodiments are concerned with how such insulin preparations can be used in combination with and/or in place of oral antidiabetic medications, particularly insulin sensitizers and insulin secretagogues, to achieve similar or advantageous effect. Certain other embodiments are concerned with how such insulin preparations can be used in combination with and/or in place of exogenously provided basal insulins to achieve similar or advantageous effect. Similar disclosure is also found in U.S. Provisional patent application Nos. 61/087,943, 61/097,495, 61/097,516, and 61/138,863, each of which is incorporated herein by reference in its entirety.

In general, various embodiments involve the use of prandial ultrarapid acting insulin in defined populations. These populations may be referred to as being in need of, capable of benefiting from, or desirous of receiving the benefit of one or another or more of the advantages offered by the various methods described. Such advantages can be expressed as receiving or seeking some stated clinical benefit. Such advantages can also include elimination or avoidance of various side-effects, adverse outcomes, contraindications, and the like, or reducing the risk or potential for them to occur. Similarly the methods can involve a step of selecting a patient on the basis of being part of one or another of populations. It should be understood that selecting can comprise a physician or other healthcare professional evaluating a patient in respect to the particular parameters but can also comprise a self-selection by the patient to be treated on the basis of similar data or in accepting the advice of the physician or other healthcare professional. In like manner, administering steps of these methods can comprise the physical taking of a medicament (or similarly discontinuing treatment with a medicament) by a patient but can also comprise a physician or other healthcare professional prescribing or providing other specific instruction to take (or discontinue) a medicament. Further embodiments of the invention include use of ultrarapid acting insulin preparations, compositions, or formulations for such purposes, and in the manufacture of medicaments for such purposes.

As used herein, mimicking physiologic mealtime early phase insulin release (or similar terms) does not necessarily indicate exact replication of all features of the physiologic response. It can refer to insulin preparations and methodologies producing a spike or peak of insulin concentration in the blood that constitutes both a relatively quick rise and fall in concentration. In certain embodiments, the rise to peak concentration takes less than 30 minutes, preferably less than about 20 minutes or 15 minutes and in further embodiments takes at least 5 or at least 10 minutes to peak; for example reaching a peak concentration in 12-14 minutes or 10-20 minutes, etc., from administration or first departure from baseline. In certain embodiments the fall from the peak insulin concentration involves descent through half maximal by 80 minutes, alternatively 50 minutes, or alternatively 35 minutes after peak. Typically insulin concentration will be approaching baseline with 2 to 3 hours of administration. This is in contrast to insulin preparations and methods producing a more gradual rise (from 30 minutes to several hours) to the maximal insulin concentration achieved and a prolonged plateau near maximal concentrations. The rapid acting analogs (RAA) do show a greater degree of peaking that regular human insulin, but even the fastest of the commercially available RAAs, as disclosed in their prescribing information, insulin lispro (HUMALOG®) reports a Tmax of 30-90 minutes. For comparison, insulin aspart (NOVOLOG®) reports a median Tmax of 40-50 minutes in subjects with type 1 diabetes and insulin glulisine (APIDRA®) reports a median Tmax of 60 and 100 minutes in subjects with type 1 and type 2 diabetes, respectively with a range of 40-120 minutes in both populations. Moreover the RAAs require approximately 6 hours for concentration to return to baseline. Mimicking physiologic mealtime early phase insulin release can also refer to insulin preparations and methodologies in which the spike in insulin concentration can be reliably coordinated with the start of a meal. It can also refer to the achievement (and associated methodologies) of a maximal glucose elimination rate (GERmax) within about 30-90 minutes, preferably around 45-60 minutes, after administration. Insulin preparations with such characteristics are referred to herein as ultrarapid acting. In embodiments of the invention a methodology that mimics early phase release is generally also one that can be practiced by diabetics upon themselves without special medical training, such as training in intravenous injection. Special medical training would not include training to use medical devices, such as dry powder inhalers, that are routinely used by persons who are not trained medical professionals. In some embodiments ultrarapid acting insulin can be administered with every ingestion of any sustenance regardless of size and/or timing. Nonetheless it is preferred that insulin be administered only for a meal providing at least a threshold glycemic load (which can depend on the insulin dose) so as to avoid a risk of hypoglycemia. Various methods of assessing glycemic load are known in the art including "carb counting" (calculating/estimating the number of grams of carbohydrate in a meal), the use of bread exchanges, and consideration of the glycemic index of the foods to be consumed.

The meaning of ultrarapid can also be understood by further comparison to other insulin preparations. Regular human insulin preparations for subcutaneous injection are considered short acting, referring primarily to their duration of action. Typically they will take at least 1-2 hours to reach maximal blood insulin concentration and can take 2-4 hours to reach maximal activity. Significant elevation or activity can last for as long as 10-12 hours. Other short acting insulins include the rapid acting insulin analogs such as insulin aspart, insulin glulisine, and insulin lispro. Because these insulin preparations more readily dissociate from hexamer to monomer upon injection they reach peak blood concentrations sooner (30-100 minutes) and consequently also have a faster onset of action than regular human insulin. Insulin preparations for pulmonary administration, such as the now withdrawn product EXUBERA® display pharmacodynamics similar to the rapid acting analogs. A comparison of the pharmacodynamic profiles of several pulmonary formulations, insulin lispro, and insulin-FDKP has been published showing that insulin-FDKP is distinctly faster in reaching maximal activity and declines toward baseline sooner (Heinemann et al. Br J Diab Dis 4:295-301, 2004). Thus, whereas an ultrarapid acting insulin will have expended approximately two thirds of its insulin lowering activity within 2 hours after administration these other preparations will typically have expended about a third or less of their insulin lowering activity in that same time frame. At the other end of the spectrum are the long acting insulins, such as insulin glargine or insulin detemir which ideally provide a constant level of insulin activity over long periods of time, for example up to 24 hours. These are intended to provide basal activity and are typically administered once or twice a day. As such the rapidity of onset of action is not a critical parameter. Finally there are insulin preparations, termed intermediate acting, with durations of action between the short and long acting products.

The potentiation of GER contributing to the rapid attainment of GERmax is understood to depend not only on the rapidity of the rise in insulin concentration, but also on achieving sufficient peak height. For type 1 diabetics this is a peak insulin concentration of at least about 60 mU/L, preferably at least about 80 mU/L. For type 2 diabetics the insulin resistance that is part of the condition can necessitate higher insulin concentrations; typically at least about 100 mU/L, preferably at least about 120 mU/L, at least about 140 mU/L, or more, depending on the degree of resistance. Thus in various embodiments the peak height is at least 60, 100, or 120 mU/L above the pre-dosing insulin concentration baseline. These peak insulin concentrations are substantially higher than those attained with typical doses of non-spiking insulin products such as standard preparations for subcutaneous administration, including those termed rapid- or fast-acting, and preparations for non-injected administration having similar kinetics that have been described.

The comparatively slow and shallow rise in insulin concentration and prolonged period of action associated with insulin preparations that do not mimic early phase release limits their ability to control glucose excursions. The dose that can be given is generally inadequate to control the rise in blood glucose following a meal due to the need to avoid inducing hypoglycemia after the glycemic load from the meal has been abated. These issues are further discussed in co-pending U.S. patent application Ser. No. 11/278,381, which is incorporated herein by reference in its entirety. It is emerging that acute fluctuations in blood glucose concentrations (measured for example as MAGE: mean amplitude of glycemic excursions) have a greater effect than chronic hyperglycemia (typically measured as Hb1Ac level) on diabetes-associated oxidative stress, and thus is an important parameter to control to avoid diabetic complications attributable to such stress (see Monnier, L., et al. *JAMA* 295:1681-1687, 2006; and Brownlee, M. & Hirsch, I. *JAMA* 295:1707-1708, which are incorporated herein by reference in their entirety). It is the applicant's further understanding that a high surge and rapid rate of change in insulin concentration suppresses glucagon production, reducing hepatic glucose release. This results in lessened glycemic load and consequently lessened demand for insulin and reduced glucose excursion.

Ultrarapid acting insulin is particularly well suited to the control of postprandial blood glucose (PPG). (For a review of the significance of PPG see MannKind Corporation. *Postprandial hyperglycemia: Clinical significance, pathogenesis, and treatment*. Valencia, Calif.: MannKind Corporation; 2009:1-20). The ultrarapid kinetics not only enable better matching of insulin activity to the time when glucose is being absorbed from a meal, there is also similarly quicker and advantageously timed suppression of hepatic glucose output (see Example 1). Thus it addresses both sources of glucose contributing to postprandial hyperglycemia. Embodiments disclosed herein seek to constrain 1 and 2 hour PPG to $\leq 140$ mg/dl, $\leq 180$ mg/dl, or $\leq 200$ mg/dl. Surprisingly, it has also become apparent that control of PPG levels has long term beneficial effects on fasting blood glucose levels as well. Through consideration of these properties and the data from clinical use presented in the Examples below, it is herein disclosed how ultrarapid acting insulins such as insulin-FDKP may be advantageously used in particular patient populations alone or in combination with standard oral antidiabetic medications and in contrast to current treatment paradigms.

Treatment of diabetes has traditionally focused on controlling average blood glucose concentrations, as reflected by Hb1Ac levels. The presently disclosed methods are designed to minimize not only Hb1Ac levels (average blood glucose concentration) and attendant glucose toxicity; but also to control acute fluctuations in glucose concentration (glucose excursions). The reduction of glucose excursions also relieves the general inflammatory burden and oxidative damage to microvasculature resulting from oxidative stress. Thus even for patients in whom substitution of ultrarapid insulin for one or more oral medications may result in only similar control of HbA1c levels the treatment can confer a benefit over treatment with oral medications alone. Indeed this is a benefit that is also not attainable by addition of basal insulin to the treatment regimen. Nor can the merely rapid acting insulins be expected to deliver this benefit in full measure, especially as compared to an optimized dose of an ultrarapid acting insulin.

This benefit is accomplished by routinely administering an insulin preparation that mimics early phase release, that is an ultrarapid acting insulin preparation, in conjunction with at least one, preferably at least two or three meals a day, or with every established meal, or with every meal including snacks. Such treatment should be maintained, in increasing preference and for increasing effectiveness, for any number of days, weeks, months, and years, up to the remainder of the patient's life (or until such time as the underlying insulin-related disorder is cured or otherwise alleviated). By routinely it is meant that the advocated schedule of administration is the ideal and usual usage, but real world practice deviations from this protocol, such as occasional missed meals or missed doses, do not depart from the scope of the claimed invention. In various embodiments insulin is routinely administered with any meal or snack that would otherwise cause blood glucose to exceed 140 mg/dL, or alternatively 180 mg/dl; with any meal or snack constituting 1, 2, 3, or more bread exchanges; with any meal or snack containing more than about 15, 20, 30, or 45 g of carbohydrate.

Embodiments of the methods disclosed herein include a variety of dosing regimens including, but not limited to, dosing at every meal or snack, dosing at every meal or snack having a carbohydrate content of more than 15 g, dosing at every meal or snack having a carbohydrate content of more than 30 g, every meal or snack having a carbohydrate content of more than 45 g. Dosages and desired insulin composition concentrations may vary depending on the particular use envisioned. The determination of the appropriate dosage or route of administration is generally within the skill of an ordinary physician. However physicians are most commonly familiar with liquid formulations of insulin which allow for the continuous variation of dose. Insulin-FDKP is supplied as a dry powder in premeasured unit doses. Therefore specific instructions for determining the appropriate dosages of insulin-FDKP for an individual are disclosed herein. Furthermore the length of treatment may vary on the particular use and determination of the length of treatment is within the skill of an ordinary physician.

The rapid absorption and lack of a substantial tail in the activity profile of ultrarapid acting insulin preparations, such as insulin-FDKP, also mean that they pose a reduced potential for inducing hypoglycemia as compared to other insulins. Snacking to counteract late postprandial hypoglycemia is understood to contribute to the weight gain associated with standard insulin therapies. In contrast, use of insulin-FDKP has been associated with a lack of weight gain; indeed weight loss has been observed.

Intravenous injection of insulin can effectively replicate the first phase response and approximate the early phase response, but is not a practical therapy for a lifelong condition requiring multiple daily administrations. For these reasons, insulin for intravenous injection is not contemplated by the term ultrarapid acting insulin preparations as used herein. Traditional subcutaneous injections are absorbed into the bloodstream slowly by comparison, even using fast acting formulations, which still take up to an hour to reach maximal concentration in the blood and have a plateau lasting several hours. Many pulmonary formulations that have been assessed are equivalent to subcutaneous insulin in effectiveness and similarly fail to achieve the ultrarapid kinetics needed to mimic early phase release, as defined above. Nonetheless, the potential does exist for truly fast absorption using a non-intravenous based delivery, such as pulmonary and oral administration or subcutaneous injection of formulations comprising absorption promoting excipients. As described herein, pulmonary delivery using diketopiperazine-based dry powder formulations have been utilized.

Thus, a preferred embodiment provides a method to achieve the desirable early phase-like kinetics through pulmonary administration of a dry powder insulin formulation containing insulin complexed to diketopiperazine microparticles. This formulation is rapidly absorbed reaching peak serum levels within about 10 to 15 minutes. This is fast enough to mimic the kinetics of the physiologic meal-related early phase insulin response. The short, sharp rise to peak serum insulin concentration is critical to the rapid suppression of endogenous glucose production and has the additional effect of compressing the bulk of insulin action to the periprandial time interval, in contrast with slower acting formulations. This reduces the magnitude and duration of any meal-related excursions from normal glucose levels and associated glucose toxicity, as well as the risk of post-prandial hypoglycemia. Such improved control of blood glucose levels obtainable with this dry powder insulin is more fully described in co-pending U.S. patent application Ser. No. 11/278,381, filed Mar. 31, 2006, which is incorporated herein by reference in its entirety. As disclosed in U.S. application Ser. No. 11/329,686 and noted above, prior high insulin levels potentiate glucose elimination rate, meaning glucose can be eliminated more quickly if there is a prior high insulin concentration spike.

Diketopiperazine microparticle drug delivery systems and associated methods are described in U.S. Pat. Nos. 5,352,461 and 5,503,852. The use of diketopiperazine and biodegradable polymer microparticles in pulmonary delivery is described in U.S. Pat. Nos. 6,428,771 and 6,071,497. Details regarding various aspects of possible formulation and manufacturing processes can be found in U.S. Pat. Nos. 6,444,226 and 6,652,885; in U.S. Pat. No. 6,440,463; in co-pending U.S. Provisional Patent Application Nos. 60/717,524, filed Sep. 14, 2005; and 60/776,605, filed Apr. 14, 2006. The properties and design of a preferred breath-powered dry powder inhaler system is disclosed in U.S. patent application Ser. No. 10/655,153. Aspects of treatment using insulin complexed to diketopiperazine microparticles are disclosed in U.S. Pat. No. 6,652,885 as well as in co-pending U.S. patent application Ser. No. 11/032,278. Additionally U.S. patent application Ser. No.11/210,710 discloses the use of diketopiperazine salts to formulate insulin for both pulmonary and oral delivery. Each of the patents and patent applications mentioned in this paragraph is herein incorporated by reference in its entirety.

Whether insulin-FDKP or another insulin mimicking early phase release is administered alone or in conjunction with another agent, such as basal insulin, a suppressor of hepatic glucose release such as metformin, or an insulin sensitizing medication for example a thiazolidinedione (TZD), the ultrarapid acting insulin is administered in association with established meals, at least once and preferably two to four times daily, or more times up to with every meal, depending upon need. In order to achieve the maximum benefit of the treatment, it should be taken over an extended period of time, preferably at least 12 weeks, more preferably at least 24 weeks still more preferably from about 6 months to about two years, and most preferably for the remaining life of the patient or until the underlying diabetes is cured.

Current treatment of diabetes generally aims to reduce HbA1c levels to 7% or below. HbA1c levels above 8% indicate that patient's current therapy should be re-evaluated. It may be desirable to achieve normal HbA1c levels, but with the currently marketed insulin products this could only be accomplished at an unacceptable risk of severe hypoglycemia. Thus patients with HbA1c levels below 8% would not usually be considered candidates for more intensive treatment, that is, for treatment with insulin especially the current prandial insulins. Even those with HbA1c above 8% but not yet receiving basal or mixed insulin would not be considered to be candidates for treatment with a prandial insulin regimen. In embodiments disclosed herein the risk of hypoglycemia is much reduced, in part due to the lack of a tail of insulin activity exhibited by ultrarapid acting insulin, and it is possible to treat patients with HbA1c below 7%. Additionally, benefit can be expected from lowering blood glucose even at the high end of the normal range. For example one study showed that the risk of cardiovascular disease events was 5-8 times higher for individuals with HbA1c >7% as compared to those with HbA1c<5%, Another study showed a progressive increase in risk of kidney disease as HbA1c went from <6% to >8%. Accordingly, in some embodiments, patients with HbA1c levels $\leq 6.5\%$ or $\leq 6\%$ are selected for treatment. While the methods are generally discussed in reference to human patients adaptation to non-human mammals is not beyond the scope of the disclosure or the abilities of one of skill in the related arts.

Determination of Individual Dosage

Insulin-FDKP is a dry powder formulation for inhalation provided in cartridges containing a premeasured amount of powder which are inserted into an inhaler. The insulin is administered by inhaling through the inhaler to deliver the powder into the lungs. Cartridges containing different doses can be provided and an individual dosage can be obtained either by using a single cartridge containing the desired dosage or by using multiple cartridges (one at a time).

The patient can be a diabetic with inadequately controlled hyperglycemia, for example with HbA1c greater than 7%, or one with adequately controlled blood glucose levels but desiring to take advantage of other advantages obtainable with ultrarapid acting insulin (for example, weight loss or avoidance of weight gain, reduced risk of hypoglycemia, reduced glucose excursions, etc.).

Determination of individual dosage starts with identification of the daily meal (that is breakfast, lunch, dinner, regularly occurring snack, etc.) resulting in the highest 2-hour post-prandial blood glucose levels using 7 point SMBG (serum measured blood glucose). One then titrates up the dosage for that meal. Once an appropriate dosage is established for that meal the dosage for the daily meal leading to the next highest blood glucose level is titrated, and so on until dosages for all daily meals have been determined. In one embodiment the initial dosage is taken with the untitrated meals In an alternative embodiment the titration for all daily meals is carried our concurrently rather than sequentially. Meals for which dose titration is being carried out are preferably "usual" for the patient in terms of size and food component content with little variation in these parameters.

Titration begins by taking one low-dose cartridge with the meal(s) in question. Low dose insulin-FDKP cartridges can provide an emitted dose of, for example, 6 or 12 U of insulin. Most commonly the titration is carried out with 12 U cartridges but patients with smaller body masses, with lesser degrees of hyperglycemia to control, and/or lower degrees of insulin resistance may prefer to start the titration at a lower dose and/or proceed through the titration in smaller increments. For clarity the titration is described below with respect to the 12 U dose but it should be understood that the titration could similarly be based on a 6 U or other low-dose cartridge. Similarly even if titrating based on a cartridge that is not the lowest dose available one can use a smaller dose low-dose cartridge to provide the last increment (or decrease) in dosage as an alternative to the procedure described below.

One uses the initial dosage for a week. In each subsequent week the dosage for the meal is increased by the dose of the low-dose cartridge (i.e. 12 U) until either 1) the 2-hour postprandial median glucose is between 70 and 110 mg/dl, or 2) the dosage, based on emitted dose, is 72 U, or 3) an episode of hypoglycemia occurs. For episodes of mild to moderate hypoglycemia with confirmed SMBG of <70 mg/dl decrease dosage by one low dose (i.e. 12 U) cartridge and hold at that dose for one week then resume the titration. For an episode of severe hypoglycemia with confirmed SMBG <36 mg/dl decrease dosage by one low dose (i.e. 12 U) cartridge, hold at this new dose, and begin titration for next meal. In an alternative embodiment a pre-meal blood glucose between 70 and 110 mg/dl can also be used as a titration endpoint. In some embodiments the second criteria above for terminating dose escalation specifies a higher terminal dose or the criteria is not used at all.

In an alternative embodiment the initial dosage can be estimated based on relative bioavailability from the dosage of a subcutaneously administered insulin. This becomes important in adapting the titration scheme to other formulations and inhaler systems than that used in the examples below. A more universal scale is obtained by identifying dosage according to the insulin exposure (that is the AUC of blood insulin concentration over time). As the titration is described above 12U emitted corresponds to 3-4 subcutaneous equivalent units (subQ eq). Thus in various embodiments the low dose can be, for example, about 1, 1.5, 2, 3, 4, or 5 subQ eq units. The limit for dose escalation can be about 18, 24, 32 or more subQ eq units.

The expression of dose in subQ eq units also facilitates migration to use of an ultrarapid acting insulin if the patient is already on an insulin regimen. If the patient is already on a prandial insulin regimen they should start with the same subQ eq dose as they are currently using which is then titrated up or down from there basically as described above. If the patient is on a regimen with longer acting insulin alone or a mixture of short and longer acting insulins then 50% of the total daily dose should be divided by the number of daily meals and that amount of ultrarapid acting insulin in sub/Q eq units should be used as the initial dose in the titration. In the case in which the ultrarapid acting insulin is provided in form that does not allow an exact match to the current dosage one can round down or round to the nearest (that is up or down) dose of the ultrarapid acting insulin to use as the initial dose. In one embodiment this choice is left to the practitioner, but particular embodiments specify one or the other choice.

Accordingly, provided herein is a method of determining an individual's dosage of insulin-FDKP for a daily meal comprising the step of administering an initial dosage equivalent to one low-dose cartridge with the meal each day for a week. In each subsequent week the dosage is increased by the amount of one low-dose cartridge until a titration endpoint is reached wherein the titration is selected for the group of 1) achieving a 2-hour post-prandial median glucose is between 70 (or alternatively 80) and 110 mg/dl, 2) the dosage based on emitted dose is 72 U, 3) an episode of severe hypoglycemia with a confirmed SMBG <36 mg/dl occurs and the dosage is decreased by the equivalent of one low-dose cartridge, and 4) an episode of mild to moderate hypoglycemia with a confirmed SMBG of <70 (or alternatively 80) mg/dl occurs, the dosage is decreased by the equivalent of one low-dose cartridge for one week and then the titration is resumed until it reaches one of the other endpoints or the dosage is set at the level below that which produces the mild to moderate hypoglycemia.

Embodiments disclosed herein comprise a method in which the dosage for each daily meal is determined as described above for each of the daily meals in succession. This embodiment comprises determining which daily meal results in the highest 2-hour postprandial blood glucose level and titrating that meal first. In some embodiments this determination utilizes a 7 point SMBG. The daily meal resulting in the next highest 2-hour postprandial blood glucose level is then titrated in turn. The initial dosage is administered with each meal not being titrated for with a dosage has not been determined. In alternative embodiments dosages for all daily meals are titrated concurrently.

In one embodiment the low-dose cartridge provides an emitted dose of 3-4 subQ eq units of insulin. In another embodiment the low-dose cartridge provides an emitted dose of 1.5-2 subQ eq units of insulin. In some embodiments the group of titration endpoints further comprises a premeal blood glucose level between 70 and 110 mg/dl.

In various alternative embodiments the titration is based on at least three consecutive daily measurements as opposed to being carried out daily over a week as described above, or in a further alternative 3-6 daily measurements over the course of a week. In other alternative embodiments the titration is based on preprandial/pre-bedtime SMBG instead of 2 hour postprandial SMBG. That is the pre-lunch measurement is used to determine the breakfast dose, the pre-dinner measurement is used to determine the lunch dose, and the pre-bedtime measurement is used to determine the dinner dose.

Use of a Standard Dose

Traditional prandial insulin treatment has involved careful adjustment of insulin dosage to the expected glycemic load of the individual meal based on its size and content. The need for this can be avoided, or at least reduced through the use of an ultrarapid acting insulin formulation. Traditional prandial insulin formulations, whether administered by subcutaneous injection/infusion or by inhalation, exert their effect on blood glucose level largely by elevating the glucose elimination rate over a relatively extended period of time. The total glucose elimination brought about is generally proportional to the dose administered. In contrast ultrarapid acting insulin formulations exert their effect over a relatively constrained period of time and a greater proportion of their effect on blood glucose level is the result of rapidly reducing hepatic glucose release to basal levels. The rapid rise of blood insulin level obtained with ultrarapid insulins potentiates a rapid rise in glucose elimination activity and also provide a signal to the liver to reduce glucose release. However the high concentrations of insulin achieved to bring about these effects exceed the range in which glucose elimination rate (GER) is proportional to insulin concentration. Thus while further increasing insulin dosage does lengthen the period of time over which GER is elevated this is brought about by increasing the period of time in which the insulin concentration exceeds the range in which GER is proportional to insulin concentration. Therefore total glucose elimination with ultrarapid acting insulins is much less sensitive to dose. Moreover insulin concentrations return to baseline levels sooner after administration so the effect is also constrained in time and homeostatic mechanisms reassert themselves much sooner than with the relatively longer acting traditional short-acting formulations, thereby reducing the potential for late postprandial hypoglycemia due to the activity of the exogenous insulin.

As a result it can be feasible to set a standard dosage for each of the daily meals and use that dose without regard for variation in caloric content or glycemic load from meal to meal. Because so much of the blood glucose lowering effect is related to reduction of hepatic glucose release, effective reduction is achieved without careful matching of dosage to glycemic or caloric load even if a larger meal than usual is consumed. Because the elevation of GER is comparatively short-lived and generally well-matched in time to the period during which a meal will increase blood glucose levels there is a low risk of hypoglycemia even if a smaller meal is consumed. Nonetheless in preferred embodiments the caloric content and/or glycemic load of the meal is maintained within a range of from 25, 50, or 75% to 125, 150, 200 or 250%, of that of the usual meal (used in determining the standard dose). Since insulin resistance, and therefore responsiveness to insulin, does vary with circadian cycle it will generally be preferred to set a standard dose for each daily meal, though as a practical matter the standard dosage determined may be the same for different daily meals. This method can be particularly well-suited to diabetics with significant residual ability to produce insulin and regulate blood glucose levels, such as type 2 diabetics earlier in the progression of the disease.

Accordingly, provided herein are methods for treating diabetes with standardized doses that are not adjusted based on individual meal content. The method comprises prandial administration of a predetermined standard dosage of an ultrarapid acting insulin formulation without adjustment of the dosage based on meal content. In various embodiments any or all daily meals are treated according to this method; that is for example breakfast, or breakfast and lunch, or breakfast and dinner, or breakfast, lunch, and dinner, etc. In some embodiments a single predetermined dosage is used for all meals. Preferred embodiments utilize predetermined dosages for each daily meal; that is for example, for breakfast, for lunch, for dinner, etc. In some embodiments meal content is assessed as caloric content. In other embodiments meal content is assessed as glycemic load. In preferred embodiments meal content is maintained within a range of from 25, 50, or 75% to 125, 150, 200 or 250% of a usual meal used in determining the predetermined insulin dosage.

In one embodiment the ultrarapid acting insulin formulation is insulin-FDKP. In another embodiment the administration is by inhalation into the lungs.

Use of Split, Supplemental, and Delayed Dosages

With traditional prandial insulin regimens a dosage is selected based on an expectation of how much food will be consumed and then an attempt is made to conform consumption to the advance expectation. If more food is consumed, or its proportion of carbohydrate, fiber, and fat differs from usual or anticipated, it is not possible to improve glycemic control by administering a secondary dose subsequent to the meal when these factors are known with greater certainty, because of the delay between administration and onset of action with traditional formulations. In contrast ultrarapid acting insulin formulations take effect so quickly it can be advantageous to adjust the dosage of insulin to the meal by administering a secondary dose subsequent to the meal. Use of split dosages can be particularly well-suited to diabetics other than type 2 diabetics with good endogenous insulin production and only moderate insulin resistance, for example type 1 diabetics (past the "honeymoon" stage of the disease) and type 2 diabetics later in the progression of the disease In one application of this mode of administration split dosage is applied to meals in which delayed absorption is expected. The delay can be due to disease state—long-term diabetes is associated with delayed nutrient absorption; or can be due to meal content—higher fat and fiber content tend to delay food absorption. Use of split dosages can also be advantageously used in conjunction with multi-course or other prolonged meals such as at holiday celebrations and banquets. Even if the individual limits total consumption in accordance with their usual meals the fact that consumption extends over a longer than usual period of time will also lead to a prolongation of nutrient absorption. Split doses provide a way to address this prolonged profile of nutrient absorption. As compared to the dosage of insulin that would be used with the meal as a single dose one-half to three-quarters, for example two thirds, of the dose is administered at the beginning of the meal and the remainder of the dosage is administered 30 to 120 minutes later.

Accordingly, additional embodiments provide a method of treating diabetes comprising selecting a patient expected to have delayed nutrient absorption, administering an initial dose of ½ to ¾ of a predetermined dosage of an ultrarapid acting insulin formulation at the beginning of a meal, and administering the remainder of the predetermined dosage 30-120 minutes later. In one embodiment the initial dose is ⅔ of the predetermined dosage. In some embodiments delayed adsorption is related to a state of the disease (diabetes). In other embodiments delayed adsorption is related to meal content. In further aspects of these embodiments meal content comprises high fiber content. In other aspects of these embodiments meal content comprises high fat content. In a further aspect the high fact content constitutes ≧25% of the meal content. In a further aspect the high fat content constitutes ≧35% of the meal content. In one embodiment the ultrarapid acting insulin formulation is insulin-FDKP. In another embodiment the administration is by inhalation into the lungs.

In another application of this mode of administration, split dosage is used to adjust the insulin dosage to the actual glycemic load. An initial dose is administered at the beginning of the meal, blood glucose level is determined 60 to 120 minutes later, and a secondary or supplemental dose is administered if blood glucose exceeds 140 mg/dl. In some embodiments the secondary dosage is equal to 50-100% of the initial dosage. In some embodiments blood glucose is determined by continuous glucose monitoring.

Accordingly, additional embodiments provide a method of treating diabetes comprising administering an initial dose of an ultrarapid acting insulin formulation at the beginning of a meal, determining a blood glucose level 60-120 minutes after beginning the meal, and if the blood glucose level exceeds 140 (or alternatively 150) mg/dl administering a second dose of the ultrarapid acting insulin formulation wherein the dosage of the second dose is 25% or 50% to 100% of the dosage of the initial dose. In one embodiment the ultrarapid acting insulin formulation is insulin-FDKP. In another embodiment the administration is by inhalation into the lungs.

In a variation on this mode of administration no dose is administered at the initiation of the meal. Instead administration is delayed for example until 10, 15, 20, or 30 minutes after beginning the meal. This variation is particularly suitable when delayed nutrient absorption is expected.

Accordingly, embodiments disclosed herein provide a method of treating diabetes comprising administering a dose of an ultrarapid acting insulin formulation subsequent to the beginning of a meal to a patient expecting delayed nutrient absorption. In one embodiment delayed absorption is due to higher fat and fiber content as compared to a usual meal as used in determining dosage. In another embodiment delayed absorption is due to long standing diabetes. In one embodiment the ultrarapid acting insulin formulation is insulin-FDKP. In another embodiment the administration is by inhalation into the lungs.

Treatment of Patients of with Subcutaneous Insulin Resistance

Many of the advantages of insulin-FDKP are related to its ultrarapid kinetics. However insulin-FDKP is typically administered by inhalation of a dry powder preparation. There is a class of patients who can receive an additional benefit from this formulation due to its route of administration, namely patients with subcutaneous insulin resistance. This phenomenon is distinct from and unrelated to the insulin resistance typically associated with type 2 diabetes, which is generally understood to result from a reduced responsiveness of cells throughout the body to insulin.

The phenomenon of subcutaneous insulin resistance is not universally accepted by experts in diabetes as a bona fide physiological state. Certainly its etiology is not well understood and indeed there may be multiple factors that can lead to this condition. Nonetheless experience with inhalable insulin has demonstrated the clinical reality of this phenomenon. There are patients who have required substantially greater doses of insulin than might otherwise be expected when treated with subcutaneously administered insulin who upon switching to a pulmonary insulin require an amount of insulin more in line with what would be expected based on their medical condition. Subcutaneous insulin resistance can also contribute to difficulty in establishing reasonable control of hyperglycemia and in variability in the response to insulin.

To prospectively identify diabetes patients having subcutaneous insulin resistance several factors can be considered. First of all the patient will be using high doses of insulin, especially compared to what would typically be required based on their medical condition including body weight and state of progression of the disease. For example a high dose of insulin is one greater than 2 units/Kg/day. This criterion can further be paired with the patient having normal or near-normal basal levels of endogenous serum insulin, for example $\leq 50$ µU/ml of insulin. Such patients typically will have type 2 diabetes in an early stage in the progression of the disease. Alternatively high insulin usage can be paired with lipoatrophy or lipodystrophy as diagnostic criteria.

In yet other alternative embodiments high insulin usage can be paired with very poorly controlled hyperglycemia as the selection criteria. Very poorly controlled hyperglycemia can be evidenced by three HbA1c level determinations $\geq 9\%$ in a 12 month period despite treatment with an intensified insulin regimen, for example basal-bolus therapy, or continuous subcutaneous insulin infusion (CSII; that is, an insulin pump), etc., over a period $\geq 6$ months. Commonly HbA1c levels are determined quarterly. It is preferred that the three HbA1c level determinations $\geq 9\%$ be consecutive. In alternative embodiments very poorly controlled hyperglycemia can be evidenced by two HbA1c level determinations $\geq 9\%$ in a 6-9 month period.

In still further alternative embodiments high insulin usage can be paired with life threatening glycemic instability as the criteria for selection. Life threatening glycemic instability can be characterized by periods of hyperglycemia and/or hypoglycemia despite adherence to diet, exercise, and insulin regimens.

Accordingly embodiments herein provide methods of treating diabetics with subcutaneous insulin resistance. These methods include a step for the selection of patients with subcutaneous insulin resistance on the basis of atypically high insulin dosage. In some embodiments the insulin dosage is $\geq 2$ units/Kg/day. In some embodiments the selection is further based on the patient having normal or near-normal levels of endogenous insulin. In some of these patients the basal level endogenous insulin is $\leq 50$ µU/ml. In other embodiments the selection is further based on the patient being on an intensified insulin regimen and having three HbA1c level determinations $\geq 9\%$ in a 12 month period. In still other embodiments the selection is further based on the patient having life threatening glycemic instability characterized by periods of hyperglycemia and/or hypoglycemia despite adherence to their insulin regimen and any diet or exercise regimen.

These methods also include a step of discontinuing treatment with subcutaneously administered rapid-, short-, or intermediate-acting insulin formulations. Note that patients who cannot produce sufficient insulin to meet basal requirements need to continue taking basal insulin even if it is administered subcutaneously. Presently the only basal (long-acting) insulin formulations commercially available are for subcutaneous administration. However other long acting insulins are being developed which could potentially be administered by other routes of administration and their use in the methods herein is contemplated. These methods also include the step of (initiating) treatment by administration of prandial doses of insulin-FDKP by inhalation.

Further embodiments can include a step for confirming the diagnosis of subcutaneous insulin resistance by determining that a similar or improved degree of glycemic control is achieved with a substantially lower dosage of insulin. In some embodiments glycemic control is assessed as HbA1c level. In other embodiments it is assessed as post-prandial and/or fasting blood glucose levels. In various embodiments the insulin dosage (exclusive of any basal requirement) is reduced by $\geq 10$, $\geq 20$, or $\geq 50\%$, or more. In some embodiments the reduced dosage is assessed from measurements of serum insulin levels. In other embodiments it is based on the dosage used and the relative bioavailability of the insulin formulations.

Combined Use of Ultrarapid Acting Insulin and Long Acting Insulin Analogs

One mode of use of ultrarapid acting insulin is to use it in combination with a long acting insulin in a basal-bolus regimen. In basal-bolus therapy a long acting insulin is used to provide or supplement a basal level of insulin and a bolus of short acting insulin is administered in conjunction with meals to handle the resultant increased glucose load. The various advantageous characteristics of ultrarapid acting insulin make it an ideal choice for use as the short acting insulin in such regimens.

Many long acting insulins are administered twice a day, but insulin glargine (sold as LANTUS® by Sanofi-Aventis) is approved and marketed for once a day administration. According to the manufacturer's prescribing information (March 2007 revision) insulin glargine provides relatively constant glucose lowering activity over a 24-hour period and may be administered any time during the day provided it is administered at the same time every day. Additionally, insulin detemir (sold as LEVEMIR® by Novo Nordisk) is approved and marketed for administration either twice a day or once a day with the evening meal or at bedtime (manufacturer's prescribing information, Version 3 issued May 16, 2007).

In clinical trials it was found that an ultrarapid acting insulin formulation comprising insulin-FDKP used in combination with insulin glargine was effective in managing glucose excursions. In 7 point glucose measurements insulin-FDKP was able to flatten the jagged pattern resulting from post-prandial glucose excursions, but over the course of the day baseline blood glucose levels tended to rise. Similar behavior was observed in type 1 (See Example 2 and FIG. 12) and type 2 diabetics (see FIG. 13). There are several factors that may contribute to this rise. Insulin resistance tends to rise over the course of the day. Additionally the insulin glargine used in the study was administered in the evening before bedtime as contemplated in the manufacturer's prescribing information. Thus the greatest demand for insulin activity is occurring late in the period of effectiveness of the insulin glargine dose when it is weakening.

In typical combinations insulin glargine is used in combination with either a prandial short acting insulin or mixes of short and intermediate acting insulins administered before breakfast and dinner. Intermediate acting insulins are intended to provide glucose lowering activity for both meal and between-meal periods. Even the marketed short acting insulins exert the majority of their activity after most of a meal's nutrients have been absorbed. Thus in commonly used regimens involving combinations of insulin glargine and shorter acting insulins, the other insulins provide supplementary activity during waking hours. In contrast insulin-FDKP has a short duration of action, well matched to the time period in which a meal produces an increased glucose load, but not providing substantial insulin activity for baseline control. Thus when combined with an ultrarapid acting insulin such as insulin-FDKP any insufficiency of insulin glargine dose or duration will be exacerbated as compared to established regimens. Insulin detemir has a shorter duration of action than insulin glargine so that when used once a day such deficiencies should be even more pronounced. To remediate such effects regimens combining the use of ultrarapid acting insulins and a long acting insulin analog should specify that the long acting insulin analog be administered early in waking hours, for example at breakfast time or within 1, 2, 3 or 4 hours of waking. In some embodiments an early dose of the long acting insulin analog is the only dose given in the course of the day. In other embodiments the long acting insulin analog is insulin glargine and it is administered twice a day, an early dose and a late dose approximately 8 to 14, preferably 10-12, hours later, for example around dinnertime. A typical cycle of sleeping and waking, in which a person sleeps for an extended period, usually at night, and then wakes and becomes active for the remainder of a day, naps notwithstanding, is assumed. Thus phrases such as within a certain time after waking, early in waking hours, and similar terminology refer to the point at which a subject wakes and initiates their daily activities.

Combined Use of Ultrarapid Acting Insulin and Basal Insulin Provided by Infusion Insulin pumps are compact devices that deliver various forms of insulin at appropriate times to help control the blood glucose level. Used correctly, these devices improve blood glucose control with fewer hypoglycemic episodes and better long-term control. The pumps are programmable and give patients a degree of freedom to vary what, when or how much they eat by allowing insulin delivery rates to be adjusted for different times of day. The latest models of insulin pumps are relatively easy to use and convenient to carry. These newer pumps have built-in dosage calculators that manage the complex insulin dosage calculations previously performed by patients. Patients are able to program bolus doses to coincide with a meal as well as different basal insulin delivery rates for different times of day, depending on changing needs. These pumps also calculate how much insulin is still working from the previous bolus dose. Some pumps have additional smart features such as programmable reminders and alerts, information and download capabilities that allow the patient to save information to a computer for accurate record-keeping, a carbohydrate database for calculating the amount of carbohydrate ingested in a meal, and certain safety features.

As an alternative to subcutaneous bolus injection of long acting insulin it is also possible to provide basal insulin by continuous infusion. This approach obviates the need for long acting insulin since insulin is continually provided. This approach can also avoid any drawbacks associated with such preparations, for example increased immunogenicity or binding to receptors for insulin-like growth factors that can occur with analogs. As the rate of infusion can be changed throughout the day with this approach, the profile of basal insulin activity can be more readily adjusted to variations in diet and individual physiology. (The capabilities of insulin pumps are more fully discussed in the section dealing with artificial pancreas systems, below). A common methodology with insulin pumps is to aim to cover both prandial and basal needs by using one of the rapid acting analogs. When the pump is only being used to provide basal insulin—as with a prandial non-pumped ultrarapid acting insulin—regular human insulin can be used. However for patients with less stable basal need the more rapid kinetics of the rapid acting analogs can offer an advantage.

Accordingly embodiments provide a method of treating diabetes comprising infusing insulin with an insulin pump to meet basal insulin needs and administering an ultrarapid acting insulin to meet prandial needs. In some embodiments the pumped insulin is regular human insulin. In other embodiments the pumped insulin is a rapid acting insulin analog. In one embodiment the ultrarapid acting insulin formulation is insulin-FDKP. In another embodiment the administration of the ultrarapid acting insulin is by inhalation into the lungs.

Use of Ultrarapid Acting Insulin in Combination with or in Place of Oral Antidiabetic Medications Standard of care in the treatment of type 2 diabetes is defined and regularly updated in consensus statements published jointly by the American Diabetes Association and the European Association for the Study of Diabetes. The general course of treatment advocated, summarized below, has remained fairly stable in recent years (compare for example Nathan et al. *Diabetes Care* 29:1963-1972, 2006; Nathan et al. *Diabetes Care* 31:173-175, 2008; and Nathan et al. *Diabetes Care* 32:193-203, 2009) with the most significant change in the most recent update being the addition of GLP-1 agonists to the treatment algorithm.

The course of treatment as advocated in these consensus statements begins with lifestyle changes plus the drug metformin at diagnosis (Step 1). Lifestyle changes include improved diet and increased exercise. Metformin is a drug classified as a biguanide. Although historically these drugs have been described as insulin sensitizers, there primary effect is to reduce hepatic glucose output. This activity appears to be dependent on the presence of insulin and metformin treatment can be associated with somewhat increased sensitivity to insulin. However avoided herein is applying the term "insulin sensitizer" to the biguanides as the mechanism of action is different from that of the thiazolidinediones which are now more commonly intended by the term and for which the primary effect to increase insulin sensitivity. As metformin is present throughout the day its effect is observed as a reduction in fasting blood glucose levels (FBG). Approximately 30% of patients cannot tolerate metformin, at least at dosages adequate for acceptable glycemic control, with gastrointestinal side-effects being a primary issue. The prescribing information (January 2009 revision) for metformin (sold as GLUCOPHAGE® by Bristol-Myers Squibb) includes contraindications for use in patients with renal disease or dysfunction, hypersensitivity to the drug, or metabolic acidosis, as well as other precautions.

If adequate glycemic control is not attained (generally HbA1c remains ≧7%) with Step 1 treatment Step 2 treatment calls for the addition of a second agent. This can be basal insulin, a sulfonylurea, pioglitazone, or a GLP-1 agonist. If the two agents (the second agent not being basal insulin) still do not establish adequate glycemic control the consensus calls for either switching the second agent to basal insulin, our using a combination of a sulfonylurea and pioglitazone as the second agent. If the combination of a sulfonylurea and pioglitazone still does establish adequate glycemic control the consensus calls for switching the second agent to basal insulin. By any of these paths the consensus advocates that the first insulin regimen used be basal insulin.

The sulfonylureas are insulin secretagogues, that is, they enhance insulin secretion. Included in this class are the drugs chlorpropamide, glyburide, gliclazide, glimepiride and glipizide. A major issue with these agents is an increased risk of hypoglycemia, especially great with chlorpropamide and glyburide. Use of these agents has also been implicated in increased mortality from cardiovascular disease. Weight gain is common with these agents. Contraindications, precautions, and drug interactions typical of the sulfonylureas can be found in the prescribing information for glipizide (sold as GLUCOTROL® by Pfizer; September 2006 revision). Concern has also been raised that insulin secretagogues increase demand on an already overtaxed pancreas contributing to the progressive decrease in β-cell function and limiting their long term usefulness. Other insulin secretagogues are known such as the glinides, for example repaglinide and nateglinide. The risk of weight gain with these agents is similar to the sulfonylureas, but the risk of hypoglycemia may not be as elevated. GLP-1 agonists and DPP-4 (dipeptidyl peptidase-4) inhibitors can also be considered insulin secretagogues. As used, insulin secretagogues provide their activity throughout the day so that their effect is readily seen as a reduction in FBG.

Pioglitazone (sold as ACTOS® by Takeda Pharmaceuticals) is a thiazolidinedione (glitazone, TZD) which increase the sensitivity of muscle, fat, and liver to insulin thereby counteracting the insulin resistance aspect of type 2 diabetes, and are therefore commonly referred to as insulin sensitizers. TZDs have been associated with fluid retention and congestive heart failure and also with increased rates of bone fracture, especially in women with osteoporosis. The TZDs also include the drug rosiglitazone (sold as AVANDIA® by GlaxoSmithKline) which has been further associated with myocardial ischemia. These and other side-effects, precautions, etc., such as weight gain are reporting in the manufacturer's prescribing information for ACTOS® (August 2008 version) and AVANDIA® (October 2008 version).

The third (and last) step in the consensus algorithm is reached if—or when as type 2 diabetes is a progressive disease—adequate glycemic control is not attained by treatment including basal insulin under the second step. The third step advocates that the lifestyle changes and metformin treatment of the previous stages be continued along with intensified insulin treatment. As described intensified treatment can include prandial use of rapid acting insulin analogs, but definitely involves the continued use of basal insulin.

Patient populations treated according to the embodiments herein disclosed are distinct from those most commonly receiving insulin therapies. Indeed the factors that might impel a clinician to prescribe insulin to individuals according to current paradigms do not shed any light on the relative effectiveness of an ultrarapid acting insulin as compared to oral antidiabetic agents especially given the distinct pharmacokinetic profiles of the insulin preparations available. Moreover, as seen above use of insulin typically begins with basal insulin, with prandial insulins being added only after the failure of basal insulin alone. In contrast the methods disclosed herein involve use of prandial ultrarapid acting insulin early in the progression of treatment.

Patients with early stage insulin disorders can be divided into various subpopulations and treated according to various embodiments of the present invention. Some persons make sufficient insulin to maintain a non-hyperglycemic fasting blood glucose level but cannot avoid acute fluctuations in blood glucose after eating. Early type 2 diabetics can often use diet and exercise to control even substantial hyperglycemia, but will have already lost their early phase insulin release. In current practice patients failing diet and exercise are most often next treated with a suppressor of hepatic glucose output, such as metformin, with the goal of overcoming insulin resistance and improving the effectiveness of the insulin that is produced. In embodiments disclosed herein, these patients are administered a prandial, early phase-mimicking insulin preparation instead of, or in addition to, the insulin sensitizer. Less often (and previously) the first oral medication offered diabetics was an insulin secretagogue, such as a sulfonylurea, to increase insulin secretion. More commonly (and currently) such agents are used in combination with a suppressor of hepatic glucose output as a subsequent step in treatment if use of the sensitizer alone does not provide the desired level of glycemic control. However, use of secretagogues can also lead to weight gain and hypoglycemic events so, in a one embodiment, a prandial, early phase-mimicking insulin preparation is used instead of a secretagogue in such combination treatments.

Both fasting and postprandial blood glucose levels contribute to elevation of HbA1c levels. Ultrarapid acting insulin preparations can advantageously impact both fasting and postprandial blood glucose levels. It was initially appreciated that they are particularly well suited to addressing control of postprandial blood glucose in contrast with basal insulins or insulin secretagogues, or even short acting insulins. This is understood to be due in part to their more rapid suppression of endogenous glucose production (see Example 1). Thus embodiments disclosed herein are directed to patients with poorly controlled postprandial blood glucose or in whom the lack of glycemic control is more strongly associated with elevated postprandial blood glucose. For example patients with a lesser degree of insulin resistance may be able to produce sufficient insulin to provide substantial control of fasting blood glucose and in some embodiments can be selected for treatment with ultrarapid insulin alone. In comparison patients with a higher degree of insulin resistance may have poor control of both fasting and postprandial blood glucose and in embodiments would be selected for treatment with ultrarapid insulin and an oral antidiabetic agent in combination.

Ultrarapid Acting Insulin and Suppressors of Hepatic Glucose Output

Both ultrarapid acting insulin and biguanide drugs such as metformin act as suppressors of hepatic glucose release. However as used the drugs exert their effect around the clock whereas prandial ultrarapid acting insulin exerts this effect more particularly following meals. Thus ultrarapid acting insulin can substitute for or augment the activity of the oral suppressors of hepatic glucose output.

Accordingly in one embodiment ultrarapid acting insulin is used in treating a subject with type 2 diabetes in need of improved glycemic control with well or moderately controlled FBG but poorly controlled PPG. In various aspects of the embodiment need for improved glycemic control is determined as HbA1c level, 1- or 2-hour PPG, or oxidative stress. In some embodiments well controlled FBG is FBG $\leq$110 Or $\leq$130 mg/dL. In some embodiment moderately controlled FBG is FBG $\leq$154 mg/dL, $\leq$180, or $\leq$192 mg/dL. Studies have determined that at HbA1c levels $\leq$8.4% at least half of overall hyperglycemia is due to PPG (Monnier, L. et al. *Diabetes Care* 26:881-885, 2003). Thus in some embodiments a subject with well or moderately controlled FBG but poorly controlled PPG is a subject with HbA1c$\leq$8.4%. (An HbA1c of 8.4% corresponds to a mean plasma glucose level of approximately 192-198 mg/dL; see *Diabetes Care* 32, suppl. 1:S13-S61, 2009, especially tables 8 and 9). In various embodiments a subject with poorly controlled PPG in one with 1- or 2-hour PPG $\geq$140, or $\geq$180, or $\geq$200 mg/dL. It should be noted that subjects whose 2-hour PPG following a 75 g glucose challenge was $\geq$200 mg/dL had an almost doubled risk of mortality than those whose 2-hour PPG was <200 mg/dL regardless of their FPG (*Lancet* 354:617-621, 1999). In one embodiment the subject is not currently receiving any drug treatment and ultrarapid insulin is used as the sole pharmacologic agent. In another embodiment the subject is undergoing treatment with an oral suppressors of hepatic glucose output and prandial ultrarapid insulin is added to their treatment regimen. In one embodiment the oral suppressors of hepatic glucose output is metformin. In one embodiment the ultrarapid acting insulin formulation is insulin-FDKP. In another embodiment the administration of the ultrarapid acting insulin is by inhalation into the lungs.

In other embodiments, a subject with type 2 diabetes in need of improved glycemic control could benefit from treatment with a suppressor of hepatic glucose output, but such oral agents are contraindicated or not tolerated, and ultrarapid acting insulin is used instead. In a variation the oral agent is not tolerated in sufficient dosage and ultrarapid acting insulin is used to supplement its activity.

Ultrarapid Acting Insulin and Insulin Secretagogues

Insulin secretagogues such as the sulfonylureas and the glinides increase insulin secretion and thereby insulin concentrations in circulation. Ultrarapid acting insulin preparations also increase insulin concentrations in circulation. However as used the drugs exert their effect around the clock whereas prandial ultrarapid acting insulin exerts this effect more particularly following meals. Thus ultrarapid acting insulin can substitute for the activity of the insulin secretagogue. In one embodiment the ultrarapid acting insulin formulation is insulin-FDKP. In another embodiment the administration of the ultrarapid acting insulin is by inhalation into the lungs.

Accordingly in one embodiment, a patient under treatment with a suppressor of hepatic glucose output and an insulin secretagogue discontinues treatment with the secretagogue and institutes treatment with an ultrarapid acting insulin. In a related embodiment a patient under treatment with a suppressor of hepatic glucose output who is a candidate for treatment with an insulin secretagogue and instead institutes treatment with an ultrarapid acting insulin rather than with a secretagogue. In one embodiment the patient is in need of improved glycemic control. In various aspects of the embodiment need for improved glycemic control is determined as HbA1c level, 1- or 2-hour PPG, or oxidative stress.

In other embodiments a subject with type 2 diabetes could benefit from treatment with an insulin secretogogue, but such oral agents are contraindicated or not tolerated, and ultrarapid acting insulin is used instead. In other embodiments the patient is in need of reducing the risk of hypoglycemia or weight gain.

Ultrarapid Acting Insulin and Insulin Sensitizers

Insulin sensitizers, such as pioglitazone and the other TZDs improve insulin utilization in various tissues thereby reducing insulin resistance and leading to a reduction in circulating insulin levels. Treatment with TZDs results in notable decreases in FBG. Treatment with prandial ultrarapid acting insulin leads to a reduction in FBG. This is despite the fact that there is no direct glucose eliminating activity due to prandial ultrarapid acting insulin during fasting periods. The impact of ultrarapid acting insulin preparations on fasting blood glucose levels was unexpected and suggests that they can reduce insulin resistance or act as an insulin sensitizer. Interestingly the rapid insulin concentration peak obtained with ultrarapid acting potentiates subsequent insulin activity. This is particularly noticeable in type 2 diabetics in the time frame immediately following administration however the effect may be longer lived. Thus treatment with prandial ultrarapid acting insulin has effects similar to insulin sensitizers.

Accordingly, in some embodiments, patients are selected for treatment comprising an ultrarapid acting insulin on the basis of having a high degree of insulin resistance. In other embodiments patients who would benefit from treatment with an insulin sensitizer, such as a TZD, but have a sensitivity to the drug or are otherwise contra-indicated, are treated with an ultrarapid acting insulin in place of the drug. For example TZDs can be contraindicated in women with osteoporesis.

Patients who can benefit from treatment with prandial ultrarapid acting insulin according to various embodiments include those who obtain inadequate glycemic control with an insulin sensitizer and would otherwise have an insulin secretagogue added to their treatment regimen, or those who obtain inadequate glycemic control with a combination of an insulin sensitizer and an insulin secretagogue. Subsets of these groups include those who further are needle-phobic or would otherwise want to avoid injections, and those who further are obese, overweight, or otherwise desire to avoid or minimize weight gain or need to lose weight. Additionally elevated insulin levels are associated with a greater occurrence of breast cancer. Thus persons with an elevated risk of breast cancer can particularly benefit from a lowering of insulin resistance. In one embodiment the ultrarapid-acting insulin formulation is insulin-FDKP. In another embodiment the administration of the ultrarapid acting insulin is by inhalation into the lungs.

Prandial Ultrarapid Insulin Versus Basal Insulin

When treatment with two oral medications does not provide adequate glycemic control standard of care offers paths to the use of basal insulin or use of a third oral medication. The choice to add a third oral medication instead of adding insulin is often influenced by reticence to accept daily injections even in the absence of an outright needle phobia, the risk of hypoglycemia, and the likelihood of weight gain. Thus embodiments of the invention provide a successor treatment to combination oral therapy that includes insulin, but is needle-free and minimizes or eliminates weight gain. The inhalable insulin EXUBERA®, because of its subcutaneously delivered insulin-like kinetics, would not be expected to confer the same benefits as an ultrarapid acting insulin preparation. This use shows that prandial ultrarapid insulin offers a unique alternative to the early use of basal insulin generally, and that offers particular advantage to patient populations in which needle use, the risk of hypoglycemia, or the prospect of weight gain are particularly problematic.

Patients who can benefit from treatment according to various embodiments disclosed herein include those who obtain inadequate glycemic control with an oral suppressors of hepatic glucose output and would otherwise have an insulin secretagogue added to their treatment regimen, or those who obtain inadequate glycemic control with a combination of an oral suppressor of hepatic glucose output and an insulin secretagogue. Subsets of these groups include those who further are needle-phobic or would otherwise want to avoid injections, and those who further are obese, overweight, or otherwise desire to avoid weight gain or need to lose weight.

EXAMPLES

Example 1

The experiments were conducted to identify the effect of an ultrarapid acting insulin, specifically a formuslation for inhalation comprising insulin-FDKP, when compared to subcutaneously administered insulin lispro (lispro, HUMALOG®, Eli Lilly & Co.) and an inhaled recombinant human insulin (EXUBERA®, Pfizer Inc.) on endogenous glucose production after a meal challenge and during a euglycemic glucose clamp procedure in subjects with type 2 diabetes. The insulin-FDKP formulation is administered to the subjects by oral inhalation using a MEDTONE® dry powder inhaler (MannKind Corp.).

Following the completion of the meal challenge, the data was analyzed as per the statistical analysis plan. Total insulin exposure was found to be approximately 40% greater following the administration of 12 U lispro than following either 45 U insulin-FDKP (TI) or 4 mg EXUBERA®. Hence, the study was redesigned, and subjects did not proceed to the euglycemic glucose clamp portion of the study under the original protocol and treatments (4 mg EXUBERA®, 45 U TI and 12 U lispro). The study was amended (A1) and included 12 subjects (10 were reenrolled from the first meal challenge), and only two treatments, which were 10 U lispro and 60 and 90 U TI. The doses were selected based on the relative bioavailability observed following the first meal challenge (OP), where under an assumption of linear kinetics, 10 U lispro and 60 U TI would result in similar exposure. The 90 U dose group was included to assess the effect of the highest dose group of TI studied in Phase 3 trials. Six of the 12 subjects received 60 U TI and the other 6 subjects received 90 U TI. All 12 subjects received 10 U lispro in a crossover fashion.

Methods and results below are described in terms of the Original Protocol (OP), which includes the meal challenge in 18 subjects with three treatments (EXUBERA®, lispro and TI) and Amendment 1 (A1), which includes 12 subjects treated with only TI and lispro.

Subjects with insulin-treated type 2 diabetes participated in the study. The subjects were screened and evaluated before, during and after the experiments and their data analyzed as described below. Subjects were selected based on several key inclusion criteria, including, male and female, having ≧18 and ≦70 years of age with clinical diagnosis of type 2 diabetes mellitus for ≧12 months. The subjects selected for the study also had stable anti-diabetic regimen with insulin for the previous 3 months; HbA1c≦8.5%; Body Mass Index (BMI) between ≦34 kg m$^2$ and ≧25 kg m$^2$; urine cotinine ≦100 ng/mL; PFTs of FEV1≧70% of predicted value, single breath CO diffusing capacity (DLco uncorrected) ≧70% of predicted. Subjects had also been treated with oral antidiabetic medication within the previous 3 months; total daily insulin requirement of ≧1.2 IU/kg body weight. Criteria for exclusion from the study also included unstable diabetes control and/or evidence of serious complications of diabetes (e.g., autonomic neuropathy); serum creatinine >1.8 mg/dL in female subjects and >2.0 mg/dL in male subjects. Other clinically important pulmonary disease was confirmed by documented history or pulmonary function testing.

Under OP, the study was planned to be a randomized, open label, 3-way cross-over study. The visits comprised an initial screening visit, 3 sequential treatment visits for the meal challenge test followed by a minimum 8-week (up to a maximum of 12 weeks) blood-loss recovery period, an interim safety visit, 3 sequential visits for the glucose clamp procedure, and a final close-out visit. At this analysis all patients at least had completed the meal challenge visits and only those data have been used. The screening visit(s) (V1) occurred 1 to 21 days before the first treatment visit (V2) with 7 to 21 days elapsing between treatment-visits (V2, V3, and V4) for the meal challenge test. A minimum of 8 weeks elapsed between V4 and the next treatment visit, (V6). An additional safety visit (V5) was scheduled 1-3 days prior to the first of 3 glucose clamp procedures (V6). The glucose clamp procedure occurred at 3 visits, Visits V6, V7, and V8, with 7 to 21 days elapsing between the visits. A final visit (V9) occurred 2 to 10 days after V8, to assess physical examination such as body weight and height.

Under A1, the study was planned to be a randomized, open label, 2-way cross-over study. The visits comprised an initial screening visit, 2 sequential treatment visits for the meal challenge test followed by a minimum 4-week (up to a maximum of 12 weeks) blood-loss recovery period, an interim safety visit, 2 sequential visits for the glucose clamp procedure, and a final close-out visit. The screening visit(s) (V1) occurred 1 to 21 days before the first treatment visit (V2) with 7 to 21 days elapsing between treatment-visits (V2 and V3) for the meal challenge test. A minimum of 4 weeks elapsed between V3 and the next treatment visit, (V5). An additional safety visit (V4) was scheduled 1-3 days prior to the first of 3 glucose clamp procedures (V5). The glucose clamp procedure occurred at 2 visits, Visits V5 and V7, with 7 to 21 days elapsing between the visits. A final visit (V8) occurred 2 to 10 days after V7, to assess physical examination such as body weight and height.

Each treatment visit during the meal challenge had the subjects hospitalized in the clinical unit the night before initiation of treatment. At the first treatment visit (V2) for the meal challenge test, subjects were randomly allocated to a treatment order for insulin-FDKP, insulin Lispro or EXUBERA® (OP) and insulin-FDKP and lispro (A1) based on a cross-over design. Each subject followed the same randomization order for the glucose-clamp procedures as for the meal challenge tests.

During the study, periodic blood draws for determination of pharmacokinetic and/or pharmacodynamic parameters, and safety were taken beginning at 12 hours prior to onset of the treatment regimens and meal challenge, and thereafter for a period of 8 hours. Screening testing and all 3 meal challenge tests required in combination a total of 409.5 mL of blood for analysis and evaluation of the treatments (OP) and 279 mL blood for A1. The glucose clamp procedure visits, final visit, and the interim safety visit required a total of 514.2 mL of blood (OP) and 365 mL blood for A1 for the analysis and evaluation of the treatments. The total blood voulume needed for A1 studies was 644 mL per subject. Radiolabeled $D_2$-glucose infusion was administered to subjects 12 hours prior to onset of the meal challenge and insulin treatment.

Meal Challenge Test: BOOST PLUS® (12 fl. oz.) consisting of 67.5 g carbohydrate, 21 g protein, 21 g fat, energy content 540 kcal was used for the meal challenge test. The BOOST PLUS® was enriched with U-$^{13}$C-glucose to determine the amount of absorbed glucose. Concurrent enriched continuous infusion of 6,6-$^2$H$_2$ glucose was used to assess endogenous glucose production EGP. Sampling for fasting EGP (f-EGP) occurred before the start of an intravenous insulin lispro infusion, i.e., at the end of a 7-hour period of enriched infusion of 6,6-$^2$H$_2$ glucose under OP. In A1, the continuous insulin infusion was conducted using either insulin lispro (for subjects treated with TI) or regular human insulin (for subjects treated with lispro). Baseline blood glucose concentrations of 90 mg/dL (OP) and 110 mg/dL (A1) were established and maintained by variable infusion of insulin and 20% glucose enriched with 6,6-$^2$H$_2$ glucose over a period of at least 5 hours prior to dosing with insulin-FDKP, insulin lispro, or EXUBERA® (OP) or insulin-FDKP and lispro under A1. Insulin Lispro infusion rate (OP) and lispro or RHI infusion rate (A1) was fixed at the lowest possible level 90 minutes prior to treatment dose. Following dosing, blood glucose concentrations were kept from falling below 90 mg/dL (OP) and 75 mg/dL (A1) by a glucose infusion.

Dosing with the test treatments was performed with administration of a dose of 45 U of Insulin-FDKP, 12 U of subcutaneous insulin lispro, or 4 mg of recombinant human insulin (EXUBERA®) administered by oral inhalation at time point 0 (OP), or 10 U subcutaneous lispro and 60 or 90 U TI (A1) immediately prior to BOOST PLUS® ingestion. Under OP, the dose for insulin lispro was selected based on information obtained from the regulatory label. The dose selected for EXUBERA® was obtained by means of back calculation of the most commonly used dose information presented to the FDA Advisory Committee in the EXUBERA® Briefing Document. The insulin-FDKP dose was derived from results in completed phase 2 and 3 clinical studies carried out by MannKind Corporation, the assignee of the application. Under A1, the doses were calculated based on insulin exposure observed under OP. Blood glucose concentrations were measured at regular intervals from arterialized venous blood samples. The amount of orally absorbed glucose was estimated by determination of U-$^{13}$C-glucose. EGP was determined by measurement of 6,6-$^2$H$_2$ glucose applying the modified calculations for the non-steady state (R. Hovorka, H. Jayatillake, E. Rogatsky, V. Tomuta, T. Hovorka, and D. T. Stein. Calculating glucose fluxes during meal tolerance test: a new computational approach. *Am. J. Physiol Endocrinol. Metab* 293 (2):E610-E619, 2007). C-peptide concentrations were measured pre- and post-dose to assess endogenous insulin secretion. In addition, glucagon and free fatty acid concentrations were also determined.

Glucose-clamp Procedure: An enriched continuous infusion of 6,6-$^2$H$_2$ glucose was used to assess EGP. Blood samples to determine fasting EGP (f-EGP) were taken before the start of an intravenous insulin infusion, i.e., at the end of a 7-hour period of enriched infusion of 6,6-$^2$H$_2$ glucose into the subjects. Baseline blood glucose concentrations of 90 mg/dL (OP) and 110 mg/dL (A1) were established and maintained by variable infusion of insulin and 20% glucose enriched with 6,6-$^2$H$_2$ glucose by means of a Biostator device over a period of at least 4 hours prior to dosing with insulin-FDKP, insulin lispro, or EXUBERA® (OP) and either lispro or TI under A1.

Dosing with the test treatments was performed by administering a dose of 45 U of Insulin-FDKP, 12 U of sc Insulin Lispro, or 4 mg of recombinant human insulin (EXUBERA®) under OP, and lispro or 60 or 90 U of TI (A1) in the same order as for the meal challenge test for each individual subject. EGP was determined for each subject by measuring 6,6-$^2$H$_2$ glucose in the blood samples and applying the modified calculations by Hovorka et al. (ibid) for the non steady-state. Serum C-peptide concentrations were measured pre- and post-dose to assess endogenous insulin secretion. In addition, glucagon and free fatty acid concentrations were determined at regular intervals. All subjects were returned to their prior anti-diabetic treatment regimens at the end of each treatment visit.

Figure 3:
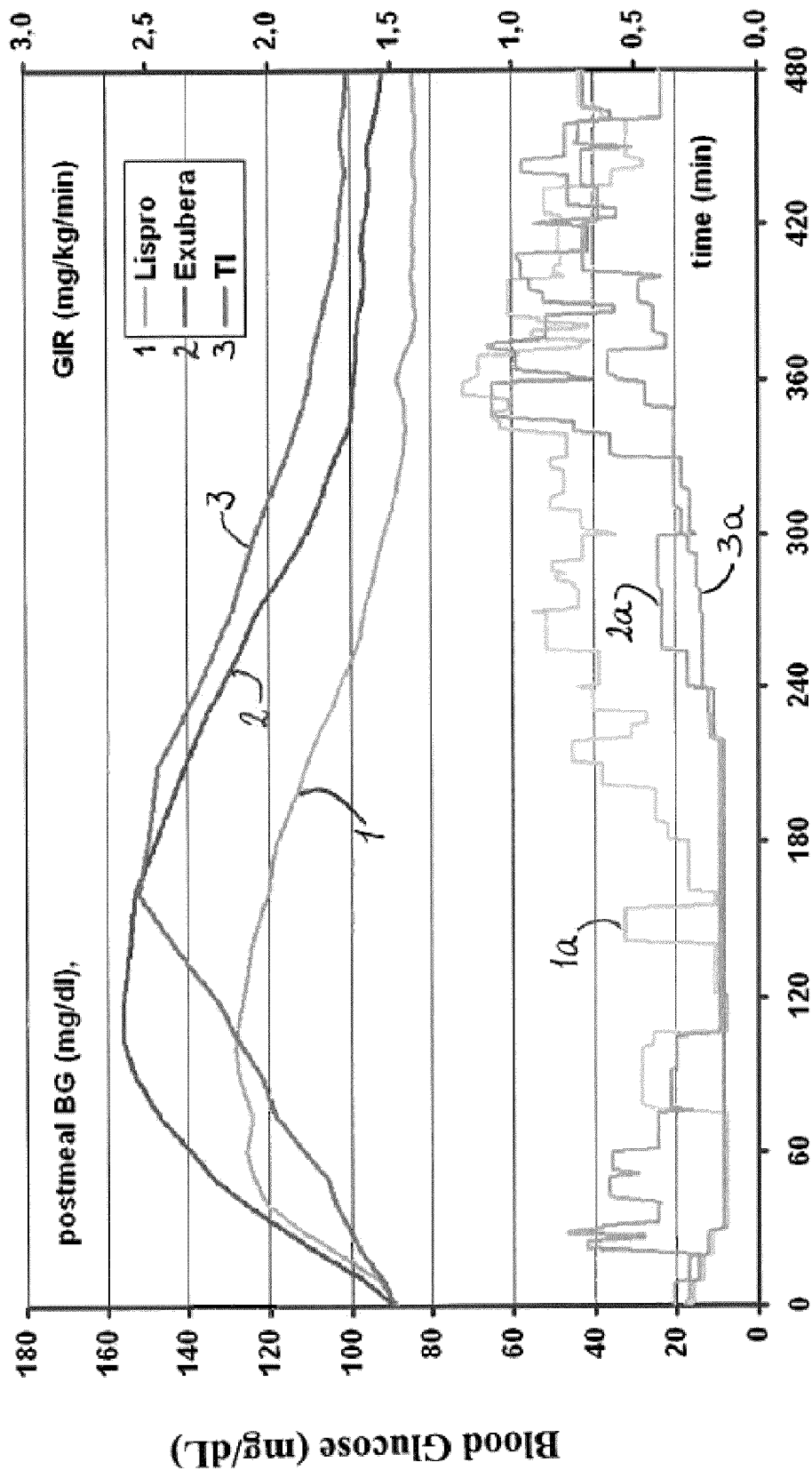
FIG. 3. is a graph of data obtained from a study in which blood glucose concentrations were measured at various times after a meal in patients with type 2 diabetes who were treated with insulin lispro (HUMALOG®, 1), EXUBERA® (2) and an insulin formulation comprising fumaryl diketopiperazine (insulin-FDKP, 3) at the onset of the meal. The graph also shows (line drawings at its bottom) the exogenous glucose infusions administered to the patients as needed to maintain euglycemic levels following administration of each of the treatments and indicated as 1a, 2a and 3a, respectively.

The results of the OP portion of the study are presented in FIGS. 3-6. FIG. 3 is a graphical representation of data plotted from blood sample values obtained from patients in this study. In particular, FIG. 3 shows measured blood glucose concentrations at various times after the meal challenge in patients with type 2 diabetes who were treated with insulin lispro (1), EXUBERA® (2) and an insulin formulation comprising fumaryl diketopiperazine (insulin-FDKP, TI, 3) at the onset of the meal. The time points in the data plots of each treatment curve represent the mean value for all samples analyzed in the study. The graph also shows the exogenous glucose infusions administered to the patients as needed during the experiments to maintain euglycemic (remain above 90 mg/dl of blood glucose) levels following administration of each of the treatments and represented in the graph as 1*a*, 2*a*, and 3*a*, respectively for insulin lispro, EXUBERA® and insulin-FDKP. As seen in FIG. 3, the glucose levels differ for all three treatments. It is evident from the data that the insulin lispro-treated subjects were overdosed due to the need to give the patients repeated glucose infusions to remain above 90 mg/dL. The graph also shows that subjects treated with insulin-FDKP had reduced glucose levels much earlier than the other treatments, with some subjects under this treatment requiring glucose infusions to remain above 90 mg/dL at early stages of the study. However, the insulin-FDKP treated subjects did not require further glucose infusion until about six hours after onset of treatment, which indicate that this treatment was effective at maintaining glycemic control for an extended period of time. The data also show that the glucose concentration was controlled in all subjects by all treatments, however, in subjects treated with insulin-FDKP, glucose control occurred more effectively from onset to about 120 minutes after treatment. Minimal glucose infusions were needed (following the initial phase) until after six hours following insulin-FDKP administration (when glucose demand is likely driven by the baseline insulin infusion) as compared to EXUBERA® and lispro treated subjects who were infused with glucose at about 4 and 3 hours respectively, post-treatment. The data indicate that patients treated with lispro and EXUBERA® may have reached hypoglycemic levels post-dosing if glucose were not infused. Hence, insulin-FDKP may be able to maintain the blood glucose above hypoglycemic levels more efficaciously than the other treatments for a longer period of time.

Figure 4:
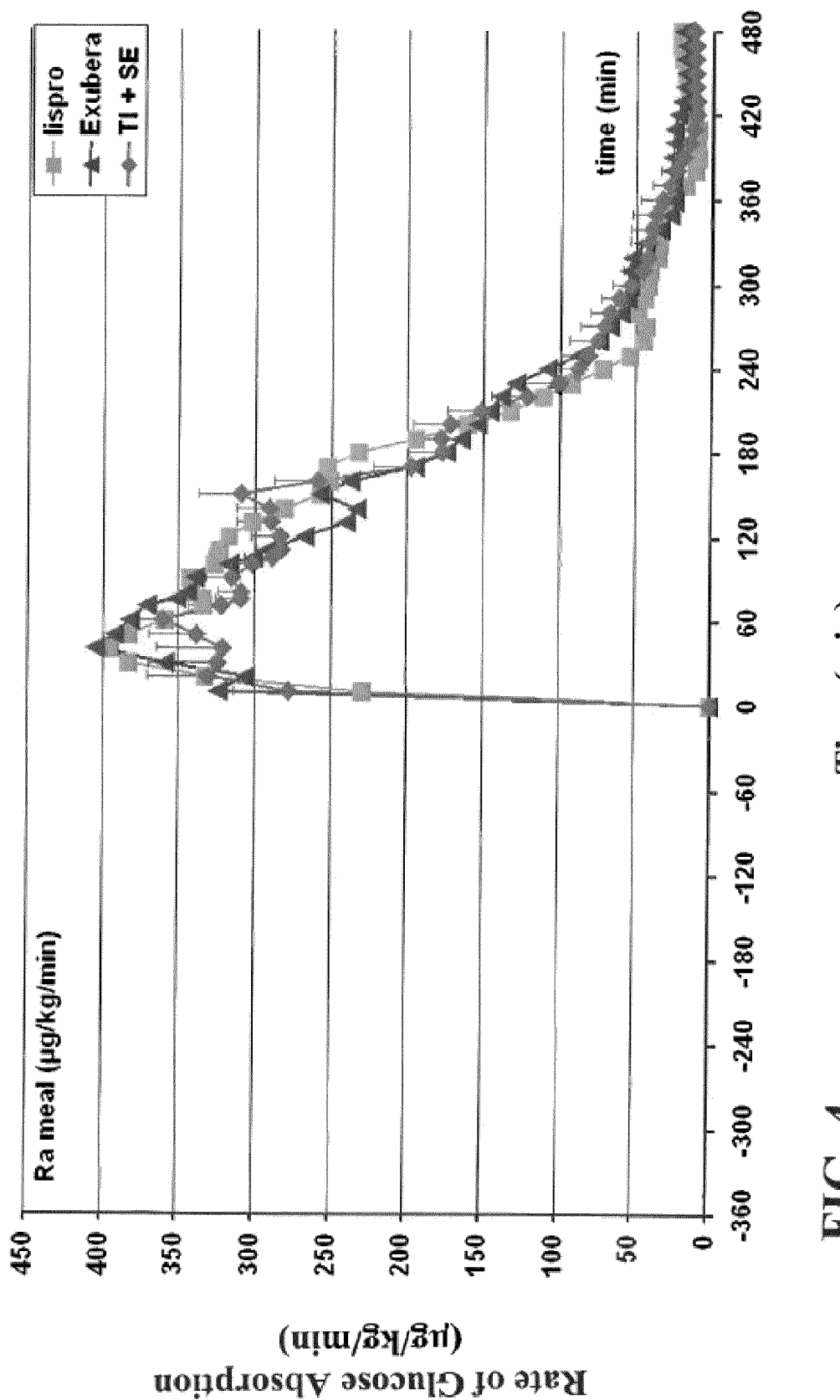
FIG. 4 is a graph of data obtained from a study which measured the rate of absorption of glucose for a period of time after a meal in patients with type 2 diabetes who were treated with insulin lispro, EXUBERA® and an insulin-FDKP formulation at the onset of the meal.

FIG. 4 is a graph of data obtained from the patients in the study described above showing the rate of absorption of glucose for a period of time after a meal in patients with type 2 diabetes who were treated with insulin lispro, EXUBERA® and an insulin-FDKP formulation immediately prior to of the meal. The time points in the data plots of each treatment curve represent the mean value for all samples analyzed in the experiments. The data in FIG. 4 show that the subjects treated with the three treatments all exhibited similar patterns for the rate of glucose absorption from the meal taken. Therefore, the data indicate that the treatment did not alter the rate of glucose absorption in the subjects treated from a meal.

Figure 5:
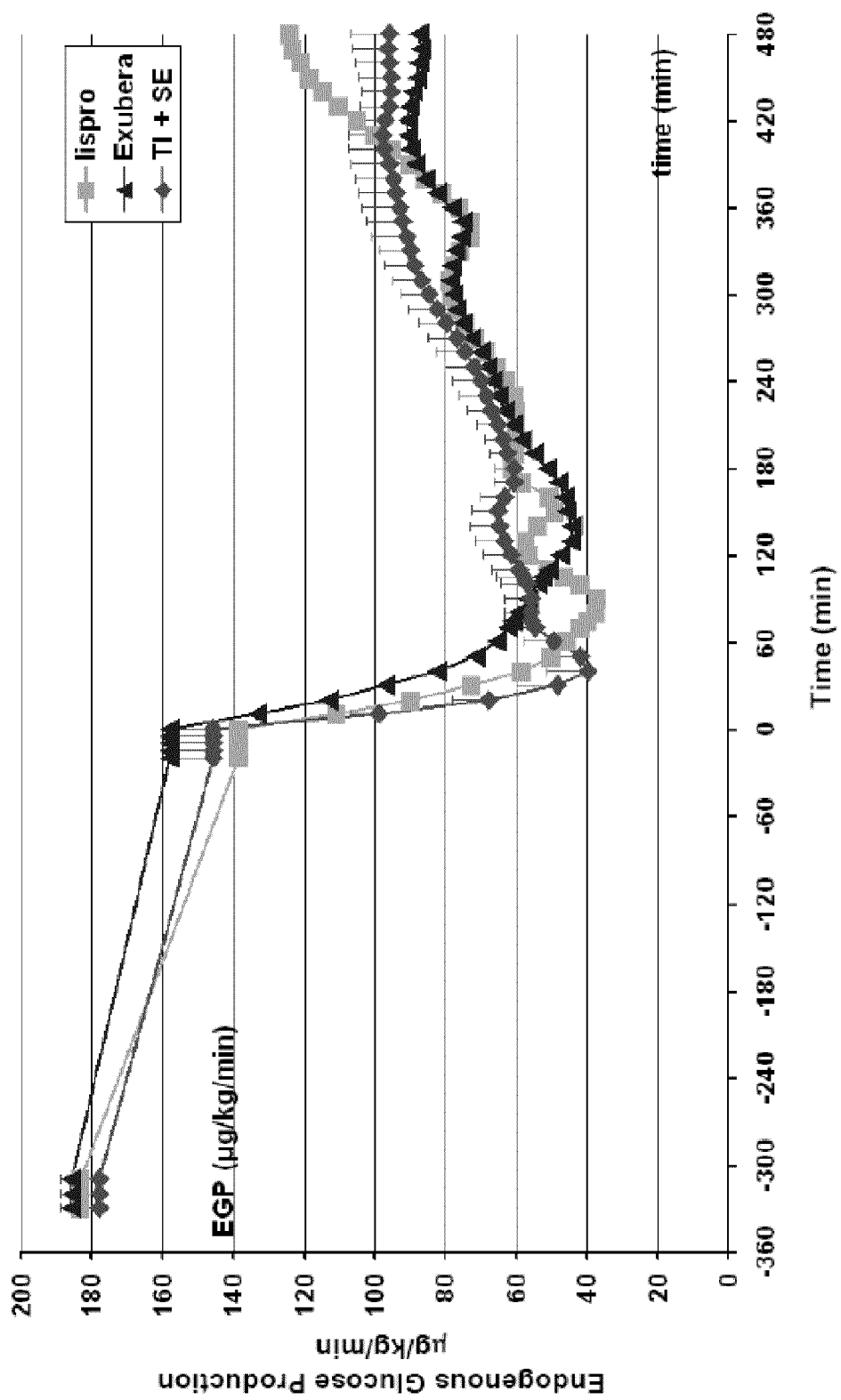
FIG. 5 is a graph of data obtained from a study in which endogenous glucose production after a meal was determined in patients with type 2 diabetes who were treated with insulin lispro, EXUBERA® and an insulin-FDKP formulation at the onset of the meal.

FIG. 5 is a graph of data obtained from experiments in which endogenous glucose production after a meal was determined in patients with type 2 diabetes who were treated with insulin lispro, EXUBERA® and an insulin-FDKP formulation at the onset of the meal. The time points in the data plots in each treatment curve represent the mean value for all samples analyzed in the experiments. The data curves for the three treatments show that all three treatments were effective in inhibiting endogenous glucose production in the treated subjects to a similar degree, suggesting a physiologic maximum for this effect. Notably subjects treated with insulin-FDKP exhibited peak inhibition of endogenous glucose production at a much faster or earlier time (at about 40 minutes) after treatment as compared to insulin lispro (at about 80 minutes) and EXUBERA® (at about 125 minutes).

Figure 6:
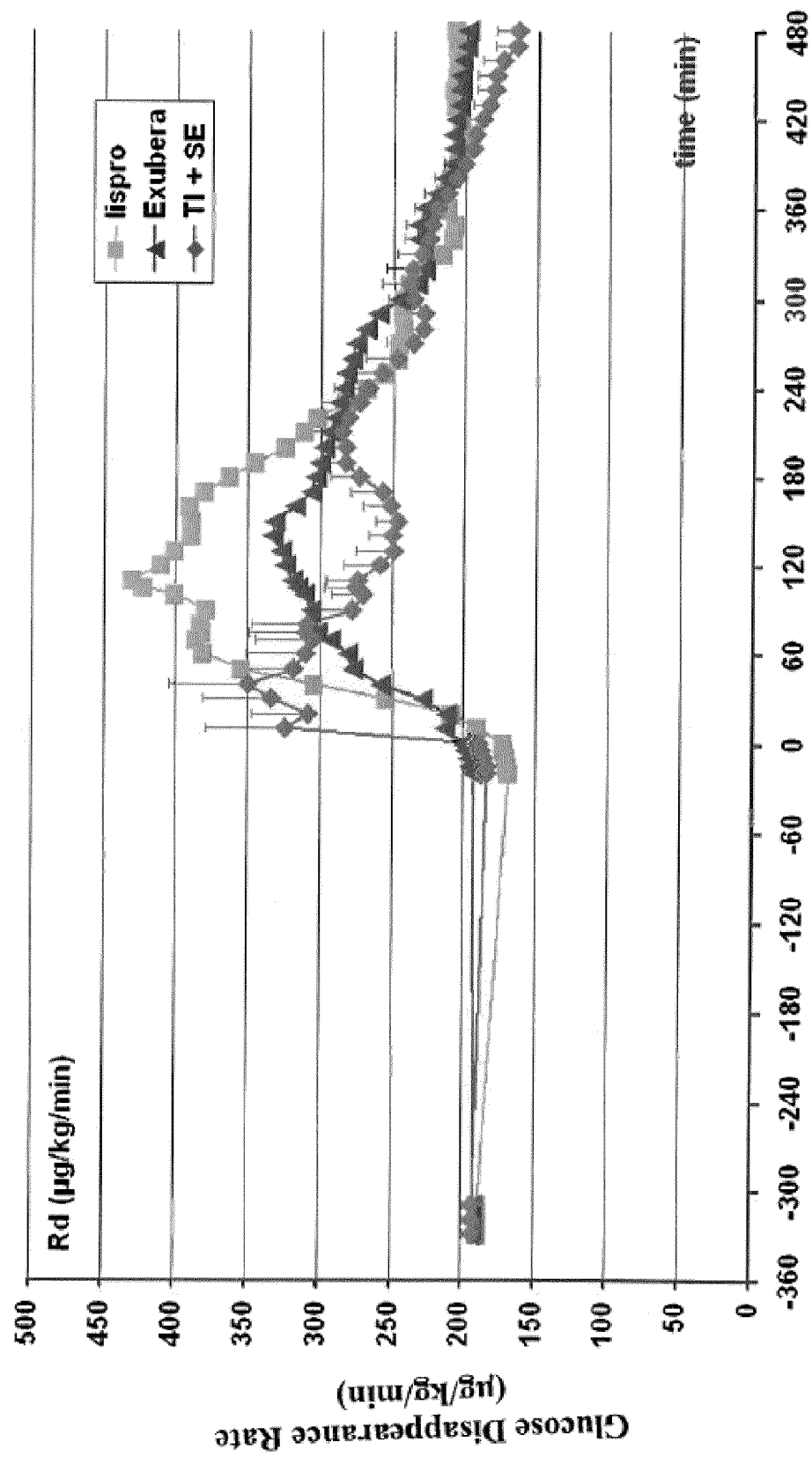
FIG. 6 is a graph of data obtained from a study which monitored for a period of time the rate of glucose disappearance in patients with type 2 diabetes, who were treated with insulin lispro, EXUBERA® and an insulin-FDKP formulation at the onset of the meal.

FIG. 6 is a graph of data obtained from experiments that monitored the rate of glucose disappearance for a period of time in subjects with type 2 diabetes, who were treated with insulin lispro, EXUBERA® and an insulin-FDKP formulation at the onset of the meal as described above. The time points in the data plots for each treatment curve represent the mean value for all samples analyzed in the experiments. In addition, the glucose disappearance rate was standardized to account for each subject's body weight by dividing the rate of glucose disappearance by the body weight of the subject. The data show that the rate of glucose disappearance or utilization for the subjects was different for all treatments. Notably, the glucose disappearance rate for insulin-FDKP was evidently much sooner than for insulin lispro or EXUBERA®. It was substantial at the first measurement after dosing, about 10 minutes post dosing, whereas the glucose disappearance rate for the others did not significantly depart from baseline until about 30 minutes. The glucose disappearance rate for insulin-FDKP peaked at about 40 minutes after dosing, much earlier as compared to insulin lispro (at about 120 minutes) and EXUBERA® (at about 150 minutes).

The study also indicated that measurements of C-peptide (data not shown) clearly show that an increase in C-peptide concentrations was delayed in the TI group when compared to lispro and EXUBERA®. This later increase in C-peptide (and endogenous insulin production), is related to the ability of each of the exogenous insulins to control the glucose absorbed from the meal, and appears to be related to the shape of the insulin profiles for each treatment group. The slow rise in insulin concentrations following EXUBERA® and lispro (median $t_{max}$ of 113 and 75 minutes, respectively, versus a $t_{max}$ of 20 minutes in the TI group, results in a decreased ability to control glucose early following the meal, and therefore, in an earlier increase in the patients' endogenous insulin response. The delay of endogenous insulin production in the TI group, however, indicates better control of blood glucose early in the study, when TI concentrations are high.

In summary, the data from the study indicate that insulin-FDKP was a markedly and surprisingly more efficacious treatment in patient with type 2 diabetes than existing treatments, i.e., insulin lispro and EXUBERA®, in that the insulin-FDKP treatment was faster at inhibiting endogenous glucose production and faster at inducing the glucose disappearance or utilization rate. It is surprising that EXUBERA® is so much slower in these parameters than even insulin lispro, to which it is otherwise kinetically similar. This further emphasizes the non-equivalence of these two inhalable insulin preparations (i.e. insulin-FDKP and EXUBERA®) already evident from their different kinetics.

Figure 7:
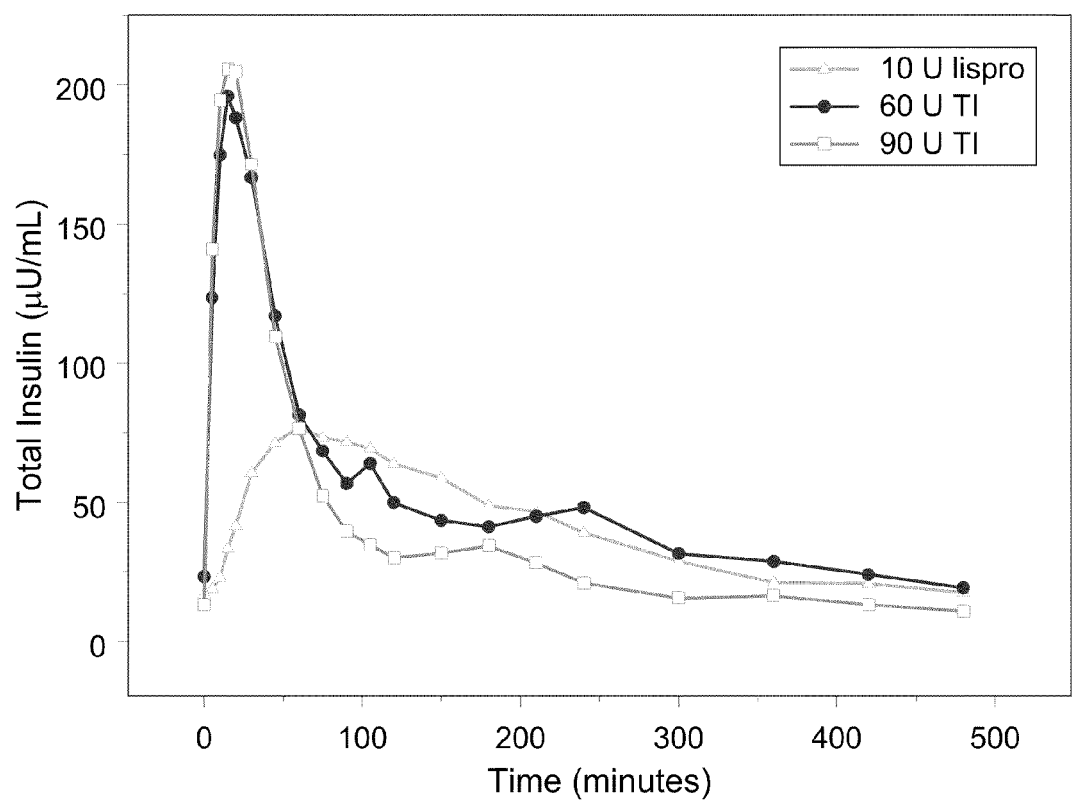
FIG. 7 depicts the mean insulin concentration-time profiles for patients with type 2 diabetes who were treated with insulin lispro nd 60 U or 90 U of an insulin-FDKP formulation at the onset of the meal from the glucose clamp study.

The results of the A1 portion of the study are presented in FIGS. 7-11. FIG. 7 is a graphical representation of data plotted from blood samples values obtained from subjects in this study. In particular, FIG. 7 shows the mean insulin concentration-time profiles for the three treatments. Total insulin concentrations (the sum of regular human insulin and lispro concentrations at each time point) are shown, as all of the insulin in the system is associated with the elicited response. Following both 60 and 90 U of insulin-FDKP administration, observed peak insulin concentrations are much higher (196 and 216 μU/mL following TI versus 83 μU/mL following lispro) and occur much earlier (median $t_{max}$ of 15 and 17.5 minutes following TI versus 60 minutes following lispro) when compared to peak insulin concentrations following lispro treatment. However, average exposure was very similar between the three groups, with total insulin AUC of 24,384, 18,616 and 19,575 μU/mL*min for the two TI dose groups and lispro, respectively.

Figure 8:
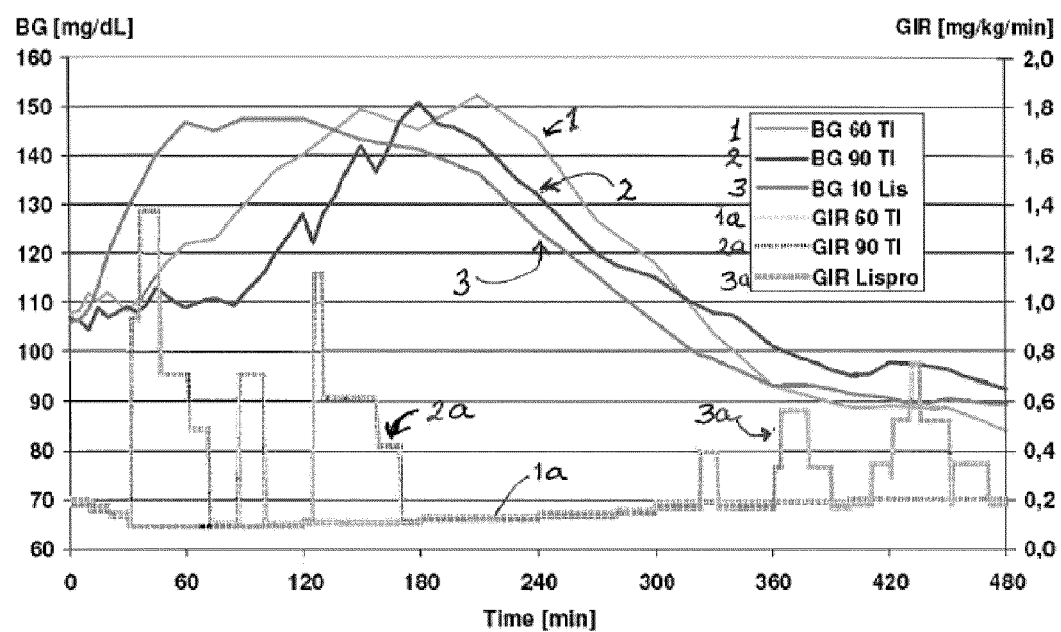
FIG. 8 depicts the blood glucose concentration of patients with type 2 diabetes who were treated with insulin lispro, 3), and 60 U (1) or 90 U (2) of an insulin-FDKP formulation at the onset of the meal from the glucose clamp study. The time of glucose infusion and amount of glucose infused is shown as 1a, 2a, and 3a respectively for 60 U and 90 U of an insulin-FDKP and insulin lispro.

FIG. 8 shows measured blood glucose concentrations at various times after the meal challenge in patients with type 2 diabetes who were treated with either 60 or 90 U of insulin formulation comprising fumaryl diketopiperazine (insulin-FDKP, 2, 3), and insulin lispro (1) at the onset of the meal. The time points in the data plots of each treatment curve represent the mean value for all samples analyzed in the study. The graph also shows the exogenous glucose infusions administered to the patients as needed during the experiments to maintain euglycemic (to remain above 75 mg/dL of blood glucose) levels following administration of each of the treatments and represented in the graph as 1a, 2a, and 3a, respectively for 60 and 90 U of insulin-FDKP, and insulin lispro, respectively. As seen in FIG. 7, the glucose profile shapes differ for all three treatments, however, maximal glucose levels are very similar, and glucose was controlled by all three treatments. The graph also shows that subjects treated with either dose of insulin-FDKP had reduced glucose levels much earlier than following lispro administration, with more efficacious glucose control occurring within the first 120-180 minutes post-dose. Subjects treated with both 90 U insulin-FDKP and lispro required some additional glucose infusions to maintain blood glucose at or above 75 mg/dL. Following 90 U TI, some subjects required additional glucose infusions in the earlier post-dose period, and following lispro, these infusions were needed in the latter period. This phenomenon can be due to the rapid glucose clearance rate observed in the patients treated with 90 U of insulin FDKP. Minimal glucose infusions were needed (following the initial phase) until the end of the study following insulin-FDKP administration (when glucose demand is likely due to the baseline insulin infusion) as compared to lispro treated subjects, who were infused with glucose between 5 and 8 hours post-treatment. This result is indicative of an elevated insulin presence and activity following lispro treatment in a timeframe well beyond expected glucose absorption following a meal. Additionally, it is evident that the 90 U insulin-FDKP group controlled blood glucose levels more efficiently than the group treated with the 60 U dose of insulin-FDKP, resulting in lower blood glucose levels in the 0-180 minute time period. Due to the better control, less endogenous insulin was secreted by the patients receiving the 90 U insulin-FDKP dose, and thus endogenous insulin contributed a small portion of the total insulin profile of the individuals in this group. Moreover, the data indicate that more endogenous insulin contributed to the total insulin profile of the group treated with 60 U dose of insulin-FDKP, making the average insulin profiles similar for the two groups tested.

Figure 9:
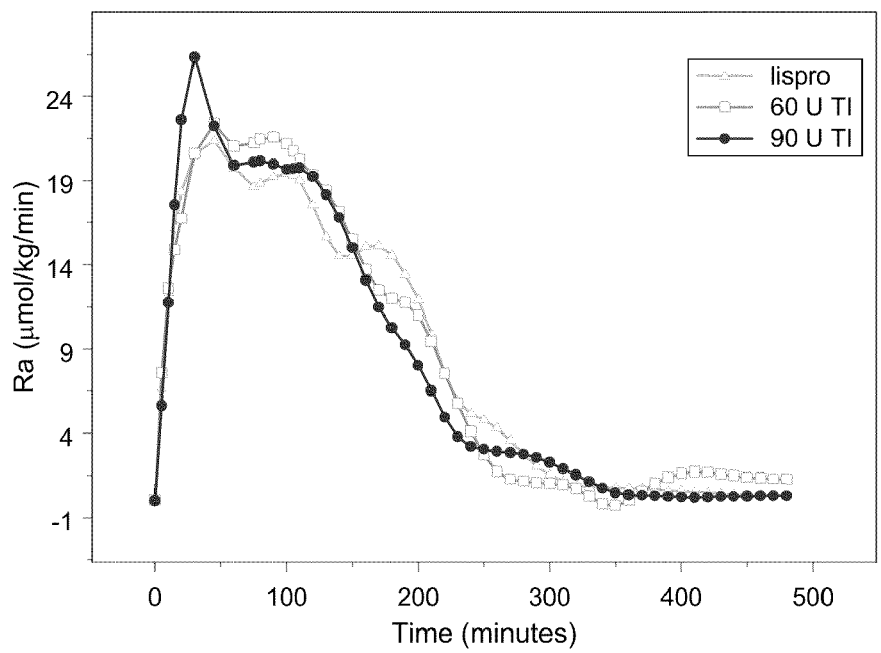
FIG. 9 is a graph of data obtained from a glucose clamp study which shows the rate of glucose absorption in the patients with type 2 diabetes treated with 60 U or 90 U of an insulin-FDKP and insulin lispro immediately prior to the meal.

FIG. 9 is a graph of data obtained from the patients in the study described above showing the rate of absorption of glucose for a period of time after a meal in patients with type 2 diabetes who were treated with 10 U insulin lispro, and 60 and 90 U of an insulin-FDKP formulation immediately prior to the meal. The time points in the data plots of each treatment curve represent the mean value for all samples analyzed in the experiments. The data in FIG. 9 show that the subjects treated with the three treatments all exhibited similar pattern of the rate of glucose absorption from the meal taken. Therefore, the data indicate that the treatment did not alter the rate of glucose absorption in the subjects treated from a meal.

Figure 10:
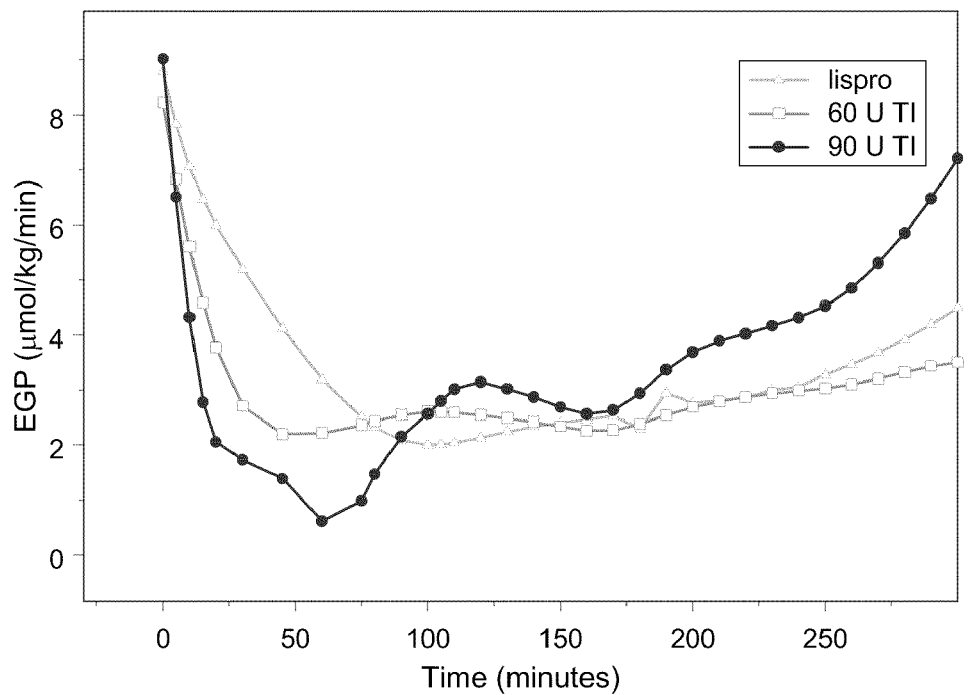
FIG. 10 is a graph of data obtained from a glucose clamp experiments in which endogenous glucose production after a meal was determined in patients with type 2 diabetes treated with 60 U or 90 U of an insulin-FDKP and insulin lispro at the onset of a meal.

FIG. 10 is a graph of data obtained from experiments in which endogenous glucose production after a meal was determined in patients with type 2 diabetes who were treated with 10 U of insulin lispro and either 60 or 90 U of an insulin-FDKP formulation at the onset of the meal. The time points in the data plots in each treatment curve represent the mean value for all samples analyzed in the experiments. Two subjects treated with 90 U insulin-FDKP were excluded from the analysis due to difficulty in interpreting the modeled results. The data curves for the three treatments show that all three treatments were effective in inhibiting endogenous glucose production in the treated subjects, to a similar degree between the 60 U insulin-FDKP and 10 U lispro treatments. The data also indicate that the 90 U insulin-FDKP treatment has a greater and faster effect on inhibiting endogenous glucose production. Notably subjects treated with insulin-FDKP exhibited peak inhibition of endogenous glucose production at a much faster or earlier time (at about 40 and 60 minutes for the two treatments) following dosing, than insulin lispro (at about 100 minutes).

Figure 11:
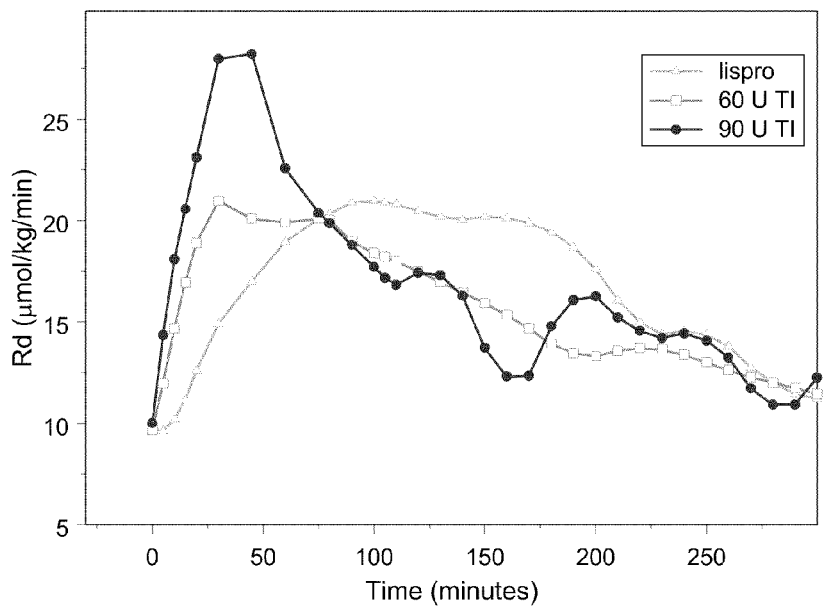
FIG. 11 is a graph of data obtained from experiments that monitored the rate of glucose disappearance for a period of time in subjects with type 2 diabetes treated with 60 U or 90 U of an insulin-FDKP and insulin lispro at the onset of a meal.

FIG. 11 is a graph of data obtained from experiments that monitored the rate of glucose disappearance for a period of time in subjects with type 2 diabetes, who were treated with 10 U of insulin lispro and either 60 or 90 U of an insulin-FDKP formulation at the onset of the meal as described above. The time points in the data plots for each treatment curve represent the mean value for all samples analyzed in the experiments. In addition, the glucose disappearance rate was standardized to account for each subject's body weight by dividing the rate of glucose disappearance by the body weight of the subject. The data show that the rate of glucose disappearance or utilization for the subjects was different for all treatments. Notably, the glucose disappearance rate for both the 60 U and 90 U insulin-FDKP dose groups was evident much earlier than for insulin lispro. The glucose disappearance rate of the insulin-FDKP treated groups was substantial at the first measurement after dosing, about 5 minutes post dosing, and peaked at about 30-50 minutes after dosing, much earlier as compared to insulin lispro (at about 100 minutes).

In summary, the data from the study indicate that insulin-FDKP was markedly a more efficacious treatment in patient with type 2 diabetes than existing treatments, i.e., insulin lispro, in that the insulin-FDKP treatment was faster at inhibiting endogenous glucose production and faster at inducing the glucose disappearance or utilization rate in patients with type 2 diabetes. Insulin-FDKP effect on EGP and glucose utilization appeared to increase with increasing dose.

Example 2

A Prospective, Multi-Center, Open-Label, Randomized, Controlled Clinical Trial Comparing the Efficacy and Safety in Subjects with Type 1 Diabetes Receiving SC Basal Insulin and Prandial Inhalation of Insulin-FDKP Versus SC Basal and Prandial Insulin Over a 52-Week Treatment Period and a 4-Week Follow-Up This was a prospective, multi-country, multicenter, open label, randomized, controlled clinical trial comparing glycemic control in subjects with type 1 diabetes receiving basal insulin and prandial insulin-FDKP (TI) Inhalation Powder (TI Inhalation Powder group) with subjects receiving basal insulin and SC rapid-acting insulin aspart (comparator group). This study included a 52-week treatment phase and a 4-week follow-up phase. During the 4-week follow-up phase, pulmonary function and select clinical laboratory assessments were scheduled.

The study began with enrollment at Week-3. Subjects received a complete battery of safety and eligibility assessments, including HbA1c and fasting plasma glucose (FPG).

At Week-1, subjects were randomized to one of the following 2 treatments:

Basal insulin+prandial TI Inhalation Powder
Basal insulin+prandial SC rapid-acting insulin At Week-1, subjects again completed the first three components of the Insulin Treatment Questionnaire (ITQ) for the purpose of assessing test-retest reliability only). After completing the questionnaire, subjects randomized to the TI Inhalation Powder group were trained on the MEDTONE® Inhaler using TECHNOSPHERE®/insulin (insulin-FDKP) inhalation powder; subjects in the comparator group were trained in the use of the NOVOLOG® pens; all subjects were trained in administration of LANTUS®. Additionally, all subjects were trained on a blood glucose monitoring (HBGM) meter provided at the beginning of the trial and diary and received diabetes education. Any training was repeated at Week 0, if needed.

At the beginning of the treatment phase, subjects had several titration/dose evaluation visits to adjust insulin therapy. Titration visits occurred once a week for the first 4 weeks. During Weeks 4 through 10, there were three telephone "visits" (at Week 6, Week 8, and Week 10) to titrate dose, if necessary. However, dose titration was allowed throughout the trial.

All subjects completed a 7-point blood glucose profile on any 3 days during the week immediately preceding each visit from Week 0 to Week 52. The 7 time points included samples from before breakfast and 2 hours after breakfast, before the mid-day meal and 2 hours after the mid-day meal, before the evening meal and 2 hours after the evening meal and at bedtime (7 time points a day, over 3 days). These blood glucose (BG) values were recorded in the HBGM diary that was collected at clinic visits. The diaries for Weeks 4 through 10 (during dose titration) which were discussed over the telephone were collected at the next office visits.

A meal challenge test was performed at Week 4 (during dose titration), Week 26, and Week 52. Meal challenge venous blood sampling times were: −30, 0, 30, 60, 90, 105, 120, 180, 240, 300, and 360 minutes. Blood glucose (BG) was also measured using HBGM glucose meters to aid the Investigator in treatment decisions and values were obtained at −30, 0, 60, and 120 minutes during the meal challenge.

Treatments for glycemic control used in the trial were the following: prandial insulin-FDKP (TI) inhalation powder, prandial insulin aspart, and basal insulin glargine. Subjects assigned to the TI Inhalation Powder group (TI Inhalation Powder in combination with basal insulin therapy) received sc basal insulin glargine (LANTUS®) once daily (at bedtime) and inhaled TI Inhalation Powder 3 to 4 times a day, immediately before main meals or a snack as based upon clinical need. Adjustment of the TI Inhalation Powder dose and frequency of use to greater than 3 times a day was at the discretion of the Investigator. Subjects in the comparator group received SC basal insulin glargine once daily (at bedtime) and SC injection of rapid acting insulin (NOVOLOG®) 3 to 4 times per day, immediately before main meals (no later than 10 minutes before meals).

The primary objective of this trial was to compare the efficacy over 52 weeks of TI Inhalation Powder+basal insulin versus insulin aspart+basal insulin as assessed by change from baseline in HbA1c (%). A total of 565 subjects were studied in sites in the United States, Europe, Russia, and Latin America. A total of 293 subjects received TI Inhalation Powder+basal insulin, and 272 subjects received insulin aspart+basal insulin.

The primary efficacy endpoint was assessed using pre-specified ANCOVA and Mixed Model with Repeated Measures (MMRM) analyses. Due to disproportionate dropouts between the TI Inhalation Powder+basal insulin treatment arm and the insulin aspart+basal insulin treatment arm, the assumption of missing completely at random for the ANCOVA model was violated. As such, the MMRM was used as a secondary confirmation. TI Inhalation Powder met the primary endpoint of non-inferiority in the MMRM model, although not in the ANCOVA model. The mean change from baseline over 52 weeks was comparable in both treatment groups, with a Least Square Means treatment difference of −0.25% in favor of insulin aspart. Based on results from both models, there was not a clinically significant difference between treatment groups in mean change from baseline in HbA1c. Indeed, a comparable percentage of subjects reached HbA1c target levels in the 2 treatment groups. There were no statistically significant differences in the percentage of subjects whose HbA1c level decreased to ≦8.0% (50.99% for the TI Inhalation Powder group, 56.16% for the comparator group); ≦7.0% (16.34%, TI Inhalation Powder group; 15.98%, comparator group); and ≦6.5% (7.43%, TI Inhalation Powder group; 7.31%, comparator group).

The reduction in HbA1c was comparable between groups and sustained over 52 weeks. Subjects in the TI arm dropped to 8.21 (SD 1.15) % at Week 14 from a baseline of 8.41 (SD 0.92) %; the reduction was maintained at Week52 (8.20 [SD 1.22] %). Subjects in the insulin aspart arm dropped to 8.07 (SD 1.09) % at Week 14 from a baseline of 8.48 (SD 0.97) %; the reduction was maintained at Week 52 (7.99 [SD 1.07] %).

When the analysis of the change from baseline in HbA1c was corrected for the last 3 months of insulin glargine exposure in an ANCOVA model, no effect due to glargine exposure was found.

Over the 52-week treatment period, fasting plasma glucose (FPG) levels decreased significantly (p=0.0012) in the TI Inhalation Powder group compared to FPG levels in subjects using insulin aspart, despite similar dose levels of basal insulin in both groups at both start and end points of the trial. In the TI Inhalation Powder group, mean FPG decreased 44.9 (SD 104.7) mg/dL from 187.6 (SD 85.1) mg/dL at baseline to 140.1 (SD 72.1) mg/dL at the end of the treatment period, compared to a smaller drop of 23.4 (SD 103.1) mg/dL from 180.8 (SD 86.9) mg/dL at baseline to 161.3 (SD 68.2) mg/dL over the same period in the comparator group.

A secondary efficacy endpoint was the percentage of subjects with a 2-hour postprandial plasma glucose (PPG) <140 mg/dL and <180 mg/dL after a meal challenge. Subjects with 2-hour PPG values in both categories were comparable in each treatment group at Weeks 26 and 52. Absolute values for PPG $C_{max}$ at Baseline and Week 52 were the same in both treatment groups.

Subjects in the TI Inhalation Powder group lost an average of 0.5 kg over the 52-week treatment period compared to an average gain of 1.4 kg observed in the comparator group. The difference between groups was statistically significant (p<0.0001) with a treatment difference of −1.8 kg. The mean change from Baseline (Week 0) in body weight was not statistically significant for the TI arm (p=0.1102), while the mean body weight gain for the insulin aspart arm was significant (p<0.0001).

Overall, comparable levels of HbA1c and postprandial blood glucose levels were achieved in both arms of the trial; however TI Inhalation Powder-treated subjects did so in the context of weight neutrality and with more effective control of fasting blood glucose.

TI Inhalation Powder was well-tolerated over 52 weeks of treatment. The safety profile of TI Inhalation Powder was similar to that observed in earlier trials in the TI Inhalation Powder clinical development program; no safety signals emerged over the course of the trial. No pulmonary neoplasms were reported. There was no statistical difference between TI Inhalation Powder treatment and comparator with respect to change from baseline in $FEV_1$ (forced expiratory volume in one second), FVC (forced vital capacity), and TLC (total lung capacity). The most common adverse events in the trial in TI Inhalation Powder-treated subjects were mild to moderate hypoglycemia and transient, mild, non-productive cough.

Figure 12:
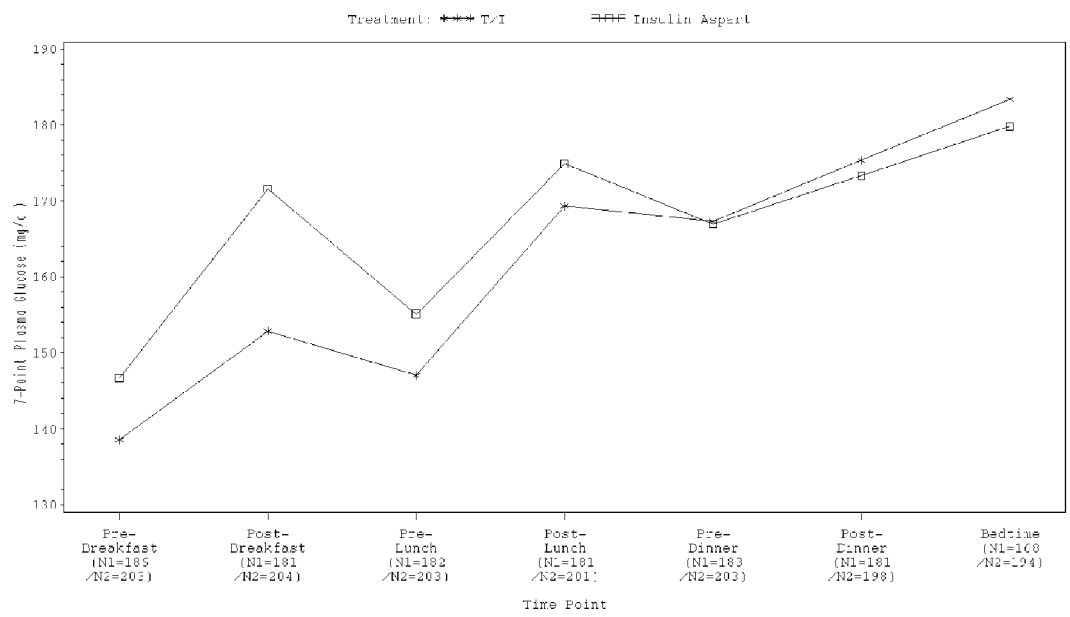
FIG. 12 is a graph of data from a study comparing usage of insulin-FDKP and insulin glargine to insulin aspart and insulin glargine presenting 7-point blood glucose profiles in the $52^{nd}$ week of the study.
Figure 13:
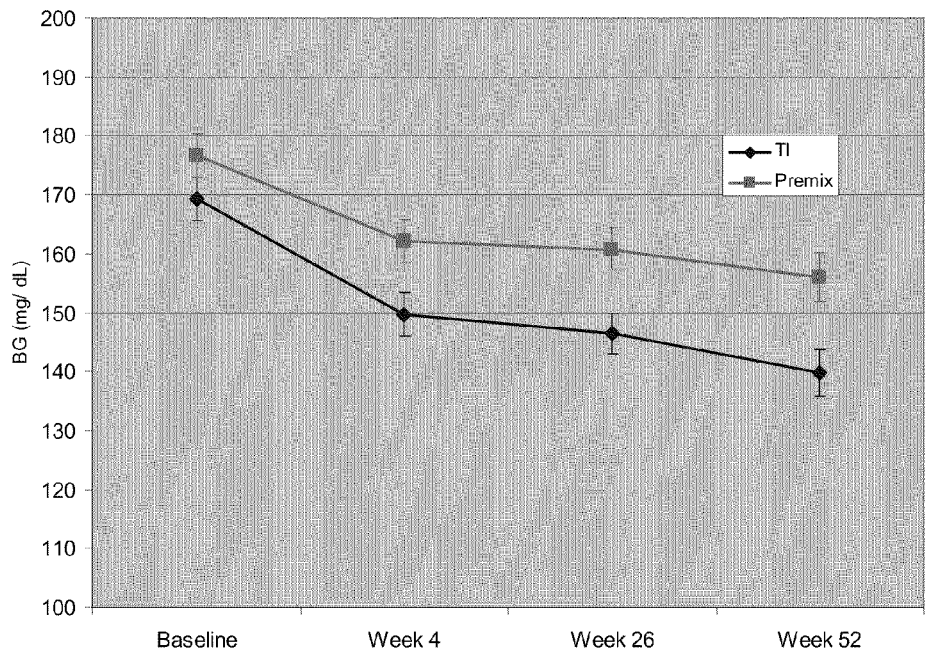
FIG. 13 is a graph depicting data from experiments measuring fasting blood glucose levels in blood samples from subjects treated with subcutaneous injections of a basal insulin (insulin glargine/LANTUS®) at bedtime, and insulin-FDKP administered prandially by pulmonary inhalation. The graph also shows data of a comparison group, i.e., subjects treated with NOVOLOG® mix 70/30 (premix) at breakfast and dinner as recommended by the manufacturer. The subjects were all diagnosed as patients with suboptimally controlled type 2 diabetes, who had been previously treated with regimens of subcutaneous insulins with or without anti-hyperglycemic agents.

Seven-point BG profiles were derived from HBGM; data collected at all specified time points are presented in FIG. 12 for the ITT and PP Populations, respectively. No inferential statistics were performed.

FIG. 12 presents the 7-point BG profile at Week 52 for both treatment arms. Pre-breakfast baseline values were lower in the TI arm as expected from the Week 52 FPG values: 139.1 (SD 72.6) mg/dL for the TI arm vs. 49.5 (SD 80.2) mg/dL for the aspart arm. From pre-breakfast to pre-lunch, BG values were lower in the TI arm. However, from post-lunch through bedtime, mean daily BG values were similar in both treatment groups. Concordant results were observed in the PP Population (data not shown). There was a parallel and steady increase in BG from pre-dinner to bedtime in both treatment arms that was likely a result of the suboptimal dosing with insulin glargine. Bedtime dosing with insulin glargine may not provide full 24-hour coverage in all subjects with type 1 diabetes (Barnett A. Vascular Health and Risk Management 2:59-67, 2006;) (LANTUS® was administered once daily by label). Although there was a rise in underlying baseline blood glucose in both treatment arms both in the evening and throughout the day the effect is more pronounced in the TI treatment arm.

Example 3

Figure 14:
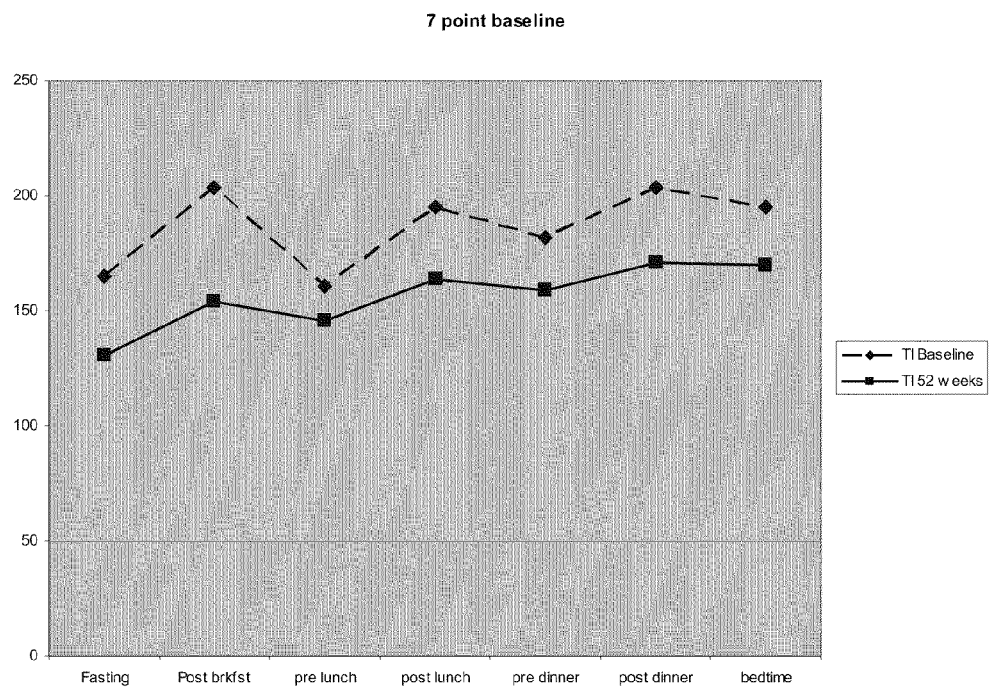
FIG. 14 is a graph depicting data from experiments measuring mean blood glucose levels from samples taken at seven points during the day, i.e., fasting, post-breakfast, pre-lunch, post-lunch, pre-dinner, post-dinner and bedtime for three days during the indicated week, in subjects treated with insulin glargine at bedtime and prandial insulin-FDKP by pulmonary inhalation at the first week of treatment, (hatched lines; baseline) and during the 52nd week (solid line) of treatment. The data show a rise in blood glucose concentration in subjects with type 2 diabetes throughout the day, however, at 52 weeks, the data indicate that the blood glucose levels were significantly lower that at the onset of the treatments and better controlled.

A Prospective, Multi-Center, Open-Label, Randomized, Controlled Clinical Trial Comparing the Efficacy and Safety in Subjects With T2 DM Receiving SC Basal Insulin and Prandial Inhalation of TI vs. SC Premixed Insulin Therapy Over a 52-Week Treatment Period and 4-Wk Follow-Up This trial compared the efficacy as expressed by change in HbA1c over a 52-week period of prandial administration of TI Inhalation Powder in combination with basal insulin therapy (TI group) versus a premix of intermediate-acting and rapid-acting insulin (comparator group) in subjects with suboptimally controlled type 2 diabetes, previously treated with regimens of sc insulins±oral anti-hyperglycemic agents. The reduction in HbA1c was comparable between TI+basal insulin and premixed insulin. The percent of responders for an end of study HbA1c≦7.0% was comparable and not statistically different between the TI+basal insulin and premixed insulin groups. Notably fasting blood glucose was reduced significantly by treatment with TI+basal insulin as compared to premixed insulin (see FIG. 13) Additionally both fasting blood glucose and glucose excursions were reduced for the TI+basal insulin group between the beginning and end of the treatment period (See FIG. 14). As noted in Example 2 baseline blood glucose levels trended upward over the course of the day for TI+basal insulin (see FIG. 14).

Example 4

Figure 15:
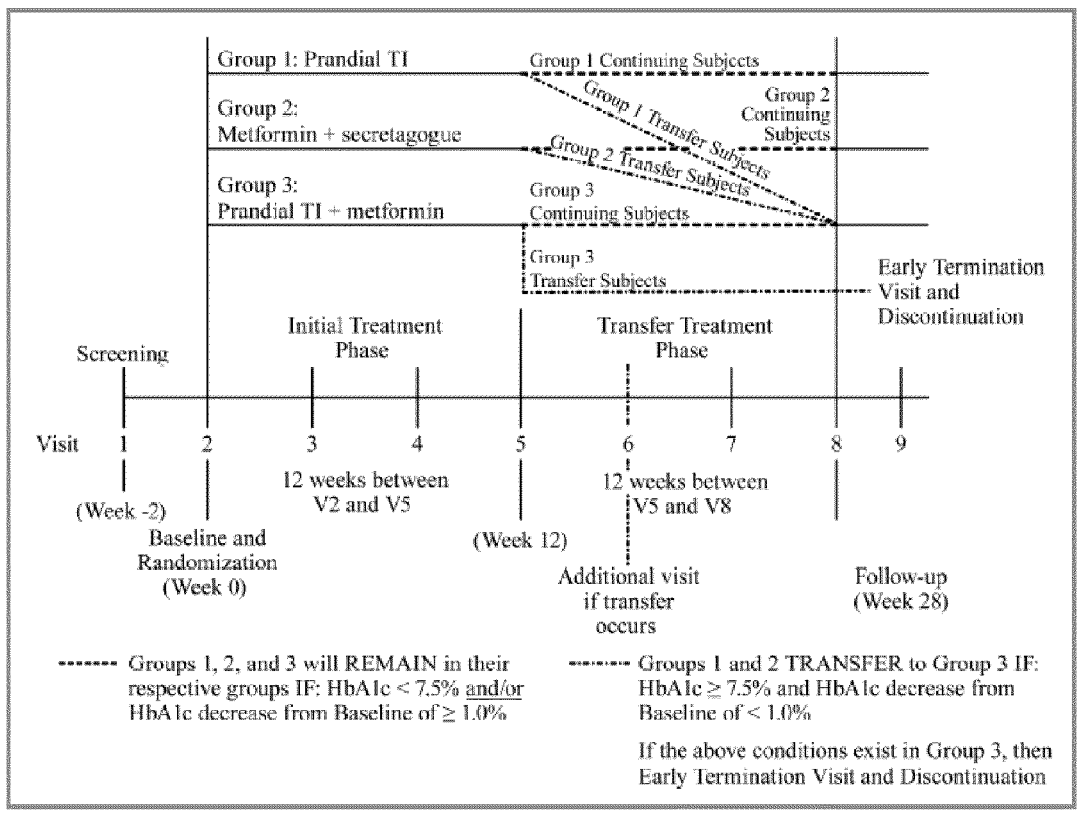
FIG. 15 depicts the trial design of a clinical study comparing prandial TI (insulin-FDKP) (Group 1) with metformin+a secretagogue (Group 2) and prandial TI+metformin (Group 3).

This study was a phase 3, 24-week, open-label trial designed to evaluate the efficacy and safety of prandial TECHNOSPHERE®/Insulin (insulin-FDKP, TI) alone or in combination with metformin versus metformin and a secretagogue, a current standard of care regimen, in subjects with type 2 diabetes mellitus sub-optimally controlled on combination metformin and secretagogue. FIGS. 15 and 16 depict the trial design of the clinical study and the baseline demographics of patients enrolled in the study. Subjects were randomized 1:1:1 to one of the 3 treatment groups and received anti-diabetic treatment based on their randomization group for the first 12 weeks; the subsequent 12 weeks of the trial were considered an observational period.

The trial design was unusual in that there was not a formal run-in period to titrate study medications. Subjects had a total of only 12 weeks of treatment to titrate to an effective dose of study medication before an assessment of the primary efficacy endpoint was conducted. Subjects with continued sub-optimal control after 12 weeks of therapy, in any of the 3 treatment groups, were required to either switch to TI+metformin or discontinue participation in the trial. The total duration of the treatment period was 24 weeks.

This was not a treat-to-target trial and investigators were not given a specific HbA1c or fasting plasma glucose (FPG) goal to treat to. Investigators were allowed to titrate TI at their clinical discretion with upper limits specified for preprandial, postprandial, and bedtime blood glucose, but without a fixed dose schedule. Although the protocol allowed titration of up to 90 U TI per meal, the mean per meal dose of TI was ~65 U at trial endpoint, suggesting that investigators may have been reluctant to titrate upward.

In a head-to-head comparison of prandial TI alone or in combination with metformin vs. a commonly used antihyperglycemic regimen. All three treatment groups showed statistically and clinically significant reductions in HbA1c levels over the course of the study. TI was comparable with respect to HbA1c and FPG reduction and significantly more effective with respect to postprandial control—both in formal meal challenges and in self monitored glucose profiles. Subjects treated with prandial TI alone or in combination with metformin over 24 weeks had mean weight loss. The ultrarapid pharmacokinetics of TI may synchronize insulin levels with the post-meal rise in blood glucose, thereby preventing overinsulinization and concomitant weight gain.

TI alone or in combination with metformin was well-tolerated over 24 weeks of treatment. FIGS. 17-28 depict the results of the study. The safety profile of TI was similar to that observed in earlier trials in the TI clinical development program; no safety signals emerged over the course of the trial. Very low rates of severe hypoglycemia were observed in all treatment groups with no cases occurring in patients treated with TI alone or with oral hypoglycemics and in 2% of patients when TI and metformin were combined. Even with such marked reductions in HbA1c overall, no increases in weight were seen. Detailed assessment of pulmonary safety including FEv1 and DLCO over the 24 weeks of the study showed no difference in pulmonary function between patients inhaling TI and those on oral therapy alone.

TI+Metformin

For those subjects that completed the trial, prandial TI+metformin provided a clinically significant mean reduction from baseline in HbA1c (−1.68 [1.0] %) after 24 weeks of treatment, comparable to that of a standard anti-hyperglycemic regimen. However, TI+metformin provided statistically superior postprandial control compared to metformin+secretagogue after 12 and 24 weeks of treatment and a comparable mean reduction from baseline in FPG after 24 weeks. There was mean weight loss (−0.75 kg) over 24 weeks in this treatment group and an overall incidence of mild-to-moderate hypoglycemia of 35.0%.

TI Alone

For those subjects that completed the trial, prandial TI alone was successful in providing a clinically significant mean reduction from baseline in HbA1c (1.82 [1.1] %) after 24 weeks of treatment. The change from baseline was numerically superior to the standard anti-hyperglycemic regimen of metformin+secretagogue. At trial endpoint, TI alone provided significantly more effective postprandial control than comparator with a comparable mean reduction from baseline in FPG. There was net weight loss (−0.04 kg) over 24 weeks in this treatment group and an overall incidence of mild-to-moderate hypoglycemia of 27.6%.

Metformin+Secretagogue

Figure 17:
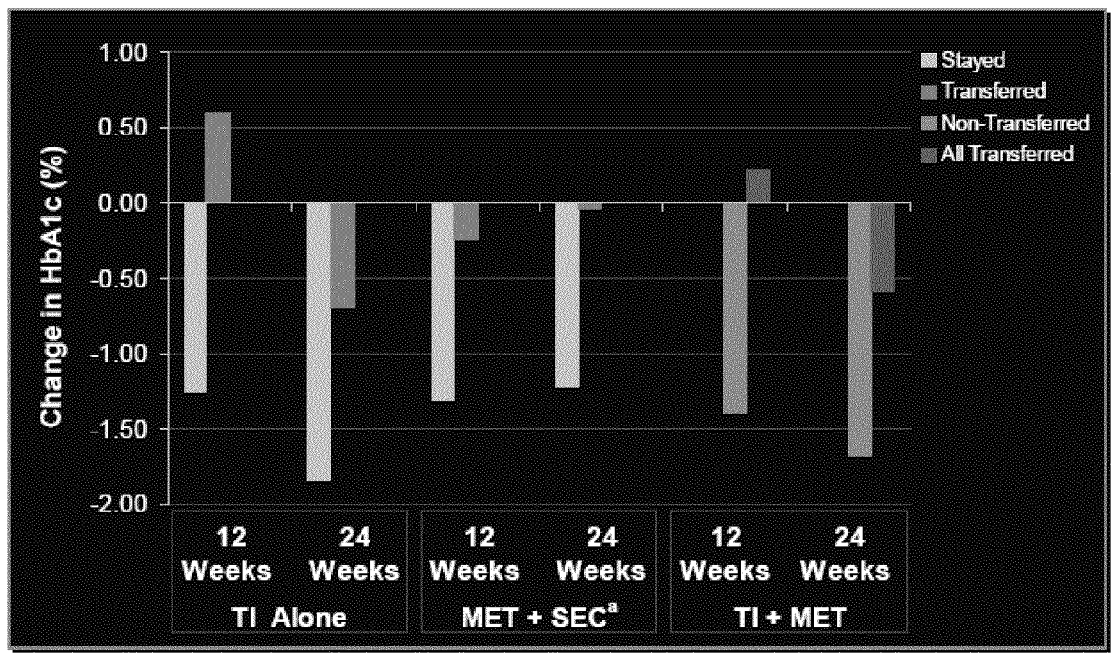
FIG. 17 depicts lowering of HbA1c at 12 and 24 weeks after treatment with TI alone, TI and metformin, or metformin and a secretagogue. The terms "stayed," "transferred," "non-transferred," and "all transferred" are defined in FIG. 15.
Figure 18:
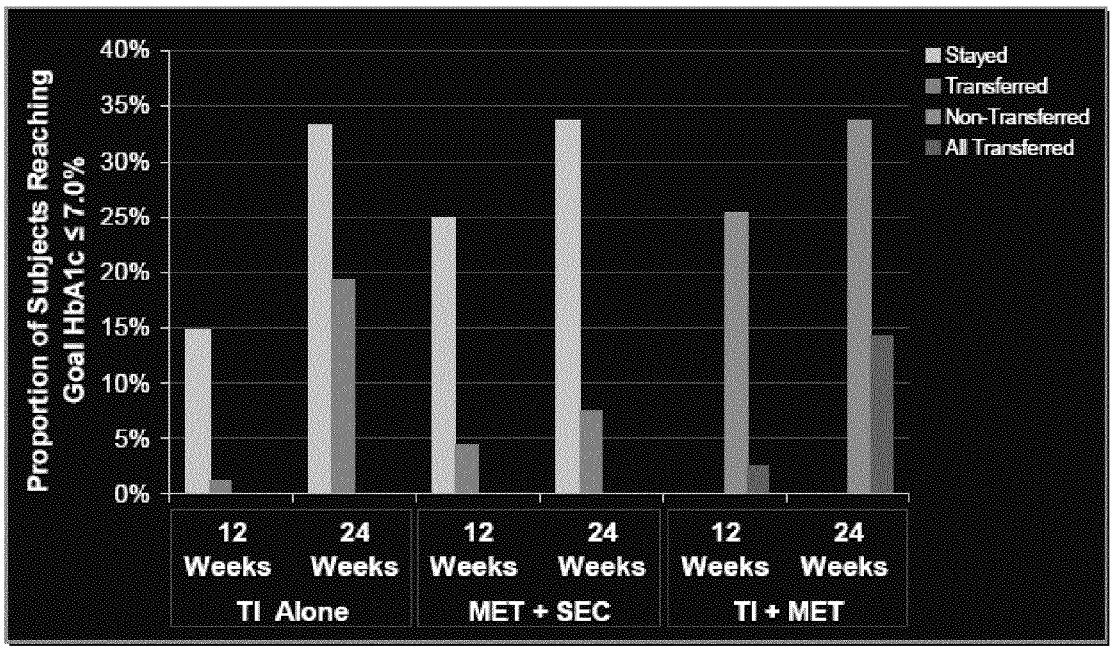
FIG. 18 depicts the proportion of patients reaching their HbA1c goal of ≦7% at 12 and 24 weeks after treatment with TI alone, TI and metformin, or metformin and a secretagogue.
Figure 19:
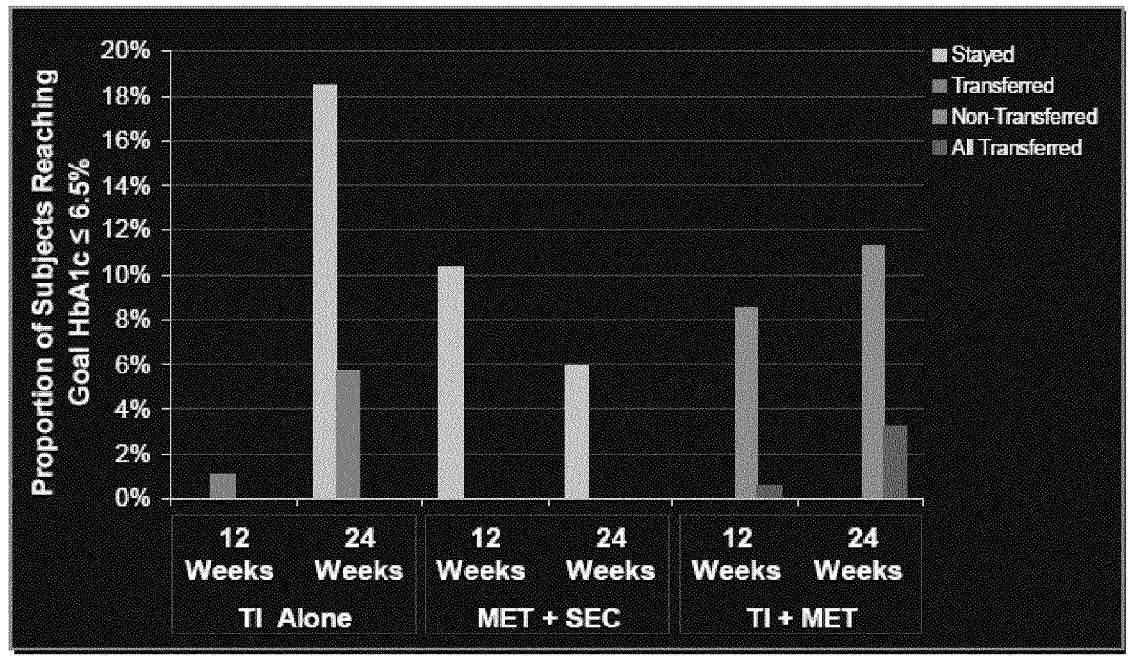
FIG. 19 depicts the proportion of patients reaching their HbA1c goal of ≦6.5% at 12 and 24 weeks after treatment with TI alone, TI and metformin, or metformin and a secretagogue.
Figure 20:
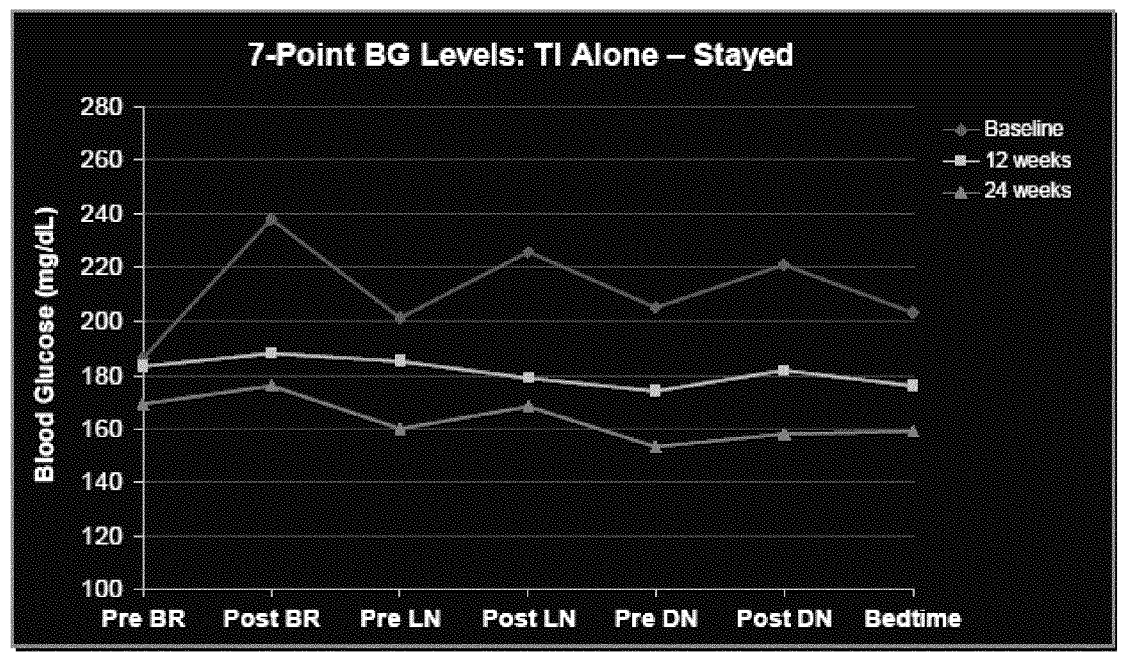
FIG. 20 depicts blood glucose levels after 12 and 24 weeks of treatment with TI alone.
Figure 21:
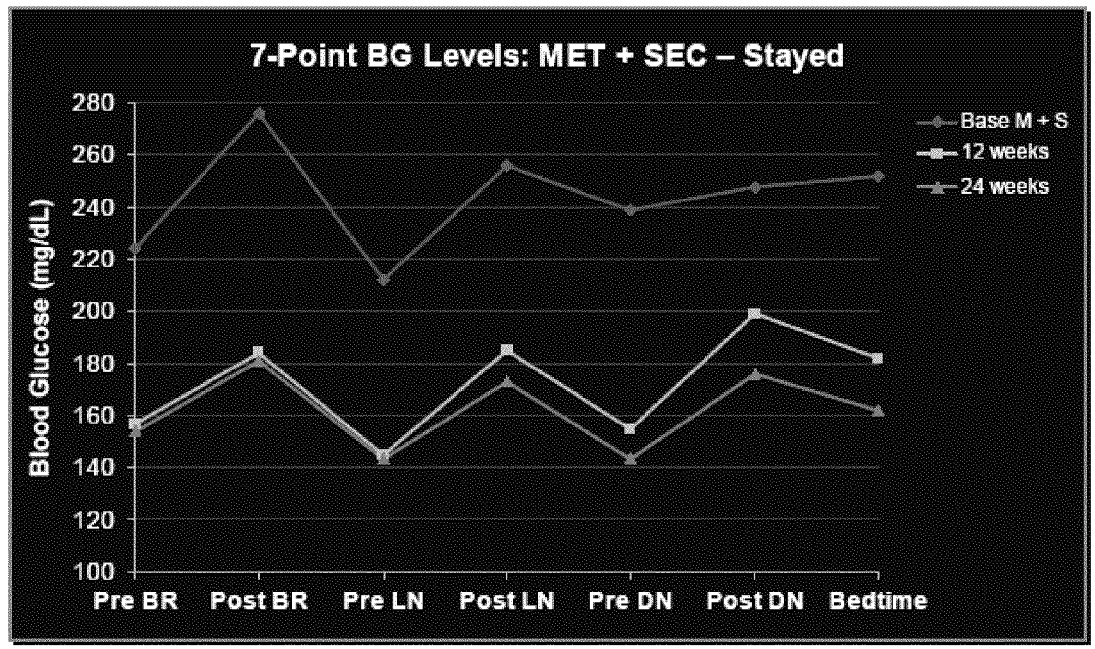
FIG. 21 depicts blood glucose levels after 12 and 24 weeks of treatment with metformin and a secretagogue.
Figure 22:
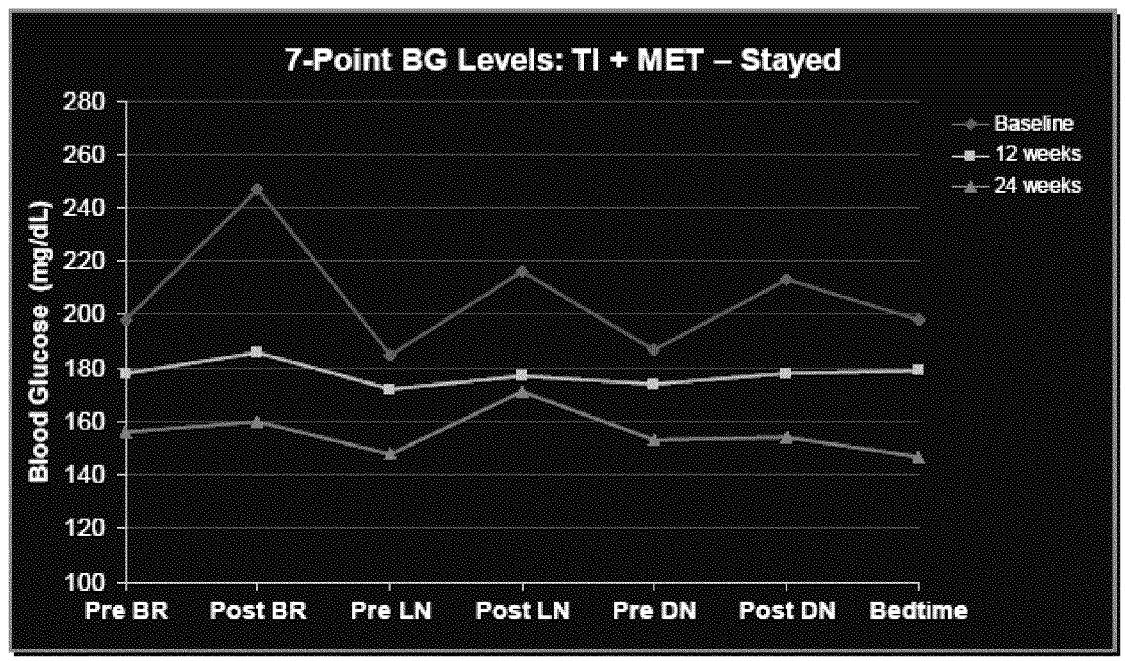
FIG. 22 depicts blood glucose levels after 12 and 24 weeks of treatment with TI and metformin.

For those subjects that completed the trial, metformin+secretagogue was successful in providing a clinically significant mean reduction from baseline in HbA1c (1.23 [1.1] %) after 24 weeks, but with significantly less effective postprandial control than the TI arms (FIGS. 17 and 18). The mean reduction from baseline in FPG and body weight was similar to that observed for the TI+metformin arm (FIGS. 21-22). The overall incidence of mild-to-moderate hypoglycemia was 20.8%.

Figure 23:
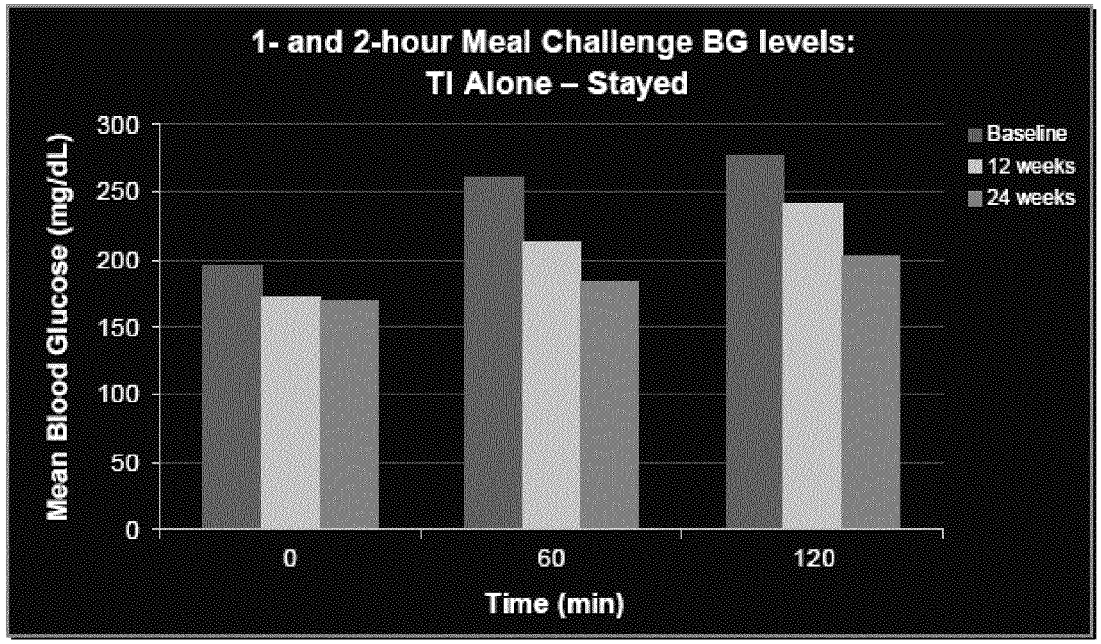
FIG. 23 depicts 1- and 2-hour postprandial blood glucose levels after 12 and 24 weeks of treatment with TI alone.
Figure 24:
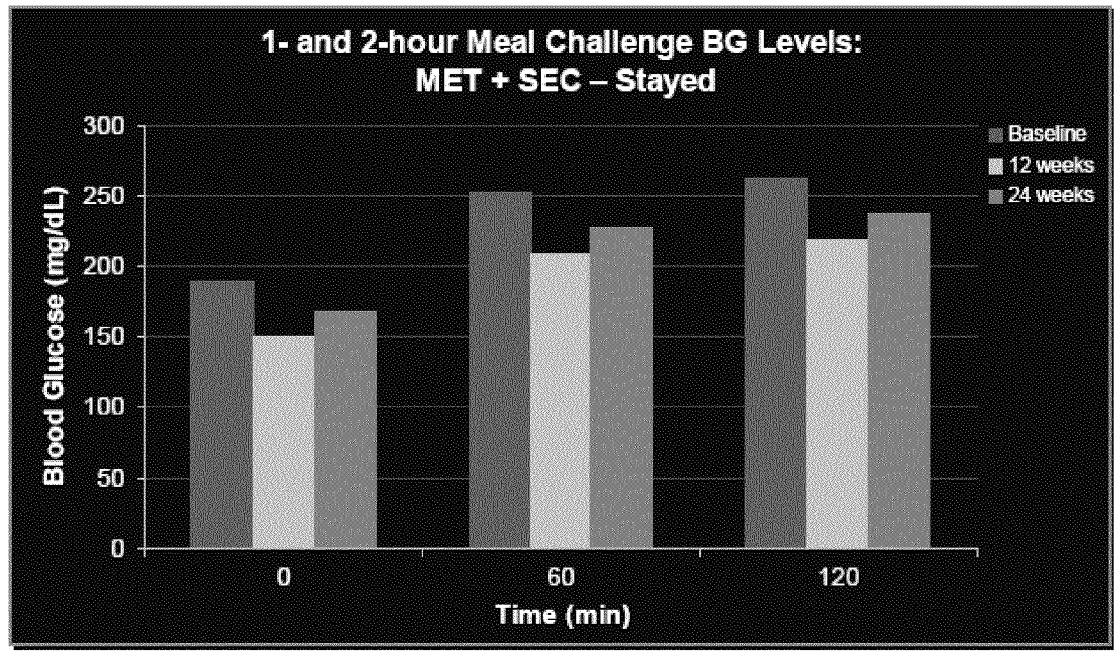
FIG. 24 depicts 1- and 2-hour postprandial blood glucose levels after 12 and 24 weeks of treatment with metformin and a secretagogue.
Figure 25:
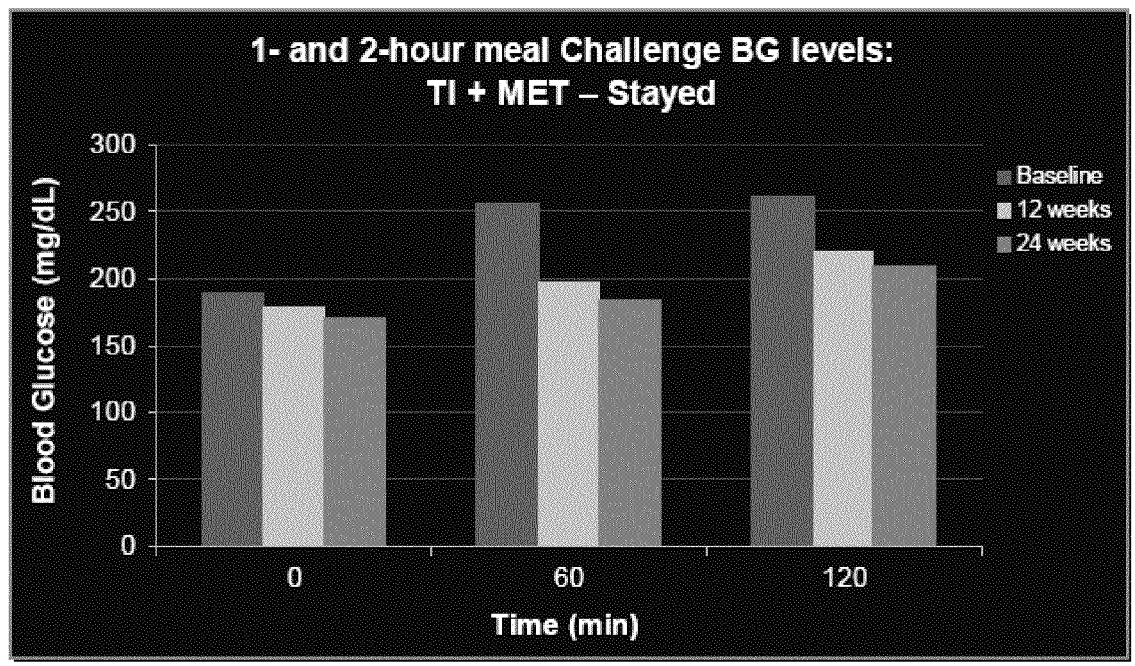
FIG. 25 depicts 1- and 2-hour postprandial blood glucose levels after 12 and 24 weeks of treatment with TI and metformin.
Figure 26:
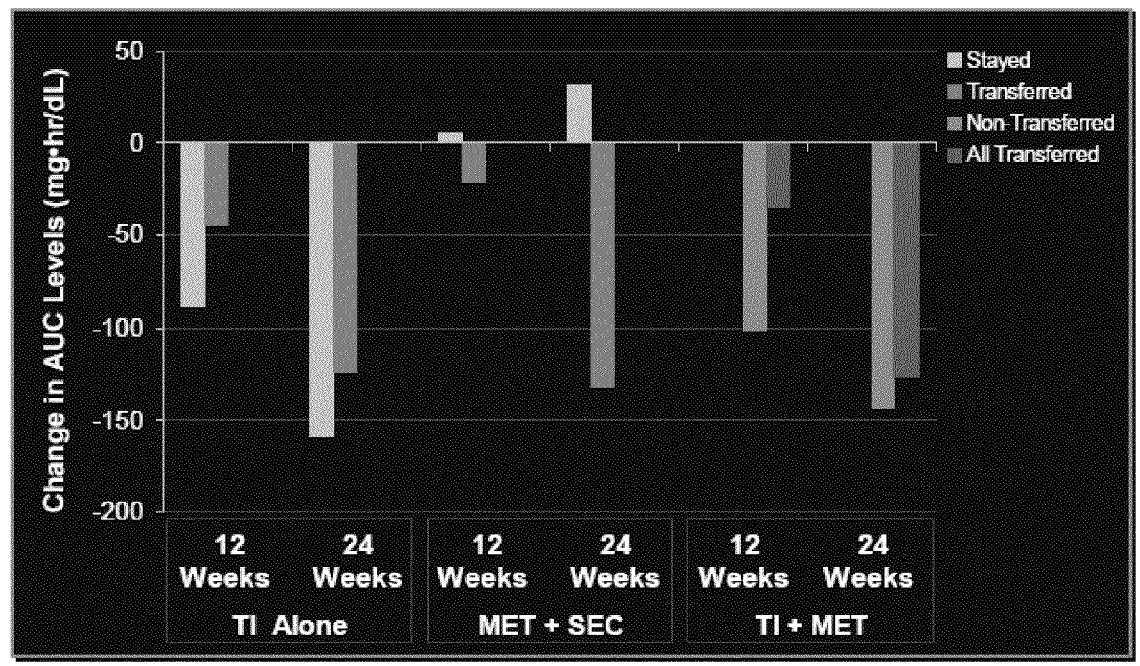
FIG. 26 depicts changes in postprandial glucose excursions (measured as change in AUC levels (mg·hr/dL) after 12 and 24 weeks of treatment with metformin and a secretagogue.
Figure 27:
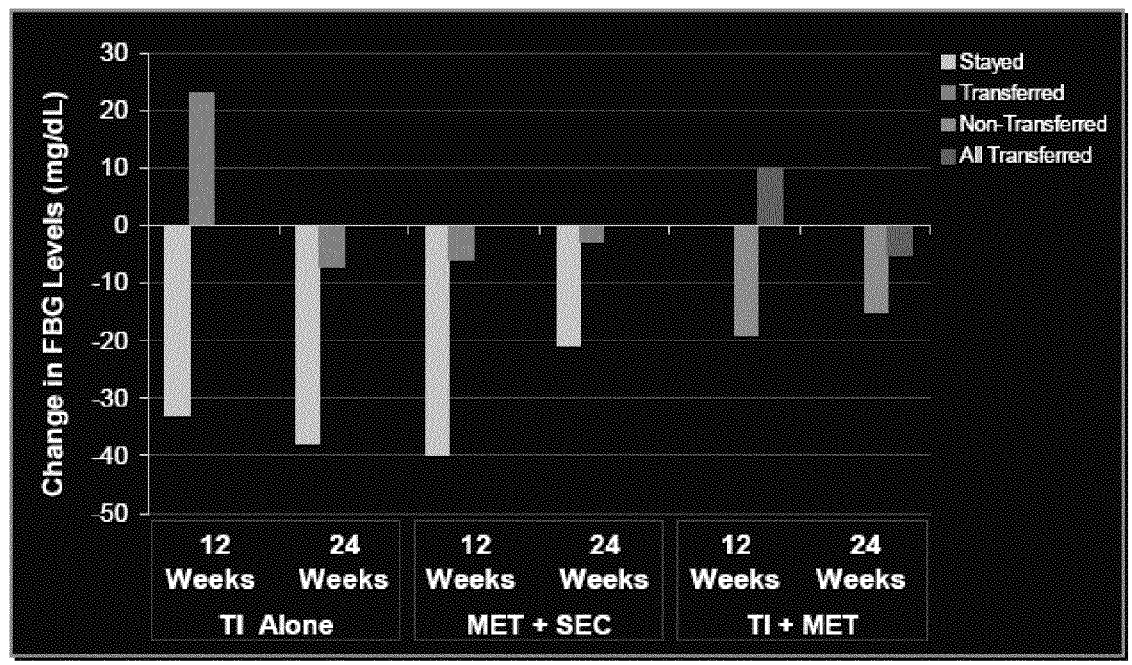
FIG. 27 depicts fasting blood glucose levels at 12 and 24 weeks after treatment with TI alone, TI and metformin, or metformin and a secretagogue.
Figure 28:
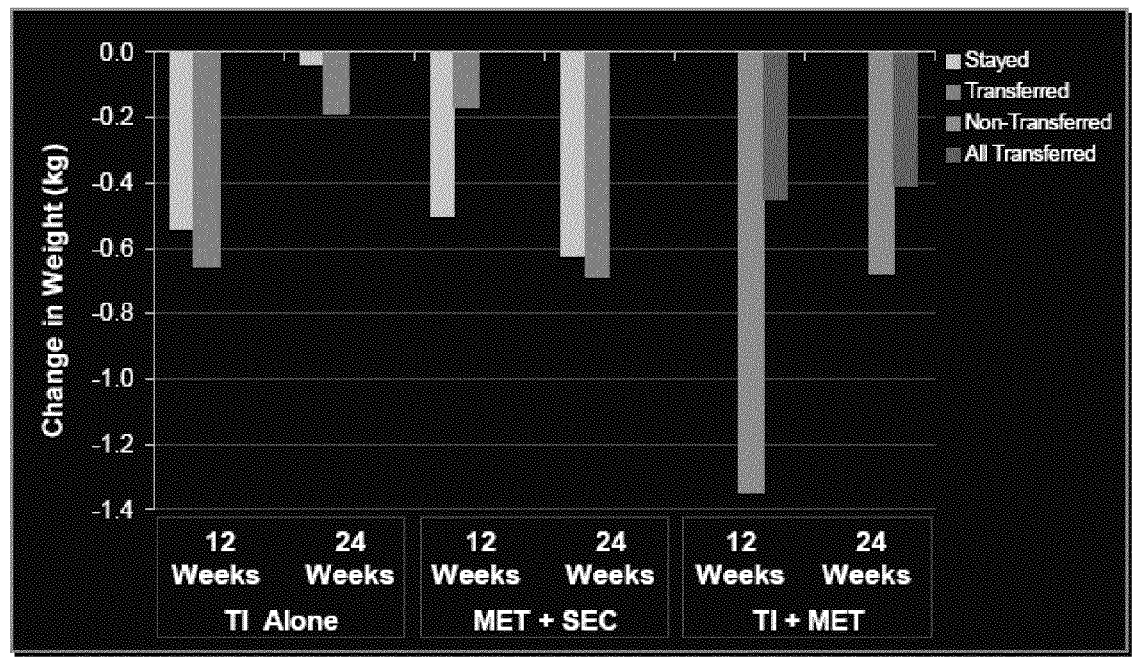
FIG. 28 depicts changes in weight at 12 and 24 weeks after treatment with TI alone, TI and metformin, or metformin and a secretagogue

Prandial TI alone or in combination with metformin significantly lowers HbA1c levels over the course of 12 and 24 weeks (FIGS. 23-25). This is achieved by controlling blood glucose levels over a 24 hour period as demonstrated by 7-point blood glucose levels. TI's main effect is by reducing post-prandial blood glucose excursion as evidenced by reductions in 1 and 2-hour post-prandial glucose levels, AUC and Cmax. The data from this trial support the use of prandial TI in combination with metformin in subjects with type 2 diabetes who require improvements in both postprandial and FPG (FIGS. 26-28). They also indicate a potential for use of prandial TI as monotherapy in subjects with type 2 diabetes who require an improvement in postprandial glycemic control but who have adequate control with respect to FPG.

The majority of patients with type 2 diabetes will eventually require treatment with insulin in order to maintain glycemic control. Treatment with prandial TI alone or in combination with metformin provides effective glycemic control with no weight gain. This is particularly important for patients with type 2 diabetes who are often overweight or obese.

Summary

The data demonstrate that TI alone or in combination with metformin clinically and significantly reduced HbA1c over 12 and 24 weeks without weight gain. TI alone or in combination with metformin controls overall daily blood glucose levels better than metformin+secretagogue based on 7-point blood glucose levels.

The data also demonstrate that TI alone or in combination with metformin controls postprandial glucose excursions better than metformin+secretagogue (1) at 1-hr and 2-hr in meal challenge tests; (2) AUC levels at 12 and 24 weeks; (3) 1-hr and 2-hr postprandial glucose levels ($\leq$180 mg/dL) at 12 and/or 24 weeks; and (4) 1-hr and 2-hr postprandial glucose levels ($\leq$140 mg/dL) at 12 and/or 24 weeks.

In addition, TI alone or in combination with metformin lowers fasting blood glucose at 12 and 24 weeks.

Overall, incidence of hypoglycemia was low in all treatment groups.

Moreover, mean changes from baseline in lung function tests including FEV1, FVC, TLC and DLco-HB1 for the TI alone and TI+metformin groups were not significantly different from the metformin+secretagogue group at week 12 or week 24

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of controlling glycemia related to one or more daily meals in an individual with diabetes without adjusting an insulin dose for meal content comprising the step of administering a standard dosage of an ultrarapid acting insulin formulation at a mealtime for one or more of the daily meals, wherein, for any given daily meal, the standard dosage for the daily meal has been predetermined based on said individual's usual meal content for the daily meal, and wherein, at least occasionally, content of the daily meal varies from $\geq$25% to $\leq$250% of the individual's usual meal content, and the standard dosage is not adjusted when a meal is consumed that varies from $\geq$25% to $\leq$250% of the individual's usual meal content as used in the determination of the standard dosage.

2. The method of claim 1 wherein the ultrarapid-acting insulin formulation is insulin-FDKP.

3. The method of claim 1 wherein a standard dosage is administered at each mealtime.

4. The method of claim 1 wherein a single predetermined dosage is used for each mealtime.

5. The method of claim 1 wherein a predetermined dosage is set for each mealtime.

6. The method of claim 1 wherein meal content is assessed as glycemic load.

7. The method of claim 1 wherein meal content is assessed as caloric content.

8. The method of claim 1 wherein meal content is $\geq$25% of a usual meal content as used in predetermination of the standard dose.

9. The method of claim 8 wherein meal content is ≧50% of a usual meal content as used in predetermination of the standard dose.

10. The method of claim 1 wherein meal content is ≦200% of a usual meal content as used in predetermination of the standard dose.

11. The method of claim 10 wherein meal content is ≦150% of a usual meal content as used in predetermination of the standard dose.

* * * * *

UNITED STATES PATENT AND TRADEMARK OFFICE
CERTIFICATE OF CORRECTION

| | | |
|---|---|---|
| PATENT NO. | : 8,258,095 B2 | Page 1 of 1 |
| APPLICATION NO. | : 12/539499 | |
| DATED | : September 4, 2012 | |
| INVENTOR(S) | : Boss et al. | |

It is certified that error appears in the above-identified patent and that said Letters Patent is hereby corrected as shown below:

In the Specification,

At column 18, line 59, "insulin lowering activity" should be changed to --glucose lowering activity--.

At column 18, lines 61-62, "insulin lowering activity" should be changed to --glucose lowering activity--.

Signed and Sealed this
Tenth Day of November, 2015

Michelle K. Lee
*Director of the United States Patent and Trademark Office*